United States Patent [19]

Brodeur et al.

[11] Patent Number: 5,919,620
[45] Date of Patent: Jul. 6, 1999

[54] **HEAT SHOCK PROTEIN HSP72 OF *STREPTOCOCCUS PNEUMONIAE***

[75] Inventors: Bernard R. Brodeur, Sillery; Denis Martin, St.-Augustin; Josée Hamel, Sillery, all of Canada

[73] Assignee: Biochem Vaccines Inc., Ste-Foy, Canada

[21] Appl. No.: 08/472,534

[22] Filed: Jun. 7, 1995

[51] Int. Cl.⁶ .............................. C12Q 1/06; C12Q 1/68; C12P 21/06; G01N 33/53
[52] U.S. Cl. ................................ 435/6; 435/4; 435/69.1; 435/963; 536/23.4; 536/23.7
[58] Field of Search .............................. 435/4, 963, 69.1, 435/6; 536/23.7, 23.4

[56] References Cited

U.S. PATENT DOCUMENTS 5,288,639  2/1994  Burnie et al. .

FOREIGN PATENT DOCUMENTS

WO 89/12455  12/1989  WIPO .
WO 90/02564  3/1990  WIPO .

OTHER PUBLICATIONS

K. Z. Abshire & F. C. Neidhardt, "Analysis of Proteins Synthesized by *Salmonella typhimurium* during Growth within a Host Macrophage," *J. Bacteriol.*, 175(12), pp. 3734–3743 (Jun. 1993).
D. Ang et al., "Biological Role and Regulation of the Universally Conserved Heat Shock Proteins," *J. Biol. Chem.*, 266(36), pp. 24233–24236 (Dec. 25, 1991).
R. Austrian, "Pneumococcal Vaccine: Development and Prospects," *Am. J. Med.*, 67(4), pp. 547–549 (Oct. 1979).
G. J. Boulnois, "Pneumococcal proteins and the pathogenesis of disease caused by *Streptococcus pneumoniae*," *J. Gen. Microbiol.*, 138, pp. 249–259 (1992).
D. G. Braun et al., "Rabbit Antibodies To Streptococcal Carbohydrates: Influence Of Primary And Secondary Immunization And Of Possible Genetic Factors On The Antibody Response," *J. Exp. Med.*, 129(4), pp. 809–830 (Apr. 1, 1969).
N. A. Buchmeir & F. Heffron, "Induction of Salmonella Stress Proteins upon Infection of Macrophages," *Science*, 248, pp. 730–732 (May 1990).
S. L. Danilition et al., "The 75–Kilodalton Protein of *Chlamydia trachomatis*: a Member of the Heat Shock Protein 70 Family?" *Infect. Immun.*, 58(1), pp. 189–196 (Jan. 1990).
B. Dworniczak & M. E. Mirault, "Structure and expression of a human gene coding for a 71 kd heat shock 'cognate' protein," *Nucleic Acids Res.*, 15(13), pp. 5181–5197 (1987).
H. D. Engers et al., "Letter to the Editor: Results of a World Health Organization–Sponsored Workshop on Monoclonal Antibodies to *Mycobacterium leprae*," *Infect. Immun.*, 48(2), pp. 603–605 (May 1985).
D. M. Engman et al., "Human Humoral Immunity To hsp70 During *Trypanosoma cruzi* Infection," *J. Immunol.*, 144(10), pp. 3987–3991 (May 15, 1990).

B. B. Finlay et al., "Epithelial Cell Surfaces Induce Salmonella Proteins Required for Bacterial Adherence and Invasion," *Science*, 243, pp. 940–943 (Feb. 17, 1989).
C. Georgopoulos & W. J. Welch, "Role Of The Major Heat Shock Proteins As Molecular Chaperones," *Annu. Rev. Cell Biol.*, 9, pp. 601–634 (1993).
D. J. Glass et al., "Conserved Sequences and Transcription of the hsp70 Gene Family in *Trypanosoma brucei*," *Mol. Cell Biol.*, 6(12), pp. 4657–4666 (Dec. 1986).
J. Hamel et al., "A monoclonal antibody directed against a serotype–specific outer membrane protein of *Haemophilus influenzae* type b," *J. Med. Microbiol.*, 23, pp. 163–170 (1987).
T.D. Ingolia, "Sequence of Three Copies of the Gene for the Major Drosophila Heat Shock Induced Protein and Their Flanking Regions," *Cell*, 21, pp. 669–679 (Oct. 1980).
S. H. E. Kaufmann et al., "Enumeration of T cells reactive with *Mycobacterium tuberculosis* organisms and specific for the recombinant mycobacterial 64–kDa protein," *Eur. J. Immunol.*, 17, pp. 351–357 (1987).
R. M. Krause, "The Search for Antibodies with Molecular Uniformity," *Adv. Immunol.*, 12, pp. 1–56 (1970).
U. K. Laemmli, "Cleavage of Structural Proteins during the Assembly of the Head of Bacteriophage T4," *Nature*, 227, pp. 680–685 (Aug. 15, 1970).
C. J. Lee et al., "Virulence, Immunity, and Vaccine Related to *Streptococcus pneumoniae*," *Crit. Rev. Microbiol.*, 18(2), pp. 89–114 (1991).
S. Lindquist, "The Heat Shock Response," *Ann. Rev. Biochem.*, 55, pp. 1151–1191 (1986).
B. J. Luft et al., "Immunologic And Structural Characterization Of The Dominant 66– To 73–kDa Antigens Of *Borrelia burgdorferi*," *J. Immunol.*, 146(8), pp. 2776–2782 (Apr. 15, 1991).
D. Martin et al., "Heterohybridomas secreting human monoclonal antibodies against *Haemophilus influenzae* type b," *Eur. J. Immunol.*, 18, pp. 601–606 (1988).
P. Matsudaira, "Sequence from Picomole Quantities of Proteins Electroblotted onto Polyvinylidene Difluoride Membranes," *J. Biol. Chem.*, 262(21), pp. 10035–10038 (1987).
L. S. McDaniel et al., "Monoclonal Antibodies Against Protease–Sensitive Pneumococcal Antigens Can Protect Mice From Fatal Infection With *Streptococcus Pneumoniae*," *J. Exp. Med.*, 160, pp. 386–397 (Aug. 1984).

(List continued on next page.)

*Primary Examiner*—James C. Housel
*Assistant Examiner*—Rodney P. Swartz
*Attorney, Agent, or Firm*—Foley & Lardner

[57] ABSTRACT

A heat shock protein of *Streptococcus pneumoniae* named HSP72 and immunologically related polypeptides, the nucleotide and derived amino acid sequences of HSP72 (SEQ ID NO:4; SEQ ID NO:5), antibodies that bind to HSP72, and recombinant DNA methods for the production of HSP72 and immunologically related polypeptides. The polypeptides, DNA sequences and antibodies of this invention provide new means for the diagnosis, prevention and/or treatment of disease.

4 Claims, 14 Drawing Sheets

OTHER PUBLICATIONS

L. S. McDaniel et al., "Analysis of a surface protein of *Streptococcus pneumoniae* recognised by protective monoclonal antibodies," *Microb. Pathogen.,* 1, pp. 519–531 (1986).

J. J. Mekalanos, "Environmental Signals Controlling Expression of Virulence Determinants in Bacteria," *J. Bacteriol.,* 174(1), pp. 1–7 (Jan. 1992).

R. B. Merrifield, "Solid Phase Peptide Synthesis. I. The Synthesis Of A Tetrapeptide," *J. Am. Chem. Soc.,* 85(14), pp. 2149–2154 (Jul. 20, 1963).

P. J. Murray & R. A. Young, "Stress and Immunological Recognition in Host–Pathogen Interactions," *J. Bacteriol.,* 174(13), pp. 4193–4196 (Jul. 1992).

F. C. Neidhardt et al., "The Genetics And Regulation Of Heat–Shock Proteins," *Ann. Rev. Genetics,* 18, pp. 295–329 (1984).

A. Noll et al., "Protective Role for Heat Shock Protein–Reactive αβ T Cells in Murine Yersiniosis," *Infect Immun.,* 62(7), pp. 2784–2791 (Jul. 1994).

V. Nussenzweig & R. S. Nussenzweig, "Rationale for the Development of an Engineered Sporozoite Malaria Vaccine," *Adv. Immunol.,* 45, pp. 283–334 (1989).

J. C. Paton et al., "Cloning and Expression in *Escherichia coli* of the *Streptococcus pneumonia* Gene Encoding Pneumolysin," *Infect. Immun.,* 54(1), pp. 50–55 (Oct. 1986).

J. C. Paton et al., "Molecular Analysis Of The Pathogenicity Of *Streptococcus Pneumoniae:* The Role of Pneumococcal Proteins," *Annu. Rev. Microbiol.,* 47, pp. 89–115 (1993).

B. J. Pearce et al., "Genetic identification of exported proteins in *Streptococcus pneumoniae,*" *Mol. Microbiol.,* 9(5), pp. 1037–1050 (1993).

B. B. Plikaytis et al., "Purified 60–Kilodalton Legionella Protein Antigen with Legionella–Specific and Nonspecific Epitopes," *J. Clin. Microbiol.,* 25(11), pp. 2080–2084 (Nov. 1987).

N. M. Rothstein et al., "*Onchocerca volvulus* heat shock protein 70 is a major immunogen in amicrofilaremic individuals from a filariasis–endemic area," *Molec. Biochem. Parasitol.,* 33, pp. 229–235 (1989).

H. Saito & Uchida, "Organization and Expression of the dnaJ and dnaK Genes of *Escherichia coli* K12," *Molec. Gen. Genet.,* 164, pp. 1–8 (1978).

F. Sanger et al., "DNA sequencing with chain–terminating inhibitors," *Proc. Natl. Acad. Sci. USA,* 74(12), pp. 5463–5467 (Dec. 1977).

M. T. Scott & R. A. Neal, "The vaccine potential of cell surface glycoproteins from *Trypanosoma cruzi,*" *Phil. Trans. R. Soc. Lond.,* vol. B 307, pp. 63–72 (1984).

P. A. Silver & J. C. Way, "Eukaryotic DnaJ Homologs and the Specificity of Hsp70 Activity," *Cell,* 74, pp. 5–6 (Jul. 16, 1993).

Z. Sokolovic & W. Goebel, "Synthesis of Listeriolysin in *Listeria monocytogenes* under Heat Shock Conditions," *Infect. Immun.,* 57(1), pp. 295–298 (Jan. 1989).

F. W. Studier & B. A. Moffatt, "Use of Bacteriophage T7 RNA Polymerase to Direct Selective High–level Expression of Cloned Genes," *J. Mol. Biol.,* 189, pp. 113–130 (1986).

S. Tabor & C. C. Richardson, "A bacteriophage T7 RNA polymerase/promoter system for controlled exclusive expression of specific genes," *Proc. Natl. Acad. Sci. USA,* 82, pp. 1074–1078 (Feb. 1985).

J. E. R. Thole et al., "Antigenic relatedness of a strongly immunogenic 65 kDA mycobacterial protein antigen with a similarly sized ubiquitous bacterial common antigen," *Microb. Pathogen.,* 4, pp. 71–83 (1988).

H. Towbin et al., "Electrophoretic transfer of proteins from polyacrylamide gels to nitrocellulose sheets: Procedure and some applications," *Proc. Natl. Acad. Sci. USA,* 76(9), pp. 4350–4354 (Sep. 1979).

E. A. Wagar et al., "Differential Human Serologic Response to Two 60,000 Molecular Weight *Chlamydia trachomatis* Antigens," *J. Infect. Dis.,* 162, pp. 922–927 (Oct. 1990).

R. F. Wang & S. R. Kushner, "Construction of versatile low–copy–number vectors for cloning, sequencing and gene expression in *Escherichia coli,*" *Gene,* 100, pp. 195–199 (1991).

M. Wetzstein et al., "Cloning, Sequencing, and Molecular Analysis of the dnaK Locus from *Bacillus subtilis,*" *J. Bacteriol.,* 174(10), pp. 3300–3310 (May 1992).

J. A. Wiley et al., "Monoclonal Anti–Idiotypes Induce Neutralizing Antibodies to Enterovirus 70 Conformational Epitopes," *J. Virol.,* 66(10), pp. 5744–5751 (Oct. 1992).

D. E. Yelton & M. D. Scharff, "Monoclonal Antibodies: A Powerful New Tool In Biology And Medicine," *Ann. Rev. Biochem.,* 50, pp. 657–680 (1981).

D. Young et al., "Stress proteins are immune targets in leprosy and tuberculosis," *Proc. Natl. Acad. Sci. USA,* 85, pp. 4267–4270 (Jun. 1988).

Wetzstein et al, "Complete Nucleotide sequence of the *Bacillus subtilis* dnaK gene" Nucleic Acids Research 18(8):2172 (1990).

Blander et al "Major Cytoplasmic Membrane Protein of *Legionella pneunophila*" J. Clin. Invest. 91:717–723, 1993.

Sheldrake et al "Induction of Heat Shock Proteins in Streptococcus mutans" J. Dent. Res. (I ADR Abstracts) 72:152, 1993.

Boutibonnes et al "Characterization of the heat shock response in *Enterococcus faecalis*" Ant. oran Leeunon. 64:47–55, 1993.

FIGURE 13A

```
Consensus      M------SKI IGIDLGTTNS CVAVLEG..P KVI.N.EG.R TTPS.VAF-K    50
DNAK_ECOLI     -......G... .......... ...IMD.TT. R.LE.A..D. ....II.YTQ    43
DNAK_BORBU     .......G... .......... ...IM.HGK. V..Q.S..G. ....I..YTN    44
DNAK_BRUOV     .......A.V .......... ...MD.KNA ...E.A..A. ....II...TD    44
DNAK_CHLPN     .SEHKKS... .......... ...S.M..GQA ...TSS..I. ....I.....    49
DNAK_BACME     .......... .......... .......GE. ....P.P..N ....V.....    43
DNA2_BACSU     ........V .......... .......GE. ....A.A..N ....V.....    43
DNAK_STAAU     .......... .......... ...T....DE. ....Q.P..S ....V.....    43
HSP72 SPNEU    .......... .......A.. .......TES .I.A.P..N ....V.S...    43
DNAK_LACLA     .......... .......A.. .......TES .I.P.P..N ....V.....    43
DNAK_MYCTU     .......ARA V........L .S.....GD. V.VA.S..S ....I...AR    44

Consensus      NGE..VG...A KHQAVINP.. T...SIKR.MG ---------- ----...KV-   100
DNAK_ECOLI     D..TL..QF. .........QN .LFA....LI. RRFQDEEVQR DVSIMPF.II    93
DNAK_BORBU     K..RL..QV. ..N.M....EN .IY.....F.. RRFEE..VAS EIKMVPY.IE    92
DNAK_BRUOV     GI.GVA.QF. .........EG .LFAV...LI. RRYDDPMVTK DKDLVPY.IV    94
DNAK_CHLPN     GN.KL..IF. .........EK .LG.I..FI. RKYSE..VAS EIQTVPYT.T    97
DNAK_BACME     ...RQ..EV. ....I....N- .II.V..H.. .......... ....TDH...    77
DNA2_BACSU     ...RQ..EV. ....SI...N- .IM....H.. .......... ....TDY...    77
DNAK_STAAU     ...TQ..EV. ....I....N- .VQ....H.. .......... ....TDY...    77
HSP72 SPNEU    ...II..DA. .........D- .VI....SK.. .......... ....TSE...    77
DNAK_LACLA     ...II..DA. .........E- .II....SK.. .......... ....TSE...    77
DNAK_MYCTU     ..VL..QF. .N....VDR .VR.V..H.. .......... ....SDWSI.    79

Consensus      ---------E ..G--K.YTP .EISA.IIQ. IK.IAE.YLG E.VT.AVITV   150
DNAK_ECOLI     AADNGDAWV. VK...QKMA. PQ...EV.KK M.K..D... .P..E.....   141
DNAK_BORBU     KGLNGDARVN ISNIK.QMS. P....AT.IK M.E...A... .K..E.....   142
DNAK_BRUOV     KGDNGDAWV. VH....K.S. SQ...M...K M.E...S... .T..Q.....   142
DNAK_CHLPN     SGSKGDAVF. VD....Q... E..G.Q.MK M.E...A... .T..E.....   145
DNAK_BACME     .......... AE....Q... Q.M..I...H ..GY..D... .P..K.....   116
DNA2_BACSU     .......... IE....D... Q.V..I...H ..SY..S... .T.SK.....   116
DNAK_STAAU     ........D IE....S... Q....M...N ..N...S... .K.DK.....   116
HSP72 SPNEU    ........S AN....E... Q....M...Y ..GY..D... .K..K.....   116
DNAK_LACLA     ........S AN....E... Q....M...N ..A...S... .K.EK.....   116
DNAK_MYCTU     .......... ID....K..A P...LR.LMK .RI..A... DI.I......   118

Consensus      PAYFNDAQRQ ATKDAGKIAG LEV.RILNEP TAAALAYGLD K......IIV   200
DNAK_ECOLI     .......... .......... ......K.. .......... GTGNRT.A.   191
DNAK_BORBU     .......... .......... ......K.V. .........IE KHEE-IVA.   191
DNAK_BRUOV     .......... .......... ......L... .......... SEGK-T.A.   191
DNAK_CHLPN     ......S.A S......R.. ......D.K.E .........I. VGDK-K.A.   194
DNAK_BACME     ......E... .......... ......E... .........E TDEDQTV..   166
DNA2_BACSU     ......E... .......... ......E... .......... TDEDQT...   166
DNAK_STAAU     ......E... .......... ......E... .......... TDKDEKV..   166
HSP72 SPNEU    .......... .......... ......E.V. .......... TDKEEK...   166
DNAK_LACLA     .......... .......... ......E.V. .......... TDKDEK...   166
DNAK_MYCTU     .......... .......Q.. ......N.V. ......PG... GEKEQR...   168
```

FIGURE 13B

```
Consensus     .DLGGGTFDV SILELGD--G --VFEV.ST. GDN.LGGDDF DQ.IID.LV.   250
DNAK_ECOLI    Y........I ..I.IDEVL. EKT....LA.N ..TH...E.. .SRL.NY..E   241
DNAK_BORBU    Y........I .......... .K.N ..TH....N. .DE..KH.IS          237
DNAK_BRUOV    Y......... .V..I..... .K.N ..TF...E.. .IRLVEY..A          237
DNAK_CHLPN    F........I ....I..... .L.N ..TL...... .EV..KWMIE          240
DNAK_BACME    Y......... .......... .RA.A ..R..... ..V...Y..A            212
DNA2_BACSU    Y......... .......... .R.A ..R..... ..V...H..S              212
DNAK_STAAU    F......... .......... .L.A ..K..... ..V...Y..A              212
HSP72 SPNEU   F......... .......... .LL.A ..K..... ..K...H..A             212
DNAK_LACLA    F......... .......... .LA.A .N.K.... ..K...WM.A             212
DNAK_MYCTU    H......... .L..II.E.. ..V.RA.S ..H.....W L.RVV.W..D         214

Consensus     HFKKE.GIDL S.DKMALQRL KLAAEKAK.. LSGV..T.I. LPFITA.-..   300
DNAK_ECOLI    ...DQ..... RN.PL.M... ..E.....IE ..SAQQ.DVN ..M...D.AT   290
DNAK_BORBU    ...SA..... ..N....... ..E.....IE ...AQEAS.N ......D.AN   286
DNAK_BRUOV    ...S...... KN..I..... ........TE ..SSQQ.E.N ......D.QT   286
DNAK_CHLPN    ...QE..... ..K.N..... ........IE ....SS.E.N Q...MD.AQ    289
DNAK_BACME    ...N.V.... .K........ .........KD ....TS.Q.S ....G.EA    261
DNA2_BACSU    ...N...... .K........ .........KD ....SS.Q.S ....G.EA    261
DNAK_STAAU    ...N.V.... .Q........ .........KD ....SQ.Q.S ...S.G.EN   261
HSP72 SPNEU   ...N...... .T........ .....M...KD ....TS.Q.S ....G.EA    261
DNAK_LACLA    ...N...... GQ........ .........KD ....TT.Q.S ....G.AA    261
DNAK_MYCTU   K..GTS.... ITK....M.. RF......IE .SSQS.S.N LM..VDADK    264

Consensus     GPLHL...LT RAKFE.L... LV.RT..P.. .AL.DAGLS. S.ID.VILVG   350
DNAK_ECOLI    ..K.MNIKV. ..L.S.VED .N.SIE.LK V..Q....V .D..D.....   340
DNAK_BORBU    .K..QYT... .....QMVDH ..QK.KE.CL K.IK....KA .D.NE.....   336
DNAK_BRUOV    .K..AIK.S. .NV.S.VDD A.HA.VE.CK A..K....KA GE..E.M...   336
DNAK_CHLPN    .K..ALT... .Q..K.AAS .IE..KS.CI K..S....K.A KD..D.L...   339
DNAK_BACME    ....EVS.S. ...DE.SAG .E..MA.VR Q..K......A .EL.K.....   311
DNA2_BACSU    ....ELT... ....E.SSH .E..MG.VR Q..Q......A .E..K.....    311
DNAK_STAAU    ....EVN... S...E.SDS .IR..ME.TR Q.MK....TN .D..E.....   311
HSP72 SPNEU   ....EMT... ...DD.TRD .E..KV.VR Q..S......L .E..F.....   311
DNAK_LACLA    ....EMA... ...DE.THD .EA.RQ.VR Q..S....T .D..E.L...    311
DNAK_MYCTU   N..F.DEQ.. L.E.QRITQD .LD..RK.FQ SVIA.T.I.V .E..H.M...   314

Consensus     GSTRIPAVQ. .VK...G-KE PNKGVNPDEV VA.GAAIQGG VLTGDVKDVV   400
DNAK_ECOLI    .Q..M.M..K K.AEFF.... .R.D....A .D...M..... ........L    389
DNAK_BORBU    .....I.K I..DIF..QD ........A .D......I...ET..M.           385
DNAK_BRUOV    .M..EI.K C..AFF.... .H......M ........Q.E....L            385
DNAK_CHLPN    .MS.M....E T..ELF.... ........I ........Q.E....L             388
DNAK_BACME    ........D AI.KET..QD .H......L ........I........            360
DNA2_BACSU    ........E AI.KET.... AH......M ........I........           360
DNAK_STAAU    ........E A..KEI.... ........M ........I........           360
HSP72 SPNEU   ........VE A..AET.... ...S....M ........I........          360
DNAK_LACLA    ........VE L.RHETN... ...S....M ........I........          360
DNAK_MYCTU   L...M..TD L..ELT.G.. ....L...M ...A....K.E....L            364
```

FIGURE 13C

| | | | | | | |
|---|---|---|---|---|---|---|
| Consensus | LLDV.PLSLG | IET.GGV.T. | L.IERNTTIPT | .KSQVFSTAA | DNQ.AVDIHV | | 450 |
| DNAK_ECOLI | ....... | ...M..M.T | ..AK...... | KH.......E | ...S..T... | 439 |
| DNAK_BORBU | ....... | ...I..M.K | .......... | K......... | ...TS...K. | 435 |
| DNAK_BRUOV | ....... | ...I..F.R | .......... | K...T....E | ...S..T.R. | 435 |
| DNAK_CHLPN | ...I... | ...I..M.T | .V........ | Q.K.I..... | ...P..T.V. | 438 |
| DNAK_BACME | ....... | ...M..F.K | .......... | S......... | .S.T...... | 410 |
| DNA2_BACSU | ....... | ...M..F.K | ..D....... | S......... | ...T...... | 410 |
| DNAK_STAAU | ....... | ..IL..RMNT | .......... | S...IY...V | ...PS...V. | 410 |
| HSP72 SPNEU | ....... | ...M..F.K | ..D....... | S......... | ...P...... | 410 |
| DNAK_LACLA | ....... | ...M..F.K | ..D....... | S......... | ...P...... | 410 |
| DNAK_MYCTU | ....... | ...R..M.R | .......... | KR.ET.T..D | ..PS..Q.Q. | 414 |

| | | | | | | |
|---|---|---|---|---|---|---|
| Consensus | LQGERPMAAD | NK.LGRF.LT | LIPHARG.P | QIEV.FDID. | NGIV.V.AKD | 500 |
| DNAK_ECOLI | ....KR.... | ..S.Q.N..D | G.N......M. | ..........A | T..LH.S... | 489 |
| DNAK_BORBU | .....E...Q | .RI..N.I..D | G..A.....V. | ........S..A | ...H.S... | 485 |
| DNAK_BRUOV | R.ASVKL... | ...L..Q.I.V | G.......VR | ........S..A | ...N.S... | 485 |
| DNAK_CHLPN | ......K... | ..EI..I... | .......H.. | ........S..A | ..FH.S... | 488 |
| DNAK_BACME | ......S... | ...T..Q... | .......V.. | ........S..K | ...N.R... | 460 |
| DNA2_BACSU | ......S... | ...T..Q... | .......V.. | ........S..K | ...N.R... | 460 |
| DNAK_STAAU | .......... | ...T..Q... | .....E..K. | ...........K | ...N.I... | 460 |
| HSP72 SPNEU | .......... | ...T..Q... | .....A..I. | ...........K | ...S.K... | 460 |
| DNAK_LACLA | .......... | ...T..Q... | .....A..I. | ...........K | ...S.K... | 460 |
| DNAK_MYCTU | Y....EI..H | ...L..S... | G......I.. | ...........A | ...H.I... | 464 |

| | | | | | | |
|---|---|---|---|---|---|---|
| Consensus | .GT.KEQ.I. | I.SSSGLSD. | HIDRMVKIAE | ANAEADKKR. | EEV..RNEAD | 550 |
| DNAK_ECOLI | KNSG...K.T | .KA....NED | ..QK..R... | ......R.FE | L.QT..QG. | 539 |
| DNAK_BORBU | M..G...K.R | .E.....ES | .......... | .H.E...LK | .NIEAK.T.N | 535 |
| DNAK_BRUOV | G.VF..HQ.R | .QA.G....A | I.EK...... | ........R | .S.EAK.Q.E | 535 |
| DNAK_CHLPN | VASG...K.R | .EA....QED | ..Q...R... | I.K.E....R | .ASDAK.... | 538 |
| DNAK_BACME | L..N...A.T | .K.T....D | ........E. | E.D....Q.K | ...EL..... | 510 |
| DNA2_BACSU | L..G...N.T | .K......E | ....E..E.. | E.D..A.KK | ..IEV..... | 510 |
| DNAK_STAAU | L..N...R.T | .Q..S....E | .......... | V......R | ..DL..... | 510 |
| HSP72 SPNEU | L..Q...T.V | .Q.N...T.E | .....M.... | ......S...K | ..DL...V. | 510 |
| DNAK_LACLA | L..Q...T.V | .K.N.....E | .....K.M.. | ...D..A..K | ..DT...... | 510 |
| DNAK_MYCTU | K..G..NV.R | LQEG...KE | I....I.... | .H..FR..R | L.ADV.LQ.E | 514 |

| | | | | | | |
|---|---|---|---|---|---|---|
| Consensus | .LVF.TEK.L | K....K..E. | ...K..E.A.. | .LK.ALE..D | ....-IKAK... | 600 |
| DNAK_ECOLI | H.LHS.R.QV | EEAGD.LPAD | DKTAI.S.LT | A.ET..KGE. | KAA..E..MQ | 588 |
| DNAK_BORBU | S.IYQ...S. | .EYSE.ISSE | DKEAI.SKIK | E..ES..KE. | -ISL...SRTE | 584 |
| DNAK_BRUOV | S...HS...S. | AEYGD.VSAD | DK.AI.D.IA | A..TS..GE. | -AED....TQ | 584 |
| DNAK_CHLPN | SMI.RA...AI | .DYKEQIP.T | LV.EI.ERIE | NVRN...KDDA | PIEK..EVTE | 588 |
| DNAK_BACME | Q...T...T. | .DLEG.VE.A | EVTKANE.KD | A..A.I.KN. | LEE.....KD | 559 |
| DNA2_BACSU | Q...Q...T. | .DLEG.VD.E | QV.KAND.KD | A..A.I.KNE | FEE.....KD | 559 |
| DNAK_STAAU | S...QV..T. | TDLGENIG.E | DK.SA.EKKD | A..T...GQ. | IED...S.KE | 559 |
| HSP72 SPNEU | QAI.A...TI | .ETEG.GFDA | ERDAAQA.LD | D..K.Q.DNN | LDD.M...LE | 559 |
| DNAK_LACLA | A...Q...T. | .DLEG.VE.A | EV.KA.D.KE | E..K...GE. | IDD.....SE | 559 |
| DNAK_MYCTU | T...YQ..LFV | .EQRE--A.G | GS.VP.DTLN | KVDA.VAEAE | -GG.-TWRIG | 559 |

FIGURE 13D

```
Consensus    .L....Q.L.  ...-YE----  -.A..AQ...  ..........  ...-------  650
DNAK_ECOLI   E.AQVS.K.M  EIA.-Q....  .QQHAQ.QTA  GADASANNAK  DDD.......  624
DNAK_BORBU   E.QKASYKIA  EMM..KDSSQ  QN.NSQ.ENG  PQSNTSEEGK  EADY......  627
DNAK_BRUOV   A.AEVSMK.G  QAM...AAQA  AEGAG.EGGE  QASSSKDDVV  DADY......  627
DNAK_CHLPN   D.SKHM.KIG  ESMQSQSASA  AASSA.NAKG  GPNINTEDLK  KHSFSTKPPS  638
DNAK_BACME   E.QEIV.A.T  VKL.......  .Q.QQ..-Q-  ---A----GE  QGA.......Q  588
DNA2_BACSU   E.QTIV.E.S  MKL.......  .E.AK..-Q-  ---AQGGANA  EGK.......A  592
DNAK_STAAU   E.EKVI.E.S  AKV.......  .Q.AQQ.-QQ  AQGANAGQNN  DST.......  595
HSP72_SPNEU  A.NEKA.G.A  VKL.......  .Q.AA..---  ----QAQEGA  EGA.QATGNA  595
DNAK_LACLA   A.SEIA.N.A  VKL.......  .Q.NA..GEA  SEATDAQEGP  KDA.......  596
DNAK_MYCTU   YFGHQVGDGE  AGPGVA....  .GSGASDLRS  SSGCVTGHWR  CPP.......  597

Consensus    --...D.E..  E...------  ..                                  672
DNAK_ECOLI   ..-VV.A.FE  .VKD......  KK                                  637
DNAK_BORBU   ..----EVVD  .---...DKK  --                                  635
DNAK_BRUOV   ..----E.ID  D---...NKK  SS                                  637
DNAK_CHLPN   NNGSSEDHIE  .ADVEIIDND  DK                                  660
DNAK_BACME   NDDVV.A.FE  .VNDD.....  KK                                  605
DNA2_BACSU   DDNVV.A.YE  .VNDDQN...  KK                                  611
DNAK_STAAU   ...-VE.A.FN .VKDDDK...  --                                  609
HSP72_SPNEU  GDDVV.G.FT  .K--......  --                                  607
DNAK_LACLA   ..NTF.GDFE  .SK-......  --                                  607
DNAK_MYCTU   ..RRRAGRCP  PRLG......  --                                  609
```

HEAT SHOCK PROTEIN HSP72 OF STREPTOCOCCUS PNEUMONIAE

TECHNICAL FIELD OF THE INVENTION

This invention relates to a novel heat shock protein of *Streptococcus pneumoniae* and immunologically related polypeptides, which provide the basis for new immunotherapeutic, prophylactic and diagnostic agents useful in the treatment, prevention and diagnosis of disease. More particularly, this invention relates to a heat shock protein of *S. pneumoniae* named HSP72, which has an apparent molecular mass of 72 kilodaltons, to the corresponding nucleotide and derived amino acid sequences, to recombinant DNA methods for the production of HSP72 and immunologically related polypeptides, to antibodies that bind to HSP72, and to methods and compositions for the diagnosis, prevention and treatment of diseases caused by *S. pneumoniae* and related bacteria.

BACKGROUND OF THE INVENTION

*S. pneumoniae* is an important agent of disease in humans, especially among infants, the elderly and immunocompromised persons. It is a bacterium frequently isolated from patients with invasive diseases such as bacteraemia/septicaemia, pneumonia, and meningitis with high morbidity and mortality throughout the world. Although the advent of antimicrobial drugs has reduced the overall mortality from pneumococcal diseases, the presence of resistant pneumococcal organisms has become a major problem in the world today. Effective pneumococcal vaccines could have a major impact on the morbidity and mortality associated with *S. pneumoniae* disease. Such vaccines would also potentially be useful to prevent otitis media in infants and young children.

It is clear that a number of pneumococcal factors are potentially important in the pathogenesis of disease [G. J. Boulnois, *J. Gen. Microbiol.*, 138, pp. 249–259 (1992); C. J. Lee et al., *Crit. Rev. Microbiol.*, 18, pp. 89–114 (1991)]. The capsule of the pneumococcus, despite its lack of toxicity, is considered to be the sine qua non of pneumococcal virulence. More than 80 pneumococcal capsular serotypes are identified on the basis of antigenic differences. Antibodies are the mechanism of protection and the importance of anticapsular antibodies in host defenses against *S. pneumoniae* is well established [R. Austrian, *Am. J. Med.*, 67, pp. 547–549 (1979)]. Nevertheless, the currently available pneumococcal vaccine, comprising 23 capsular polysaccharides that most frequently caused disease, has significant shortcomings such as the poor immunogenicity of capsular polysaccharides, the diversity of the serotypes and the differences in the distribution of serotypes over time, geographic areas and age groups. In particular, the failure of existing vaccines to protect young children against most serotypes has spurred evaluation of other *S. pneumoniae* components. Increasing evidence indicates that certain pneumococcal proteins may play an active role both in terms of protection and pathogenicity [J. C. Paton, *Ann. Rev. Microbiol.*, 47, pp. 89–115 (1993)]. So far, however, only a few *S. pneumoniae* proteins have been studied. This might result from the lack of proteinspecific antibodies which renders difficult the study of the role of protein antigens in protection and pathogenicity. It is believed that the pneumococcal protein antigens are not very immunogenic and that most antibody responses are to the phosphocholine and the capsular polysaccharides [L. S. McDaniel et al., *J. Exp. Med.*, 160, pp. 386–397 (1984); R. M. Krause, *Adv. Immunol.*, 12, pp. 1–56 (1970); D. G. Braun et al., *J. Exp. Med.*, 129, pp. 809–830 (1969)]. In a study using X-linked immunodeficient mice, which respond poorly to carbohydrate antigens and to phosphocholine, but make relatively normal responses to protein antigens, the frequency for obtaining monoclonal antibodies reactive with pneumococcal protein antigens was less than 10%, thus suggesting that *S. pneumoniae* proteins are poor immunogens [McDaniel et al., supra].

Heat shock or stress proteins ("HSPs") are among the most highly conserved and abundant proteins found in nature [F. C. Neidhardt et al., *Ann. Rev. Genet.*, 18, pp. 295–329 (1984); S. Lindquist, *Ann. Rev. Biochem.*, 55, pp. 1151–1191 (1986)]. They are produced by all cells in response to various physiological and nonphysiological stimuli. The heat shock response, in which a sudden increase in temperature induces the synthesis of HSPs, is the best studied of the stress responses. Other environmental conditions such as low pH, iron deficiency and hydrogen peroxyde can also induce HSPs. The HSPs have been defined by their size, and members of hsp90, hsp70, and hsp60 families are among the major HSPs found in all prokaryotes and eukaryotes. These proteins fulfill a variety of chaperon functions by aiding protein folding and assembly and assisting translocation across membranes [C. Georgopoulos and W. J. Welch, *Ann. Rev. Cell. Biol.*, 9, pp. 601–634 (1993); D. Ang et al., *J. Biol. Chem.*, 266, pp. 24233–24236 (1991)]. As molecular chaperons and possibly via other mechanisms, HSPs are likely involved in protecting cells from the deleterious effects of stress. The fact that several virulence factors are regulated by environmental conditions suggests a role for HSPs in microbial pathogenicity [J. J. Mekalanos, *J. Bacteriol.*, 174, pp. 1–7 (1992); P. J. Murray and R. A. Young, *J. Bacteriol.*, 174, pp. 4193–4196 (1992)]. In that respect, recent studies on Salmonella species suggest that the stress response might be critically linked to the ability of intracellular pathogens to initiate and sustain an infection [N. A. Buchmeir and F. Heffron, *Science*, 248, pp. 730–732 (1990); K. Z. Abshire and F. C. Neidhardt, *J. Bacteriol.*, 175, pp. 3734–3743 (1993); B. B. Finlay et al., *Science*, 243, pp. 940–943 (1989)]. Others have demonstrated that lysteriolysin, an essential virulence factor in *L. monocytogenes*, is induced under heat shock conditions [Z. Sokolovic and W. Goebel, *Infect. Immun.*, 57, pp. 295–298 (1989)].

Evidence is now accumulating that HSPs are major antigens of many pathogens. Members of the hsp60 family, also called GroEL-related proteins for their similarity to the *E. coli* GroEL protein, are major antigens of a variety of bacterial pathogens including *Mycobacterium leprae* and *Mycobacterium tuberculosis* [D. Young et al., *Proc. Natl. Acad. Sci. USA*, 85, pp. 4267–4270 (1988)], *Legionella pneumophila* [B. B. Plikaytis et al., *J. Clin. Microbiol.*, 25, pp. 2080–2084 (1987)], *Borrelia burgdorferi* [B. J. Luft et al., *J. Immunol.*, 146, pp. 2776–2782 (1991)], and *Chlamydia trachomatis* [E. A. Wagar et al., *J. Infect. Dis.*, 162, pp. 922–927 (1990)]. This antigen is a homolog of the ubiquitous "common antigen", and is believed to be present in every bacterium [J. E. Thole et al., *Microb. Pathogen.*, 4, pp. 71–83 (1988). Antibodies to the members of the hsp70 family, or DnaK-related proteins, have also been described for several bacterial and parasitic infections [Young et al., supra; Luft et al., supra; D. M. Engman et al., *J. Immunol.*, 144, pp. 3987–3991 (1990); N. M. Rothstein et al., *Molec. Biochem. Parasitol.*, 33, pp. 229–235 (1989); V. Nussenzweig and R. S. Nussenzweig, *Adv. Immunol.*, 45, pp. 283–334 (1989)]. HSPs can elicit strong B- and T- cell responses and it was shown that 20% of the CD4+ T-lymphocytes from mice inoculated with *M. tuberculosis* were reactive to the hsp60 protein alone [S. H .E. Kaufman et al., *Eur. J. Immunol.*, 17, pp. 351–357 (1987)]. Similarly, 7 out of a collection of 24 monoclonal antibodies to *M. leprae* proteins recognized determinants on hsp60 [H. D. Engers et al., *Infect. Immun.*, 48, pp. 603–605 (1985)]. It seems that the immune response to stress proteins might play an important role in protection against infection. Consistent with that is the demonstration that antibodies and T cells reactive with microbial HSPs can exhibit neutralizing and protective activities [A. Noll et al., *Infect. Immun.*, 62, pp. 2784–2791 (1994); and S. L. Danilition et al., *Infect. Immun.*, 58, pp. 189–196 (1990)]. The immunological properties of stress proteins make them attractive as vaccine components and several HSPs are presently being considered for preventing microbial infection and treating cancer. So far, however, studies have focused on intracellular pathogens such as Mycobacteria, Salmonella, Chlamydia and several parasites. Information concerning the heat shock protein antigens in extracellular gram-positive bacteria is far less documented. In *S. pneumoniae*, neither the heat shock proteins nor their gene structure has been identified.

DISCLOSURE OF THE INVENTION

The present invention addresses the problems referred to above by providing a novel heat shock protein from *S. pneumoniae*, and immunologically related polypeptides. Also provided are DNA sequences that code for the foregoing polypeptides, vectors containing the polypeptides, unicellular hosts transformed with those vectors, and a process for making substantially pure, recombinant polypeptides. Also provided are antibodies specific to the foregoing polypeptides. The polypeptides, DNA sequences and antibodies of this invention provide the basis for novel methods and pharmaceutical compositions for the detection, prevention and treatment of disease.

The novel heat shock protein is the approximately 72 kDa heat shock protein of *Streptococcus pneumoniae* ("HSP72") (SEQ ID NO:5), including analogues, homologues, and derivatives thereof, and fragments of the foregoing polypeptides containing at least one immunogenic epitope. Preferred fragments of HSP72 include the C-terminal 169-residue fragment ("IC-169") (residues 439–607, SEQ ID NO:5), and smaller fragments consisting of peptide epitopes within the C-169 region. Particularly preferred fragments within the C-169 region of HSP72 include the peptide sequences GFDAERDAAQAALDD (residues 527–541 of SEQ ID NO:5) and AEGAQATGNAGDDVV (residues 586–600 of SEQ ID NO:5), which are exclusive to HSP72.

Preferred antibodies of this invention are the F1-Pn3.1, F2-Pn3.2, F2-Pn3.3and F2-Pn3.4 monoclonal antibodies ("MAbs"), which are specific to HSP72.

The preferred polypeptides and antibodies of this invention provide the basis for novel methods and pharmaceutical compositions for the detection, prevention and treatment of pneumococcal diseases.

C.). Lane 2 contains non heat-shocked cell lysates (37° C.). Panel B depicts a fluorogram of the immunoblot shown in panel A.

Figure 8:
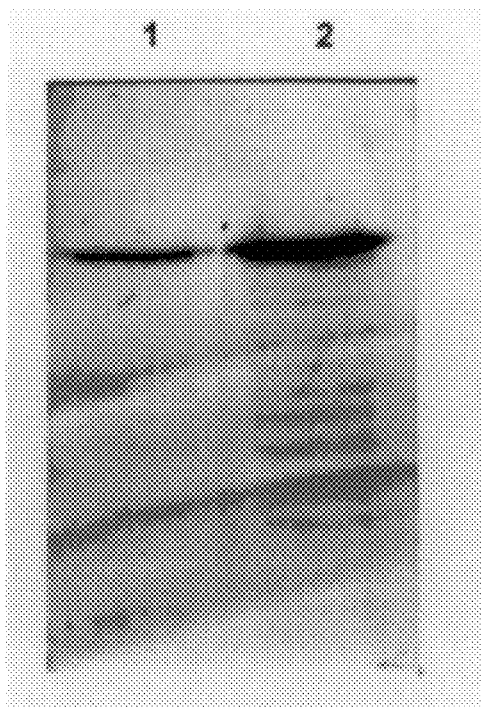

FIG. 8 depicts a Western Blot, which shows subcellular localization of S. pneumoniae HSP72. Sample containing 15 μg protein of membrane fraction (lane 1) and cytoplasmic fraction (lane 2) of S. pneumoniae were electrophoresced on SDS-PAGE transferred to nitrocellulose and probed with MAb F1-Pn3.1.

Figure 9:
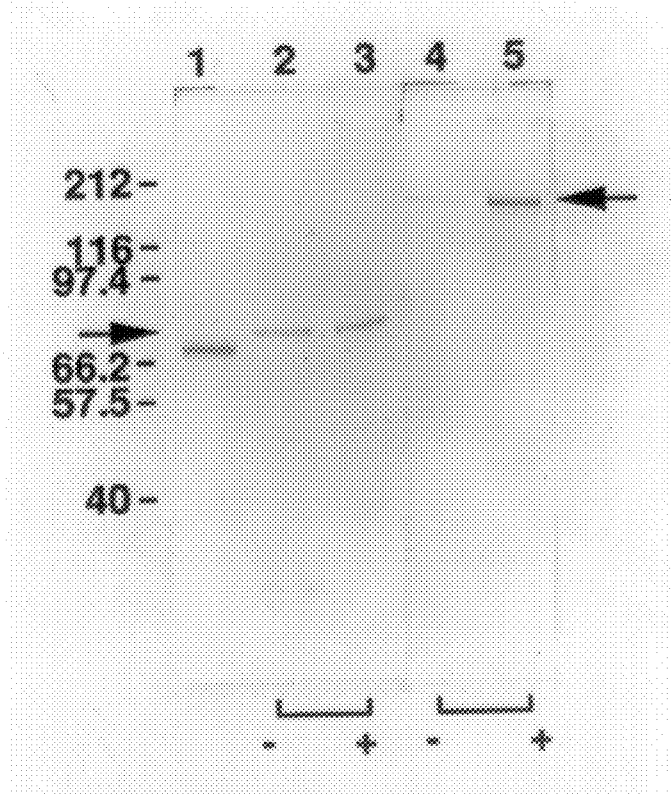

FIG. 9 is a photograph of an immunoblot showing the reactivity of recombinant fusion proteins containing the C-169 region of S. pneumoniae HSP72 with MAb F1-Pn3.1. Lane 1 contains whole cell extracts from S. pneumoniae strain 64 probed with HSP72-specific MAb F1-Pn3.1. Lanes 2 and 3 contain phage lysates from E. coli infected with λJBD17 cultured in the presence (+) or absence (-) of IPTG and probed with HSP72-specific MAb F1-Pn3.1. Lanes 4 and 5 contain phage lysates from E. coli infected with λJBD7 cultured in the presence (+) or absence (-) of IPTG and probed with HSP72-specific MAb F1-Pn3.1. Molecular mass markers are shown to the left. The positions of the 74 kDa- and 160 kDA-reactive proteins are shown on the left and on the right, respectively.

Figure 10:
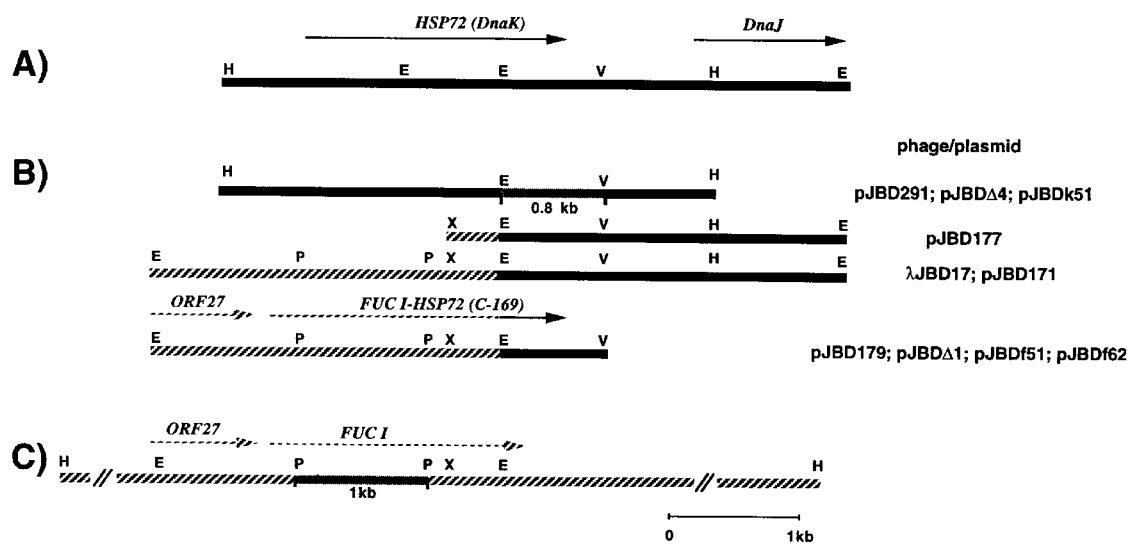

FIG. 10 is a schematic representation of the restriction map of the HSP72 (DnaK) and Fuc loci and inserts of recombinant clones. The relationships between DNA fragments are shown with respect to each other. FIGS. 10A and 10C illustrate the restriction map of the HSP72 (DnaK) and Fuc loci, respectively. FIG. 10B illustrates the inserts of the various phages and plasmids described in Example 3. H(HindIII); E(EcoRI); V(EcoRV); P(PstI); and X(XhoI) indicate positions of restriction endonuclease sites. DNA fragments on the HSP72/DnaK locus (■); the Fuc locus (▨); and fragments used as probes in the Southern blot analyses (▩) are indicated.

Figure 11:
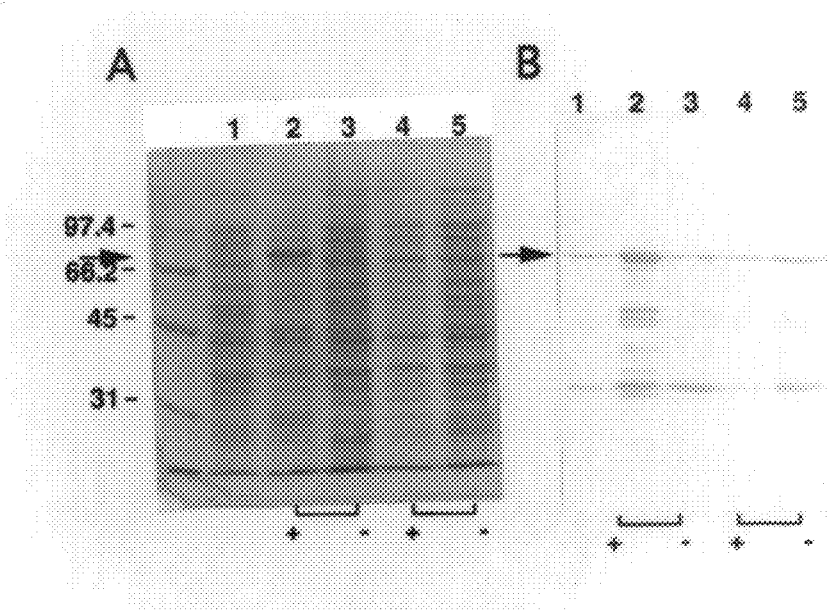

FIG. 11 depicts the SDS-PAGE and Western blot analyses of the recombinant 74 KDa protein. Whole cell extracts from E. coli transformed with plasmids pJBD179 (lane 1), pJBDf51 (lanes 2 and 3) and pJBDf62 (lane 4 and 5) and cultured in presence (+) or absence (-) of IPTG were subjected to 10% polyacrylamide gel electrophoresis. The proteins were then visualized by Coomassie Blue staining (A) or Western blotting (B) using HSP-specific MAb F1-Pn3.1. Molecular mass markers in kilodaltons are shown to the left. The arrow at the left-hand side of each panel marks the 74 KDa protein.

Figure 12:

FIG. 12 depicts the detection of native and recombinant HSP72 antigens by Western blot analysis. Whole cell lysates from E. coli transformed with plasmids pJBDk51 (lanes 1 and 3) and pJBD291 (lane 2) and cell lysates from S. pneumoniae strain 64 (lane 4) were subjected to 10% polyacrylamide gel electrophoresis and were electrotransferred to nitrocellulose. The immunoblot was probed with HSP72-specific MAb F1-Pn3.1.

FIGS. 13A–13D depict a comparison of the predicted amino acid sequence of the S. pneumoniae HSP72 open reading frame (HSP72 SPNEU) with those previously reported for the following HSP70/DnaK proteins: ECOLI, Escherichia coli; BORBU, Borrelia burgdorferi; BRUOV, Brucella ovis; CHLPN, Chlamydia pneumonia; BACME, Bacillus megatorium; BACSU, Bacillus subtilis; STAAU, Staphylococcus aureus; LACLA, Lactococcus lactis; and MYCTU, Mycobacterium tuberculosis. Only mismatched amino acids are indicated. Identical and conserved amino acids are boxed and shadowed, respectively.

Figure 14:
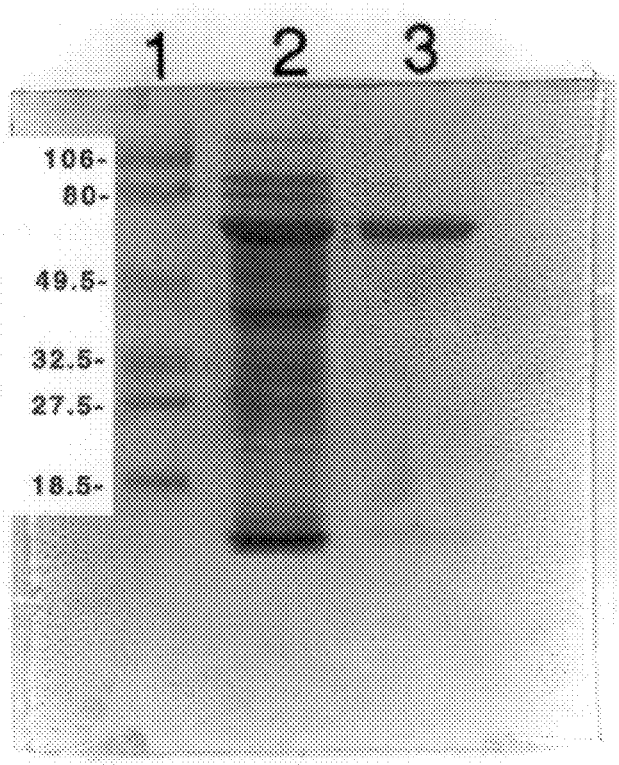

FIG. 14 depicts a photograph of an SDS-PAGE, which shows the recombinant S. pneumoniae HSP72 purified by affinity chromatography. Supernatant fractions from E. coli (pJBDk51) lysates (lane 2) and 20 μg of immunoaffinity-purified HSP72$_{rec}$ (lane 3) were subjected to 10% polyacrylamide gel electrophoresis. The proteins were then visualized by Coomassie Blue staining. Lane 1 shows the migration of molecular mass markers (106 kDa, 80 kDa, 49.5 kDa, 32.5 kDa, 27.5 kDa and 18.5 kDa).

Figure 15:
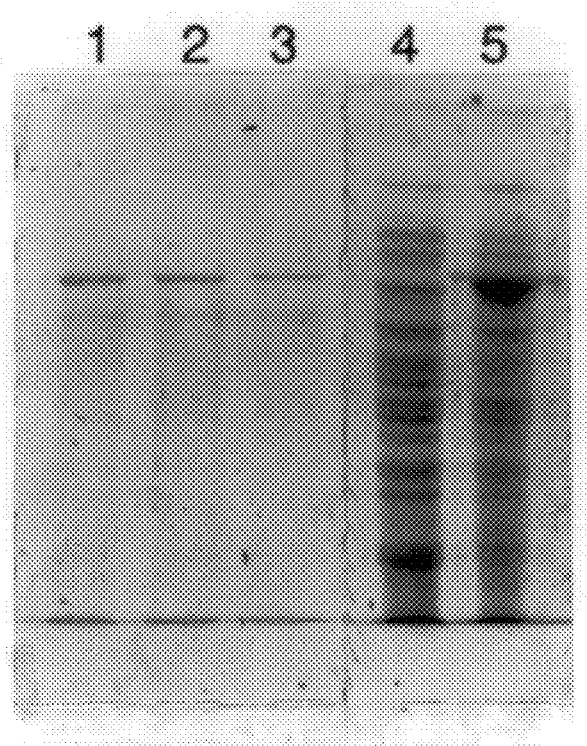

FIG. 15 depicts a photograph of SDS-PAGE, which shows the recombinant S. pneumoniae C-169 fragment purified by solubilization of inclusion bodies. Various amounts of purified C-169 protein (lane 1, 5 μg; lane 2, 2.5 μg; and lane 3, 1 μg) and whole cell lysates from E. coli transformed with plasmids pDELTA1 (lane 4) and pJBDΔ1 (lane 5) were subjected to 10% polyacrylamide gel electrophoresis. The proteins were then visualized by Coomassie Blue staining.

Figure 16:
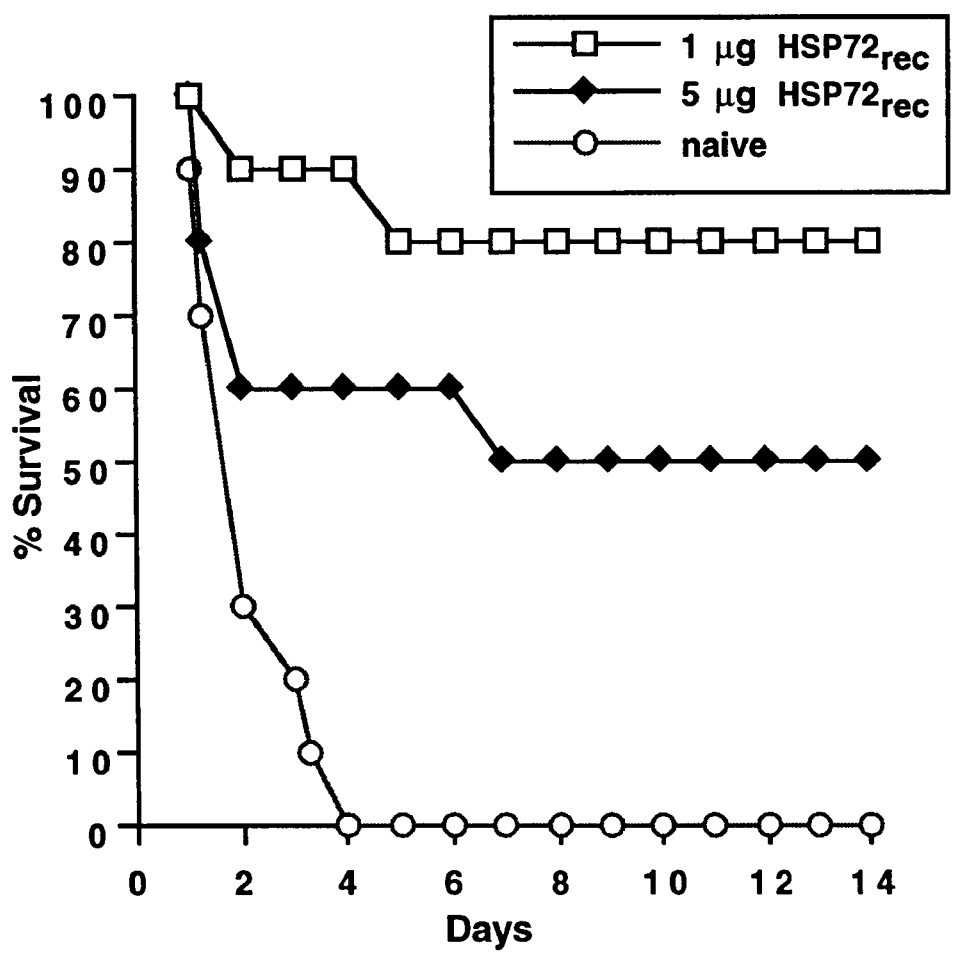

FIG. 16 is a graphical depiction of the survival curve of Balb/c mice protected from S. pneumoniae infection by immunization with HSP72$_{rec}$. Data are presented as the per cent (%) survival over a period of 14 days for a total of 10 mice per experimental group.

Figure 17:
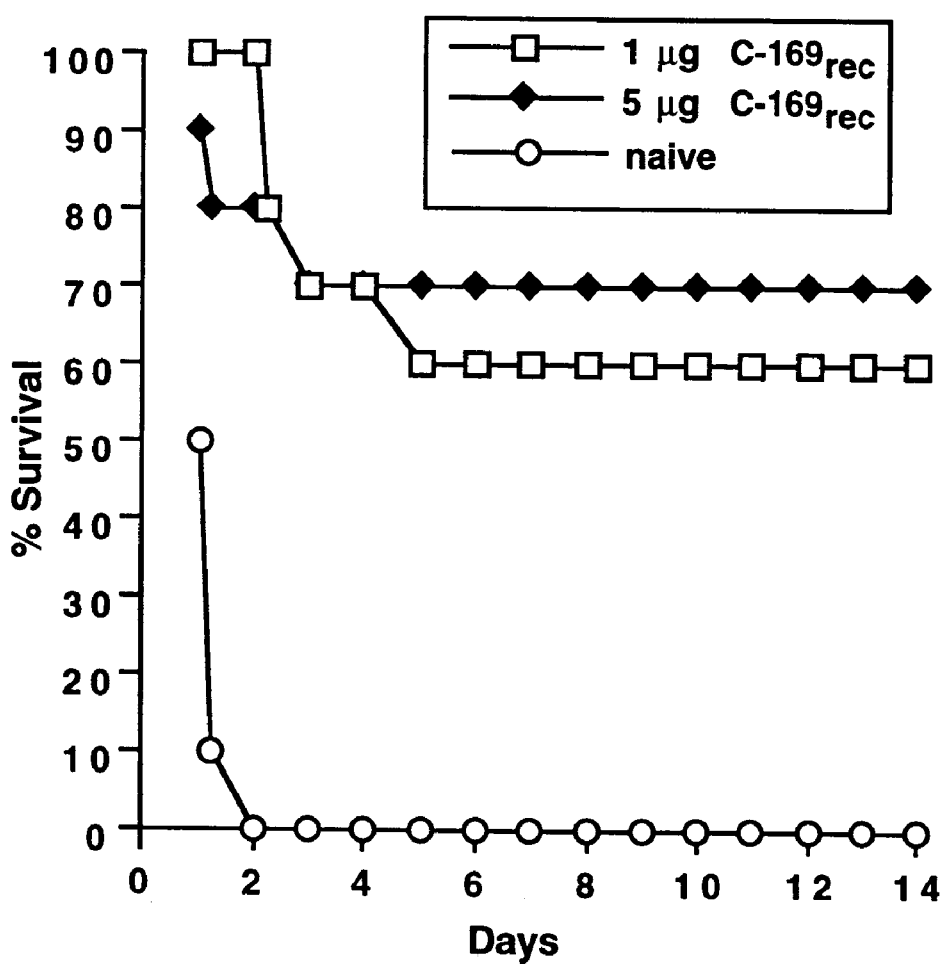

FIG. 17 is a graphical depiction of the survival curve of Balb/c mice protected from S. pneumoniae infection by immunization with C-169$_{rec}$. Data are presented as the per cent (%) survival over a period of 14 days for a total of 10 mice per experimental group.

DETAILED DESCRIPTION OF THE INVENTION

According to one aspect of the invention, we provide a novel heat shock protein of S. pneumoniae, and analogues, homologues, derivatives and fragments thereof, containing at least one immunogenic epitope. As used herein, a "heat shock protein" is a naturally occurring protein that exhibits preferential transcription during heat stress conditions. The heat shock protein according to the invention may be of natural origin, or may be obtained through the application of recombinant DNA techniques, or conventional chemical synthesis techniques.

As used herein, "immunogenic" means having the ability to elicit an immune response. The novel heat shock protein of this invention is characterized by its ability to elicit a protective immune response against lethal S. pneumoniae infection.

The invention particularly provides a Streptoccus pneumoniae heat shock protein of approximately 72 KDa ("HSP72"), having the deduced amino acid sequence of SEQ ID NO:5, and analogues, homologues, derivatives and fragments thereof, containing at least one immunogenic epitope.

As used herein, "analogues" of HSP72 are those S. pneumoniae proteins wherein one or more amino acid residues in the HSP72 amino acid sequence (SEQ ID NO:5) is replaced by another amino acid residue, providing that the overall functionality and immunogenic properties of the analogue protein are preserved. Such analogues may be naturally occurring, or may be produced synthetically or by recombinant DNA technology, for example, by mutagenesis of the HSP72 sequence. Analogues of HSP72 will possess at least one antigen capable of eliciting antibodies that react with HSP72.

As used herein, "homologues" of HSP72 are proteins from Streptococcal species other than pneumoniae, or genera other than Streptococcus wherein one or more amino acid residues in the HSP72 amino acid sequence (SEQ ID NO:5) is replaced by another amino acid residue, providing that the overall functionality and immunogenic properties of the homologue protein are preserved. Such homologues may be naturally occurring, or may be produced synthetically or by recombinant DNA technology. Homologues of HSP72 will possess at least one antigen capable of eliciting antibodies that react with HSP72, e.g. *Enterococcus faecalis*.

As used herein, a "derivative" is a polypeptide in which one or more physical, chemical, or biological properties has been altered. Such alterations include, but are not limited to: amino acid substitutions, modifications, additions or deletions; alterations in the pattern of lipidation, glycolsylation or phosphorylation; reactions of free amino, carboxyl, or hydroxyl side groups of the amino acid residues present in the polypeptide with other organic and non-organic molecules; and other alterations, any of which may result in changes in primary, secondary or tertiary structure.

The "fragments" of this invention will have at least one immunogenic epitope. An "immunogenic epitope" is an epitope that is instrumental in eliciting an immune response. The preferred fragments of this invention will elicit an immune response sufficient to prevent or lessen the severity of infection, e.g., *S. pneumoniae* infection. Preferred fragments of HSP72 include the C-terminal 169-residue fragment ("C-169") (SEQ ID NO:5, residues 439–607), and smaller fragments consisting of peptide epitopes within the C-169 region. Particularly preferred fragments within the C-169 region of HSP72 include the peptide sequences GFDAERDAAQAALDD (residues 527–541 of SEQ ID NO:5) and AEGAQATGNAGDDVV (residues 586–600 of SEQ ID NO:5), which are exclusive to HSP72.

In a further aspect of the invention, we provide polypeptides that are immunologically related to HSP72. As used herein, "immunologically related" polypeptides are characterized by one or more of the following properties:

(a) they are immunologically reactive with antibodies generated by infection of a mammalian host with *Streptococcus pneumoniae* cells, which antibodies are immunologically reactive with HSP72 (SEQ ID NO:5);

(b) they are capable of eliciting antibodies that are immunologically reactive with HSP72 (SEQ ID NO:5);

(c) they are immunologically reactive with antibodies elicited by immunization of a mammal with HSP72 (SEQ ID NO:5). By definition, analogues, homologues and derivatives of HSP72 are immunologically related polypeptides. Moreover, all immunologically related polypeptides contain at least one HSP72 antigen. Accordingly, "HSP72 antigens" may be found in HSP72 itself, or in immunologically related polypeptides.

As used herein, "related bacteria" are bacteria that possess antigens capable of eliciting antibodies that react with HSP72. Examples of related bacteria include *Streptococcus pyogenes, Streptococcus mutans, Streptococcus sanguis* and *Enterococcus faecalis*.

It will be understood that by following the examples of this invention, one of skill in the art may determine without undue experimentation whether a particular analogue, homologue, derivative, immunologically related polypeptide, or fragment would be useful in the diagnosis, prevention or treatment of disease. Useful polypeptides and fragments will elicit antibodies that are immunoreactive with HSP72 (Example 4). Preferably, useful polypeptides and fragments will demonstrate the ability to elicit a protective immune response against lethal bacterial infection (Example 5).

Also included are polymeric forms of the polypeptides of this invention. These polymeric forms include, for example, one or more polypeptides that have been crosslinked with crosslinkers such as avidin/biotin, gluteraldehyde or dimethylsuberimidate. Such polymeric forms also include polypeptides containing two or more tandem or inverted contiguous protein sequences, produced from multicistronic mRNAs generated by recombinant DNA technology.

This invention provides substantially pure HSP72 and immunologically related polypeptides. The term "substantially pure" means that the polypeptides according to the invention, and the DNA sequences encoding them, are substantially free from other proteins of bacterial origin. Substantially pure protein preparations may be obtained by a variety of conventional processes, for example the procedures described in Examples 3 and 5.

In another aspect, this invention provides, for the first time, a DNA sequence coding for a heat shock protein of *S. pneumoniae*, specifically, HSP72 (SEQ ID NO:4, nucleotides 682–2502).

The DNA sequences of this invention also include DNA sequences coding for polypeptide analogues and homologues of HSP72, DNA sequences coding for immunologically related polypeptides, DNA sequences that are degenerate to any of the foregoing DNA sequences, and fragments of any of the foregoing DNA sequences. It will be readily appreciated that a person of ordinary skill in the art will be able to determine the DNA sequence of any of the polypeptides of this invention, once the polypeptide has been identified and isolated, using conventional DNA sequencing techniques.

Oligonucleotide primers and other nucleic acid probes derived from the genes encoding the polypeptides of this invention may also be used to isolate and clone other related proteins from *S. pneumoniae* and related bacteria which may contain regions of DNA bacteria that are homologous to the DNA sequences of this invention. In addition, the DNA sequences of this invention may be used in PCR reactions to detect the presence of *S. pneumoniae* or related bacteria in a biological sample.

The polypeptides of this invention may be prepared from a variety of processes, for example by protein fractionization from appropriate cell extracts, using conventional separation techniques such as ion exchange and gel chromatography and electrophoresis, or by the use of recombinant DNA techniques. The use of recombinant DNA techniques is particularly suitable for preparing substantially pure polypeptides according to the invention.

Thus according to a further aspect of the invention, we provide a process for the production of HSP72, immunologically related polypeptides, and fragments thereof, comprising the steps of (1) culturing a unicellular host organism transformed with a vector containing a DNA sequence coding for said polypeptide or fragment and one or more expression control sequences operatively linked to the DNA sequence, and (2) recovering a substantially pure polypeptide or fragment.

As is well known in the art, in order to obtain high expression levels of a transfected gene in a host, the gene must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an expression marker useful in the eukaryotic expression host.

The DNA sequences encoding the polypeptides of this invention may or may not encode a signal sequence. If the expression host is eukaryotic, it generally is preferred that a signal sequence be encoded so that the mature protein is secreted from the eukaryotic host.

An amino terminal methionine may or may not be present on the expressed polypeptides of this invention. If the terminal methionine is not cleaved by the expression host, it may, if desired, be chemically removed by standard techniques.

A wide variety of expression host/vector combinations may be employed in expressing the DNA sequences of this invention. Useful expression vectors for eukaryotic hosts include, for example, vectors comprising expression control sequences from SV40, bovine papilloma virus, adenovirus, adeno-associated virus, cytomegalovirus, and retroviruses. Useful expression vectors for bacterial hosts include bacterial plasmids, such as those from *E. coli*, including pBluescript, pGEX2T, pUC vectors, col E1, pCR1, pBR322, pMB9 and their derivatives, wider host range plasmids, such as RP4, phage DNAs, e.g., the numerous derivatives of phage lambda, e.g. λGT10 and λGT11, NM989, and other DNA phages, such as M13 and filamentous single stranded DNA phages. Useful expression vectors for yeast cells include the $2\mu$ plasmid and derivatives thereof. Useful vectors for insect cells include pVL 941.

In addition, any of a wide variety of expression control sequences may be used in these vectors to express the DNA sequences of this invention. Useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the T3 and T7 promoters the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast alpha-mating system and other constitutive and inducible promoter sequences known to control the expression of genes of prokaryotic or eukaryotic cells or their viruses, and various combinations thereof. The T7 RNA polymerase promoter Φ10 is particularly useful in the expression of HSP72 in *E. coli* (Example 3).

Host cells transformed with the foregoing vectors form a further aspect of this invention. A wide variety of unicellular host cells are useful in expressing the DNA sequences of this invention. These hosts may include well known eukaryotic and prokaryotic hosts, such as strains of *E. coli*, Pseudomonas, Bacillus, Streptomyces, fungi, yeast, insect cells such as *Spodoptera frugiperda* (SF9), animal cells such as CHO and mouse cells, African green monkey cells such as COS 1, COS 7, BSC 1, BSC 40, and BMT 10, human cells, and plant cells in tissue culture. Preferred host organisms include bacteria such as *E. coli* and *B. subtilis*, and mammalian cells in tissue culture.

It should of course be understood that not all vectors and expression control sequences will function equally well to express the DNA sequences of this invention. Neither will all hosts function equally well with the same expression system. However, one of skill in the art may make a selection among these vectors, expression control sequences and hosts without undue experimentation and without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the DNA sequences of this invention, particularly as regards potential secondary structures. Unicellular hosts should be selected by consideration of their compatibility with the chosen vector, the toxicity of the product coded for by the DNA sequences of this invention, their secretion characteristics, their ability to fold the protein correctly, their fermentation or culture requirements, and the ease of purification from them of the products coded for by the DNA sequences of this invention. Within these parameters, one of skill in the art may select various vector/expression control sequence/host combinations that will express the DNA sequences of this invention on fermentation or in large scale animal culture.

The polypeptides encoded by the DNA sequences of this invention may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

In addition, the polypeptides of this invention may be generated by any of several chemical techniques. For example, they may be prepared using the solid-phase synthetic technique originally described by R. B. Merrifield, "Solid Phase Peptide Synthesis. I. The Synthesis Of A Tetrapeptide", *J. Am. Chem. Soc.*, 83, pp. 2149–54 (1963), or they may be prepared by synthesis in solution. A summary of peptide synthesis techniques may be found in E. Gross & H. J. Meinhofer, 4 The Peptides: Analysis, Synthesis, Biology; Modern Techniques Of Peptide And Amino Acid Analysis, John Wiley & Sons, (1981) and M. Bodanszky, Principles Of Peptide Synthesis, Springer-Verlag (1984).

The preferred compositions and methods of this invention comprise polypeptides having enhanced immunogenicity. Such polypeptides may result when the native forms of the polypeptides or fragments thereof are modified or subjected to treatments to enhance their immunogenic character in the intended recipient. Numerous techniques are available and well known to those of skill in the art which may be used, without undue experimentation, to substantially increase the immunogenicity of the polypeptides herein disclosed. For example, the polypeptides may be modified by coupling to dinitrophenol groups or arsanilic acid, or by denaturation with heat and/or SDS. Particularly if the polypeptides are small polypeptides synthesized chemically, it may be desirable to couple them to an immunogenic carrier. The coupling of course, must not interfere with the ability of either the polypeptide or the carrier to function appropriately. For a review of some general considerations in coupling strategies, see *Antibodies, A Laboratory Manual*, Cold Spring Harbor Laboratory, ed. E. Harlow and D. Lane (1988). Useful immunogenic carriers are well known in the art. Examples of such carriers are keyhole limpet hemocyanin (KLH); albumins such as bovine serum albumin (BSA) and ovalbumin, PPD (purified protein derivative of tuberculin); red blood cells; tetanus toxoid; cholera toxoid; agarose beads; activated carbon; or bentonite.

Modification of the amino acid sequence of the polypeptides disclosed herein in order to alter the lipidation state is also a method which may be used to increase their immunogenicity and biochemical properties. For example, the polypeptides or fragments thereof may be expressed with or without the signal sequences that direct addition of lipid moieties.

In accordance with this invention, derivatives of the polypeptides may be prepared by a variety of methods, including by in vitro manipulation of the DNA encoding the native polypeptides and subsequent expression of the modified DNA, by chemical synthesis of derivatized DNA sequences, or by chemical or biological manipulation of expressed amino acid sequences.

For example, derivatives may be produced by substitution of one or more amino acids with a different natural amino acid, an amino acid derivative or non-native amino acid, conservative substitution being preferred, e.g., 3-methylhistidine may be substituted for histidine, 4-hydroxyproline may be substituted for proline, 5-hydroxylysine may be substituted for lysine, and the like.

Causing amino acid substitutions which are less conservative may also result in desired derivatives, e.g., by causing changes in charge, conformation and other biological properties. Such substitutions would include for example, substitution of a hydrophilic residue for a hydrophobic residue, substitution of a cysteine or proline for another residue, substitution of a residue having a small side chain for a residue having a bulky side chain or substitution of a residue having a net positive charge for a residue having a net negative charge. When the result of a given substitution cannot be predicted with certainty, the derivatives may be readily assayed according to the methods disclosed herein to determine the presence or absence of the desired characteristics.

The polypeptides may also be prepared with the objective of increasing stability or rendering the molecules more amenable to purification and preparation. One such technique is to express the polypeptides as fusion proteins comprising other *S. pneumoniae* or non-*S. pneumoniae* sequences. It is preferred that the fusion proteins comprising the polypeptides of this invention be produced at the DNA level, e.g., by constructing a nucleic acid molecule encoding the fusion, transforming host cells with the molecule, inducing the cells to express the fusion protein, and recovering the fusion protein from the cell culture. Alternatively, the fusion proteins may be produced after gene expression according to known methods. An example of a fusion protein according to this invention is the FucI/HSP72 (C-169) protein of Example 3, infra.

The polypeptides of this invention may also be part of larger multimeric molecules which may be produced recombinantly or may be synthesized chemically. Such multimers may also include the polypeptides fused or coupled to moieties other than amino acids, including lipids and carbohydrates.

The polypeptides of this invention are particularly well-suited for the generation of antibodies and for the development of a protective response against disease. Accordingly, in another aspect of this invention, we provide antibodies, or fragments thereof, that are immunologically reactive with HSP72. The antibodies of this invention are either elicited by immunization with HSP72 or an immunologically related polypeptide, or are identified by their reactivity with HSP72 or an immunologically related polypeptide. It should be understood that the antibodies of this invention are not intended to include those antibodies which are normally elicited in an animal upon infection with naturally occurring *S. pneumoniae* and which have not been removed from or altered within the animal in which they were elicited.

The antibodies of this invention may be intact immunoglobulin molecules or fragments thereof that contain an intact antigen binding site, including those fragments known in the art as F(v), Fab, Fab' and F(ab')2. The antibodies may also be genetically engineered or synthetically produced. The antibody or fragment may be of animal origin, specifically of mammalian origin, and more specifically of murine, rat or human origin. It may be a natural antibody or fragment, or if desired, a recombinant antibody or fragment. The antibody or antibody fragments may be of polyclonal, or preferably, of monoclonal origin. They may be specific for a number of epitopes but are preferably specific for one. Specifically preferred are the monoclonal antibodies F1-Pn3.1, F2-Pn3.2, F2-Pn3.3 and F2-Pn3.4 of Example 2, infra. One of skill in the art may use the polypeptides of this invention to produce other monoclonal antibodies which could be screened for their ability to confer protection against *S. pneumoniae* or *S. pneumoniae*-related bacterial infection when used to immunize naive animals. Once a given monoclonal antibody is found to confer protection, the particular epitope that is recognized by that antibody may then be identified. Methods to produce polyclonal and monoclonal antibodies are well known to those of skill in the art. For a review of such methods, see *Antibodies, A Laboratory Manual*, supra, and D. E. Yelton, et al., *Ann. Rev. of Biochem.*, 50, pp. 657–80 (1981). Determination of immunoreactivity with a polypeptide of this invention may be made by any of several methods well known in the art, including by immunoblot assay and ELISA.

An antibody of this invention may also be a hybrid molecule formed from immunoglobulin sequences from different species (e.g., mouse and human) or from portions of immunoglobulin light and heavy chain sequences from the same species. It may be a molecule that has multiple binding specificities, such as a bifunctional antibody prepared by any one of a number of techniques known to those of skill in the art including: the production of hybrid hybridomas; disulfide exchange; chemical cross-linking; addition of peptide linkers between two monoclonal antibodies; the introduction of two sets of immunoglobulin heavy and light chains into a particular cell line; and so forth.

The antibodies of this invention may also be human monoclonal antibodies, for example those produced by immortalized human cells, by SCID-hu mice or other non-human animals capable of producing "human" antibodies, or by the expression of cloned human immunoglobulin genes.

In sum, one of skill in the art, provided with the teachings of this invention, has available a variety of methods which may be used to alter the biological properties of the antibodies of this invention including methods which would increase or decrease the stability or half-life, immunogenicity, toxicity, affinity or yield of a given antibody molecule, or to alter it in any other way that may render it more suitable for a particular application.

The polypeptides, DNA sequences and antibodies of this invention are useful in prophylactic, therapeutic and diagnostic compositions for preventing, treating and diagnosing disease.

Standard immunological techniques may be employed with the polypeptides and antibodies of this invention in order to use them as immunogens and as vaccines. In particular, any suitable host may be injected with a pharmaceutically effective amount of polypeptide to generate monoclonal or polyvalent antibodies or to induce the development of a protective immunological response against disease. Preferably, the polypeptide is HSP72 (SEQ ID NO:5) or fragments thereof.

As used herein, a "pharmaceutically effective amount" of a polypeptide or of an antibody is the amount that, when administered to a patient, elicits an immune response that is effective to prevent or lessen the severity of *S. pneumonia* or related bacterial infections.

The administration of the polypeptides or antibodies of this invention may be accomplished by any of the methods described in Example 6, infra, or by a variety of other standard procedures. For a detailed discussion of such techniques, see *Antibodies, A Laboratory Manual*, Cold Spring Harbor Laboratory, ed. E. Harlow and D. Lane (1988). Preferably, if a polypeptide is used, it will be administered with a pharmaceutically acceptable adjuvant, such as complete or incomplete Freund's adjuvant, RIBI (muramyl dipeptides) or ISCOM (immunostimulating complexes). Preferably, the composition will include a water-in-oil emulsion or aluminum hydroxide as adjuvant and will be administered intramuscularly. The vaccine composition may be administered to the patient at one time or over a series of treatments. The most effective mode of administration and dosage regimen will depend upon the level of immunogenicity, the particular composition and/or adjuvant used for treatment, the severity and course of the expected infection, previous therapy, the patient's health status and response to immunization, and the judgment of the treating physician. For example, in an immunocompetent patient, the more highly immunogenic the polypeptide, the lower the dosage and necessary number of immunizations. Similarly, the dosage and necessary treatment time will be lowered if the polypeptide is administered with an adjuvant.

Generally, the dosage will consist of an initial injection, most probably with adjuvant, of about 0.01 to 10 mg, and preferable 0.1 to 1.0 mg, HSP72 antigen per patient, followed most probably by one or maybe more booster injections. Preferably, boosters will be administered at about 1 and 6 months after the initial injection.

Any of the polypeptides of this invention may be used in the form of a pharmaceutically acceptable salt. Suitable acids and bases which are capable of forming salts with the polypeptides of the present invention are well known to those of skill in the art, and include inorganic and organic acids and bases.

To screen the polypeptides and antibodies of this invention for their ability to confer protection against diseases caused by *S. pneumoniae* or related bacteria, or their ability to lessen the severity of such infection, one of skill in the art will recognize that a number of animal models may be used. Any animal that is susceptible to infection with *S. pneumoniae* or related bacteria may be useful. The Balb/c mice of Example 5, infra, are the preferred animal model for active immunoprotection screening, and the severe-combined immunodeficient mice of Example 5 are the preferred animal model for passive screening. Thus, by administering a particular polypeptide or antibody to these animal models, one of skill in the art may determine without undue experimentation whether that polypeptide or antibody would be useful in the methods and compositions claimed herein.

According to another embodiment of this invention, we describe a method which comprises the steps of treating a patient with a vaccine comprising a pharmaceutically effective amount of any of the polypeptides of this invention in a manner sufficient to prevent or lessen the severity, for some period of time, of *S. pneumoniae* or related bacterial infection. Again, the preferred polypeptide for use in such methods is HSP72, or fragments thereof.

The polypeptides, DNA sequences and antibodies of this invention may also form the basis for diagnostic methods and kits for the detection of pathogenic organisms. Several diagnostic methods are possible. For example, this invention provides a method for the detection of *Streptococcus pneumoniae* or related bacteria in a biological sample comprising the steps of:

(a) isolating the biological sample from a patient;

(b) incubating an antibody of this invention, or fragment thereof with the biological sample to form a mixture; and (c) detecting specifically bound antibody or fragment in the mixture which indicates the presence of *Streptococcus pneumoniae* or related bacteria. Preferable antibodies for use in this method include monoclonal antibodies F1-Pn3.1, F2-Pn3.2, F2-Pn3.3 and F2-Pn3.4.

Alternatively, this invention provides a method for the detection of antibodies specific to *Streptococcus pneumoniae* or related bacteria in a biological sample comprising:

(a) isolating the biological sample from a patient;

(b) incubating a polypeptide of this invention or fragment thereof, with the biological sample to form a mixture; and (c) detecting specifically bound polypeptide in the mixture which indicates the presence of antibodies specific to *Streptococcus pneumoniae* or related bacteria. HSP72 (SEQ ID NO:5), the C-169 fragment thereof (residues 439–607 of SEQ ID NO:5), and peptide fragments GFDAERDAAQAALDD (residues 527–541 of SEQ ID NO:5) and AEGAQATGNAGD-DVW (residues 586–600 of SEQ ID NO:5) are the preferred polypeptide and fragments in the above method for the detection of antibodies.

One of skill in the art will recognize that these diagnostic tests may take several forms, including an enzyme-linked immunosorbent assay (ELISA), a radioimmunoassay or a latex agglutination assay.

The diagnostic agents may be included in a kit which may also comprise instructions for use and other appropriate reagents, preferably a means for detecting when the polypeptide or antibody is bound. For example, the polypeptide or antibody may be labeled with a detection means that allows for the detection of the polypeptide when it is bound to an antibody, or for the detection of the antibody when it is bound to *S. pneumoniae* or related bacteria. The detection means may be a fluorescent labeling agent such as fluorescein isocyanate (FIC), fluorescein isothiocyanate (FITC), and the like, an enzyme, such as horseradish peroxidase (HRP), glucose oxidase or the like, a radioactive element such as $^{125}$I or $^{51}$Cr that produces gamma ray emissions, or a radioactive element that emits positrons which produce gamma rays upon encounters with electrons present in the test solution, such as $^{11}$C, $^{15}$O, or $^{13}$N. Binding may also be detected by other methods, for example via avidin-biotin complexes. The linking of the detection means is well known in the art. For instance, monoclonal antibody molecules produced by a hybridoma may be metabolically labeled by incorporation of radioisotope-containing amino acids in the culture medium, or polypeptides may be conjugated or coupled to a detection means through activated functional groups.

The DNA sequences of this invention may be used to design DNA probes for use in detecting the presence of *Streptococcus pneumoniae* or related bacteria in a biological sample. The probe-based detection method of this invention comprises the steps of:

(a) isolating the biological sample from a patient;

(b) incubating a DNA probe having a DNA sequence of this invention with the biological sample to form a mixture; and (c) detecting specifically bound DNA probe in the mixture which indicates the presence of *Streptococcus pneumoniae* or related bacteria.

The DNA probes of this invention may also be used for detecting circulating nucleic acids in a sample, for example using a polymerase chain reaction, as a method of diagnosing *Streptococcus pneumoniae* or related bacterial infections. The probes may be synthesized using conventional techniques and may be immobilized on a solid phase, or may be labeled with a detectable label. A preferred DNA probe for this application is an oligomer having a sequence complementary to at least about 6 contiguous nucleotides of HSP72 (SEQ ID NO:4, nucleotides 682–2502).

The polypeptides of this invention may also be used to purify antibodies directed against epitopes present on the protein, for example, using immunoaffinity purification of antibodies on an antigen column.

The antibodies or antibody fragments of this invention may be used to prepare substantially pure proteins according to the invention for example, using immunoaffinity purification of antibodies on an antigen column.

EXAMPLES

In order that this invention may be better understood, the following examples are set forth. These examples are for purposes of illustration only, and are not to be construed as limiting the scope of the invention in any manner.

Example 1 describes the identification of HSP72, an immunoreactive heat shock protein according to the invention. Example 2 describes the isolation of monoclonal antibodies against epitopes of HSP72. Example 3 describes the preparation of recombinant HSP72 and fragments of HSP72 according to the invention. Example 4 describes the antigenic specificity and immunoreactivity of monoclonal antibodies directed against HSP72, and the identification of immunologically related proteins according to the invention. Example 5 describes processes for obtaining substantially pure HSP72, and the use of HSP72 or antibodies against it to protect against experimental *S. pneumoniae* infection. Example 6 describes the use of HSP72 antigen in a human vaccine.

Example 1—Identification of Immunoreactive *S. pneumoniae* Heat Shock Proteins

A. Procedures

Unless otherwise noted, the following procedures were used throughout the Examples herein.

1. Bacteria

*S. pneumoniae* strains were provided by the Laboratoire de la Santé Publique du Québec, Sainte-Anne de Bellevue. *S. pneumoniae* strains included type 4 strain 53 and type 6 strain 64. If not specified, *S. pneumoniae* type 6 strain 64 was used. Bacterial strains were grown overnight at 37° C. in 5% $CO_2$ on chocolate agar plates.

2. Antigen Preparations

Various *S. pneumoniae* antigens were prepared for immunization and immunoassays. Heat-killed whole cell antigens were obtained by incubating bacterial suspensions in a water bath prewarmed at 56° C. for 20 minutes. Detergent-soluble proteins were extracted from *S. pneumoniae* as follows. Heat-killed bacteria were suspended in 10 mM Hepes buffer (4-(2-Hydroxyethyl)-1-piperazinethan-sulfonsaure) (Boehringer Mannheim GmbH, Germany) at pH 7.4 and sonicated at 20,000 Kz/second, four times for 30 seconds. Intact cells and large debris were removed by centrifugation at 1,700 g for 20 minutes. The supernatant was collected and centrifuged at 100,000 g for 60 minutes. The pellet was resuspended in 1 ml of Hepes buffer, and 1 ml of 2% N-lauroyl sarcosine (Sigma Chemical Co., St. Louis, Mo.) was added. The mixture was incubated for 30 minutes at room temperature and the detergent-soluble fraction was harvested by centrifugation at 100,000 g for 60 minutes.

3. Heat Shock Treatment

*S. pneumoniae* bacteria (type 4, strain 53 and type 6, strain 64) were resuspended in Eagle's Minimal Essential Medium lacking methionine (ICN Biomedicals Inc., Costa Mesa, Calif.) and supplemented with 1% BIO-X (Quelab Laboratories, Montreal, Canada) for 15 minutes at 37° C. and then divided into fractions of equal volume. The samples were incubated at either 37° C. or 45° C. for 5 minutes and then labeled with 100 μCi/ml [$^{35}$S]methionine (ICN) for 10, 30, or 60 minutes at the respective temperature. The bacteria were harvested and cell extracts were prepared using Tris-HCl lysis buffer as described above, or SDS-PAGE sample buffer.

4. Immunization of Mice

Female Balb/c mice (Charles River Laboratories, St-Constant, Québec, Canada) were immunized with *S. pneumoniae* antigens. Immune sera to *S. pneumoniae* type 6 strain 64 were obtained from mice immunized, at two-week intervals, by subcutaneous injections of $10^7$ heat-killed bacteria or 20 μg of detergent-soluble pneumococcal proteins absorbed to aluminum hydroxide adjuvant (Alhydrogel; Cedarlane Laboratories Ltd., Horny, Ontario, Canada). Blood samples were collected prior to immunization and at seven days following the first and second immunization.

5. SDS-PAGE and Immunoassays

Cell extracts were prepared for SDS-PAGE, Western blot analysis and radioimmunoprecipitation assay by incubating bacterial suspensions in Tris-HCl lysis buffer (50 mM Tris, 150 mM NaCl, 0.1% Na dodecyl sulfate, 0.5% Na deoxycholate, 2% Triton X-100, 100 μg/ml phenylmethylsulfonylfluoride, and 2 μg/ml aprotinin) at pH 8.0 for 30 minutes on ice. Lysed cells were cleared by centrifugation and the supernatants were aliquoted and kept frozen at −70° C.

SDS-PAGE were performed on a 10% polyacrylamide gel according to the method of Laemmli [*Nature*, 227, pp. 680–685 (1970)], using the Mini Protean system (Bio-Rad Laboratories Ltd., Mississauga, Canada). Samples were denatured by boiling for 5 minutes in sample buffer containing 2% 2-mercaptoethanol. Proteins were resolved by staining the polyacrylamide gel with PhastGel Blue R (Pharmacia Biotech Inc., Baie d'Urfé, Canada). The radiolabeled products were visualized by fluorography. Fluorograms were scanned using a laser densitometer.

Immunoblot procedures were performed according to the method of Towbin et al. [*Proc. Natl. Acad. Sci. USA*, 76, pp. 4350–4354 (1979)]. The detection of antigens reactive with antibodies was performed by an indirect antibody immunoassay using peroxidase-labeled anti-mouse immunoglobulins and the o-dianisidine color substrate.

Radioimmunoprecipitation assays were performed as described by J. A. Wiley et al. [*J. Virol.*, 66, pp. 5744–5751 (1992)]. Briefly, sera or hybridoma culture supernatants were added to radiolabeled samples containing equal amounts of [$^{35}$S]methionine. The mixtures were allowed to incubate for 90 minutes at 4° C. with constant agitation. The immune complexes were then precipitated with bovine serum albumin-treated protein A Sepharose (Pharmacia) for 1 hour at 4° C. The beads were pelleted and washed three times in Tris buffered saline at pH 8.0, and the antigen complexes were then dissociated by boiling in sample buffer. The antigens were analyzed by electrophoresis on SDS-PAGE. The gels were fixed, enhanced for fluorography using Amplify (Amersham Canada Limited, Oakville, Ontario, Canada), dried, and then exposed to X-ray film.

B. Characterization of the Heat Shock Response in *S. pneumoniae*

Figure 1:
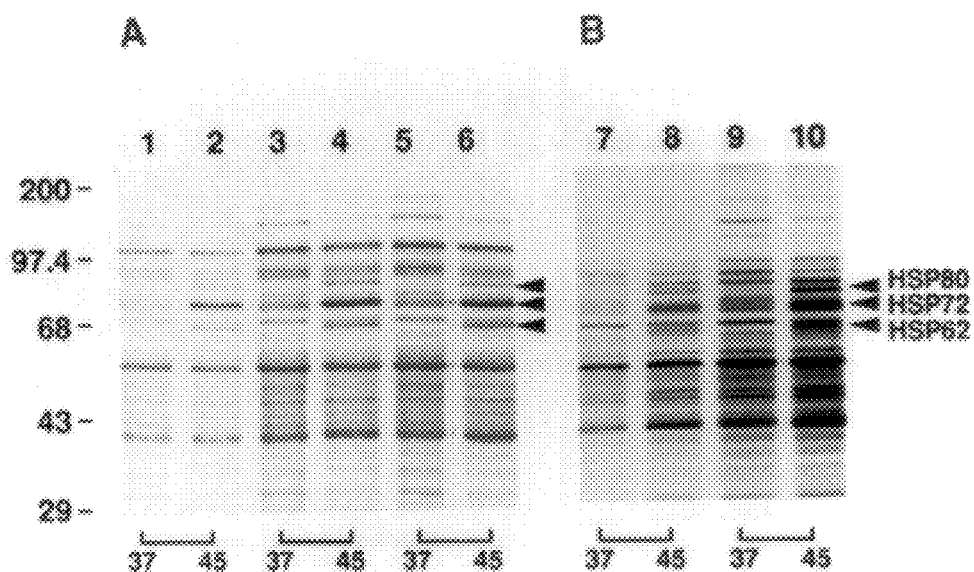
FIG. 1 depicts a fluorogram, which shows the effect of heat shock on *S. pneumoniae* protein synthesis. The cell extracts in panel A are *S. pneumoniae* type 6 strain 64. The cell extracts in panel B are *S. pneumoniae* type 4 strain 53. The cell extracts in the odd numbered lanes were incubated at 37° C. The cell extracts in the even numbered lanes were incubated at 45° C. for 5 minutes. The cell extracts were then labeled with [$^{35}$S]methionine for 10 minutes (lanes 1, 2 and 7, 8), 30 minutes (lanes 3, 4 and 9, 10), or 60 minutes (lanes 5, 6). Molecular mass markers in kilodaltons are shown to the left. The positions of HSP80, HSP72 and HSP62 are shown by arrows at the right-hand side of each panel.

We studied the heat shock response of *S. pneumoniae* by examining the pattern of protein synthesis before and after a shift from 37° C. to 45° C. FIG. 1 shows the results when *S. pneumoniae* type 6 strain 64 (panel A) and type 4 strain 53 (panel B) were grown at 37° C., incubated at 37° C. (lanes 1,3,5,7 and 9) or at 45° C. (lanes 2, 4, 6, 8 and 10) for 5 minutes, and then labeled with [$^{35}$S]methionine for 10 minutes (lanes 1,2 and 7,8), 30 minutes (lanes 3,4 and 9,10), or 60 minutes (lanes 5,6).

The fluorogram derived from SDS-PAGE indicated that the synthesis of at least three proteins was increased by increasing the temperature (FIG. 1). The most prominent induced protein was about 72 kDa (HSP72), whereas the other two were approximately 80 kDa (HSP80) and 62 kDa (HSP62). Increased protein synthesis was already apparent after 10 minutes of labeling (FIG. 1, lanes 1, 2 and 7, 8) and became more significant when the labeling period was prolonged to 30 minutes (FIG. 1, lanes 3, 4 and 9, 10) and 60 minutes (FIG. 1, lanes 5, 6). The effect of elevated temperature on the protein synthesis profile of two different *S. pneumoniae* strains was similar, with HSPS of similar molecular mass being synthesized (compare Panel A (type 6 strain 64) to Panel B (type 4 strain 53) in FIG. 1).

Figure 2:
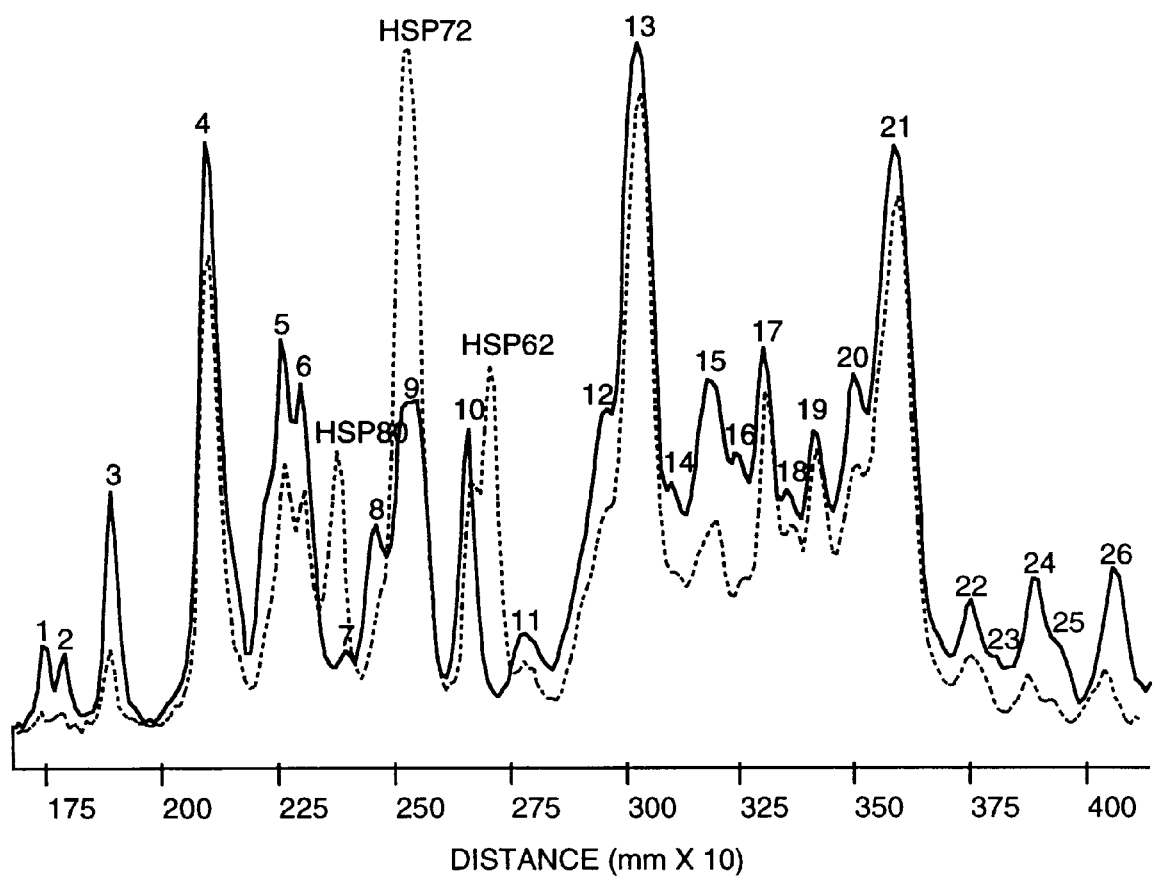
FIG. 2 is a graphical depiction of a comparison of the electrophoretic profiles of [$^{35}$S]methionine-labeled proteins in *S. pneumoniae* in the presence (----) or absence (___) of exposure to heat shock. Densitometric tracings were determined by measuring the relative optical density (Y axis) vs. the mobility of labeled protein bands (X axis). The densitometric scans of the SDS PAGE of FIG. 1, lanes 1 and 2, is shown.

Analysis of the densitometric tracings from scanning the protein synthesis profiles allowed the estimation of the relative amounts of proteins. For example, with respect to heat-shocked *S. pneumoniae* type 6 strain 64, after 10 minutes of labeling, HSP80 and HSP62 made up 2.9% and 6.8% of the labeled proteins, respectively, compared to less than 0.1% at 37° C. (FIG. 2). Labeled proteins having an apparent molecular mass of 72 kDa were detected at both 37° C. and 45° C. conditions (FIG. 2). Radioimmunoprecipitation analysis revealed, however, that HSP72 was undetectable at 37° C. (supra; and FIGS. 3, 4 and 6) thus indicating that peak 9 from FIG. 2 corresponds to protein component(s) comigrating with HSP72. Assuming no variation in the labeling of this material, these results would suggest that the amount of HSP72 represents 8.7% of the total labeled cell protein after heat shock treatment. A comparison of the densitometric tracings revealed that cellular proteins corresponding to peaks 4, 10, 13, 17, 19, and 21 were synthesized at almost the same rate irrespective of heat shock treatment (FIG. 2). However, the synthesis of several proteins (peaks 1, 2, 3, 15, 20, 22, 24, and 26) declined considerably in response to heat shock (FIG. 2).

C. Immune Responses to *S. pneumoniae* HSPs

Figure 3:
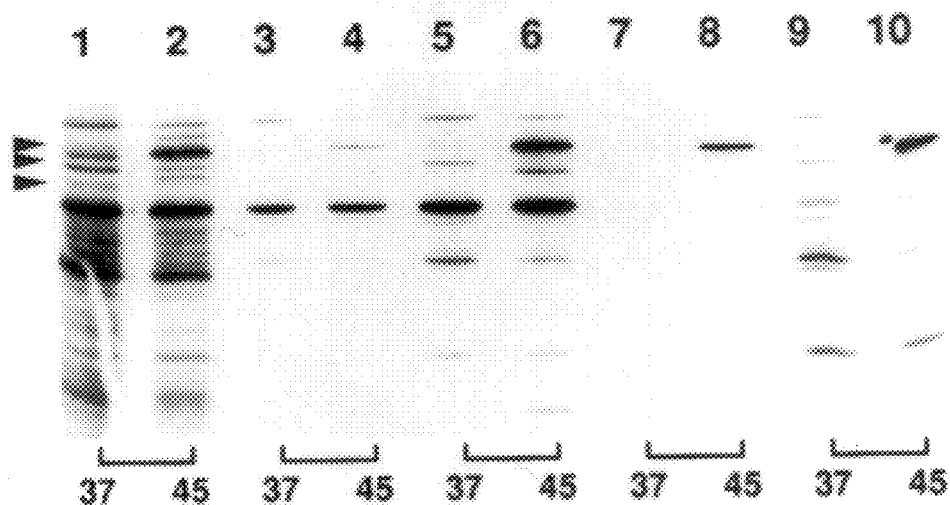
FIG. 3 depicts a fluorogram, which shows the *S. pneumoniae* protein antigens immunoprecipitated by sera from mice immunized with detergent-soluble *S. pneumoniae* protein extract. [$^{35}$S]methionine-labeled proteins from *S. pneumoniae* grown at 37° C. and incubated at 37° C. (lanes 3, 5, 7 and 9) or heat-shocked at 45° C. (lanes 4, 6, 8 and 10) were immunoprecipitated with sera from mouse 1 (lanes 3 to 6) or mouse 2 (lanes 7 to 10) and then analyzed by SDS-PAGE and fluorography. The sera were tested after the first (lanes 3,4 and 7,8) and after the second (lanes 5,6 and 9,10) immunization. Cell lysates from [$^{35}$S]methionine-labeled non heat-shocked and heat-shocked *S. pneumoniae* are shown in lanes 1 and 2, respectively. The position of HSPs is indicated by the arrows at the left of the fluorogram.
Figure 4:
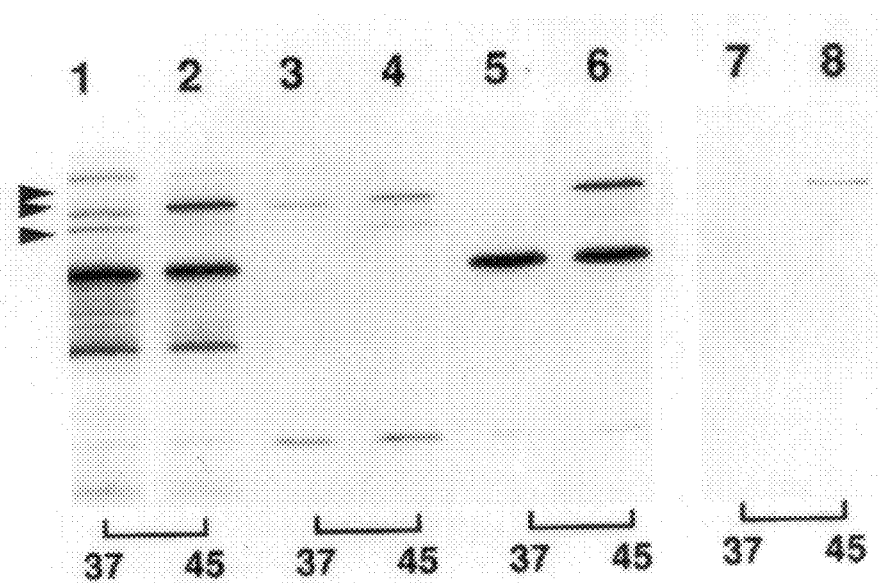
FIG. 4 depicts a fluorogram, which shows the *S. pneumoniae* protein antigens immunoprecipitated by sera from mice immunized with heat-killed *S. pneumoniae* bacteria. [$^{35}$S]methionine-labeled proteins from *S. pneumoniae* grown at 37° C. and incubated at 37° C. (lanes 3, 5 and 7) or heat-shocked at 45° C. (lanes 4, 6 and 8) were immunoprecipitated with sera from mouse 1 (lanes 3,4), mouse 2 (lanes 5,6) or mouse 3 (lanes 7, 8) and then analyzed by SDS-PAGE and fluorography. Sera were tested after the second immunization only. Cell lysates from [$^{35}$S] methionine-labeled non heat- and heat-shocked *S. pneumoniae* are shown in lanes 1 and 2, respectively. The position of HSPs is indicated by the arrows at the left of the fluorogram.

In order to assess the antibody response to pneumococcal HSPs, mouse sera were first assayed by radioimmunoprecipitation. The repertoire of labeled proteins recognized by sera from mice immunized with *S. pneumoniae* antigen preparations are shown in FIGS. 3 and 4. FIG. 3 relates to detergent soluble protein preparations. FIG. 4 relates to heat-killed bacterial preparation. Although many bands were detected by most antisera, HSP72 was a major precipitation product. The specificity of antibodies for HSP72 was demonstrated by the detection of proteins among heat-shocked products only (FIG. 3, lanes 4, 6, 8 and 10; FIG. 4, lanes 4, 6 and 2). Interestingly, all immunized mice consistently recognized HSP72. The antibodies reactive with the HSP72 were not specific to the strain used during the immunization since strong reactivities were observed with heterologous *S. pneumoniae* HSP72. It should be noted that in addition to HSP72, one sera precipitated comigrating product labeled at both 37° C. and 45° C. (FIG. 4, lane 4). This 72 kDa-product probably corresponds to component from peak 9 in FIG. 2 and was not detected in immunoblots. HSP62 is another immune target which was precipitated by some but not all immune sera (FIG. 3, lane 6 and, FIG. 4, lanes 4 and 6). None of the sera tested reacted with HSP80. No proteins were precipitated when preimmune sera taken from the mice used in this study were tested for the presence of antibodies reactive with the labeled products.

Figure 5:
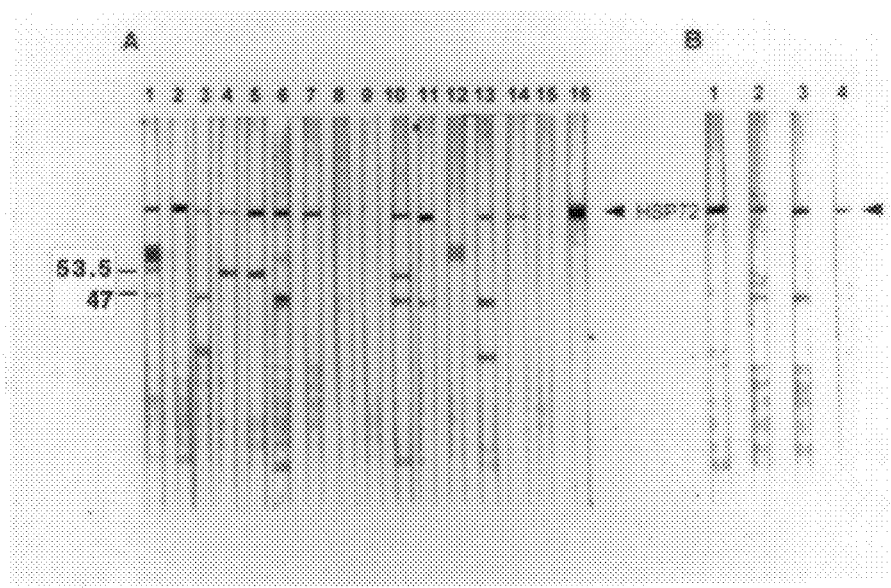
FIG. 5 depicts a photograph, which shows the *S. pneumoniae* antigens detected by Western blot analysis. Whole cell extracts were probed with sera from 15 mice (lanes 1–15) immunized with heat-killed *S. pneumoniae* bacteria. Lane 16 shows the HSP72 protein detected by MAb F1-Pn3.1. In panel A, the sera were tested after the second immunization. In panel B, the reactivity of 4 out of 15 sera tested after the first immunization is shown. The positions of 53.5 kDa- and 47 kDa-protein bands are indicated by the bars at the left. The position of HSP72 is shown by the arrows at the right of each panel.

As depicted in FIGS. 3 and 5, antibodies to HSP72 could be detected after one immunization with either detergent-soluble proteins or whole cells extracts of *S. pneumoniae*. In addition, a marked increase in the antibody response to HSP72 was observed after a second immunization (FIG. 3, compare 4 and 6, and lanes 8 and 10).

The immunoblot patterns of 15 mice immunized with heat-killed *S. pneumoniae* bacteria were remarkably consistent with the results of the previously described radioimmunoprecipitation. Although antibody response variation occurred to a variety of proteins, HSP72 was a major immunoreactive antigen with 8 (53%) positive sera after the first immunization (FIG. 5). Antibodies to HSP72 were detected in 13 out of 15 (87%) immune sera tested after the second immunization. Two other prominent antigens having apparent molecular mass of 53.5 and 47 kDa were detected in 5 (33%) and 7 (47%) sera, respectively (FIG. 5). The 72 kDa-reactive band was confirmed as the pneumococcal HSP72 by using recombinant HSP72 antigens (Example 3, infra) in an immunoblot assay. Preimmune sera failed to detect any pneumococcal proteins.

Example 2—Isolation of Monoclonal Antibodies Against Epitopes of HSP72

A. Procedures

1. Immunization of Mice and Fusion

Female Balb/c mice (Charles River Laboratories) were immunized with *S. pneumoniae* antigens. One set of mice (fusion experiment 1) were immunized by peritoneal injection with $10^7$ formalin-killed whole cell antigen from strain MTL suspended in Freund's complete adjuvant, and were boosted at two-week intervals with the same antigen and then with a sonicate from heat-killed bacteria in Freund's incomplete adjuvant. A second group of mice (fusion experiment 2) were immunized three times at three-week intervals with 75 µg of detergent-soluble pneumococcal antigens extracted from strain 64 (type 6) in 25 µg of Quil A adjuvant (Cedarlane Laboratories Ltd., Hornby, Ontario, Canada). Three days before fusion, all mice were injected intraperitoneally with the respective antigen suspended in PBS alone. Hybridomas were produced by fusion of spleen cells with nonsecreting SP2/0 myeloma cells as previously described by J. Hamel et al. [*J. Med. Microbiol.*, 23, pp. 163–170 (1987)]. Specific hybridoma were cloned by sequential limiting dilutions, expanded and frozen in liquid nitrogen. The class, subclass, and light-chain type of MAbs were determined by ELISA as described by D. Martin et al., [*Eur. J. Immunol.*, 18, pp. 601–606 (1988)] using reagents obtained from Southern Biotechnology Associates Inc. (Birmingham, Ala.).

2. Subcellular Fractionization

Pneumococci were separated into subcellular fractions according to the technique described by Pearce et al. [*Mol. Microbiol.*, 9, pp. 1037–1050 (1993)]. Briefly, *S. pneumo-* niae strain 64 (type 6) was grown in Todd Hewitt broth supplemented with 0.5% (w/v) yeast extract for 6 hours at 37° C. and isolated by centrifugation. Cell pellets were resuspended in 25 mM Tris-HCl pH 8.0, 1 mM EDTA, 1 mM phenylmethylsulphonylfluoride (PMSF) and sonicated for 4 minutes with 15 second bursts. Cellular debris were removed by centrifugation. The bacterial membranes and cytoplasmic contents were separated by centrifugation at 98,000 g for 4 hours. The cytoplasmic (supernatant) and the membrane (pellet) fractions were adjusted to 1 mg protein per ml and subjected to SDS-PAGE and immunoblot analyses.

B. Identification and Characterization of MAbs to the HSP72 of S. pneumoniae

Figure 6:
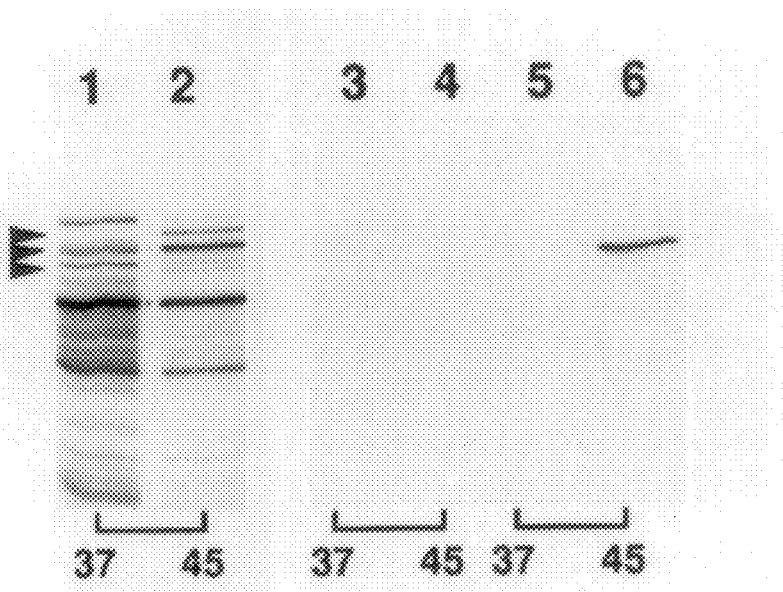
FIG. 6 depicts a fluorogram showing the specificity of MAb F1-Pn3.1 for HSP72. [$^{35}$S]methionine-labeled proteins of *S. pneumoniae* in the absence (lanes 1, 3 and 5) or presence (lanes 2, 4 and 6) of exposure to heat shock were immunoprecipitated with IgG2a-control MAb (lane 3,4) or F1-Pn3.1 (lane 5,6) and then analyzed by SDS-PAGE and fluorography. Cell lysates from [$^{35}$S]methionine-labeled non heat-shocked and heat-shocked *S. pneumoniae* are shown in lanes 1 and 2, respectively. The position of HSPs (all three) is shown by the arrows at the left of the fluorogram.

Culture supernatants of hybridomas were initially screened by dot enzyme immunoassay using whole cells from S. pneumoniae strain 65 (type 4) according to the procedures described in D. Martin et al. (supra). Positive hybridomas were then retested by immunoblotting in order to identify the hybridomas secreting MAbs reactive with the HSP72. Of 26 hybridomas with anti-S. pneumoniae reactivity in immunoblot, four were found to recognize epitopes present on a protein band with an apparent molecular mass of 72 kDa. The four hybridomas were designated F1-Pn3.1 (from fusion experiment 1) and F2-Pn3.2, F2-Pn3.3 and F2-Pn3.4 (from fusion experiment 2). Isotype analysis revealed that hybridoma F1-Pn3.1 (from fusion experiment 1) secreted $IgG_{-2ak}$ immunoglobulins, whereas hybridomas F2-Pn3.2, F2-Pn3.3, and F2-Pn3.4 (from fusion experiment 2) all secreted $IgG_{1k}$. The specificity of the MAbs for HSP72 was clearly demonstrated by the lack of radioimmunoprecipitation activity against [$^{35}$S]methionine-labeled S. pneumoniae proteins obtained from cultures incubated at 37° C. and the immunoprecipitation of a 72 kDa-protein with heat shock-derived lysates incubated at 45° C. FIG. 6, (lanes 5 and 6)demonstrates the results obtained for MAb F1-Pn3.1. The same results were obtained with MAbs F2-Pn3.2, F2-Pn3.3 and F2-Pn3.4

Figure 7:
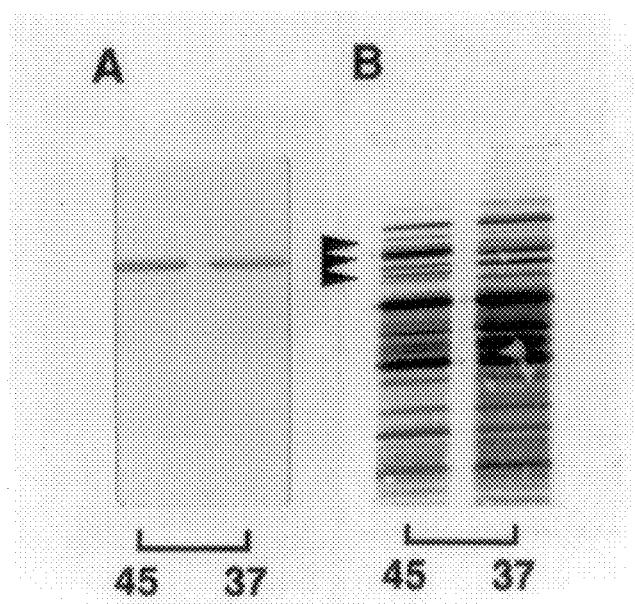
FIG. 7, panel A, depicts an immunoblot, which shows the reaction of heat-shocked and non heat-shocked [$^{35}$S] methionine-labelled *S. pneumoniae* cell extracts with MAb F1-Pn3.1. Lane 1 contains heat-shocked cell lysates (45°

[$^{35}$S]methionine-labelled lysates from nonheat-shocked and heat-shocked S. pneumoniae cells probed with the MAbs were electrophoresed on SDS-PAGE gels and then subjected to Western blot analysis. The resulting immunoblots revealed the presence of HSP72 antigen in both samples. FIG. 7, panel A, shows the results obtained for MAb F1-Pn3.1. The same results were obtained with MAbs F2-Pn3.2, F2-Pn3.3 and F2-Pn3.4. Accordingly, the heat shock stress did not significantly increase the reactivity of anti-HSP72 monoclonal antibodies. The fluorograph of the immunoblots, however, clearly showed that the heat shock response had occurred (FIG. 7, panel B). These experiments revealed that the rate of synthesis of S. pneumoniae HSP72 increases in response to heat shock, but that the absolute amounts of HSP72 do not increase after heat shock.

C. Cellular localization of HSP72

In order to investigate the cellular location of HSP72, S. pneumoniae cell lysates were fractionated by differential centrifugation resulting in a soluble fraction and a particulate fraction, enriched in membrane proteins, supra. Sample containing 15 μg protein of membrane fraction (lane 1) and cytoplasmic fraction (lane 2) of S. pneumoniae were electrophoresed on SDS-PAGE, transferred to nitrocellulose and probed with MAb F1-Pn3.1. In the resulting Western blots, HSP72 was found in both fractions, with the majority of the protein associated with the cytoplasmic fraction (FIG. 8).

Example 3—Molecular Cloning, Sequencing and Expression of Genes Coding for HSP72 Antigens A. Procedures 1. Strains and Plasmids Strains and plasmids used in this study are listed in Table 1.

TABLE 1

BACTERIAL STRAINS, PHAGES AND PLASMIDS

| Strain, Phage Plasmid | Relevant Characteristics | Reference or Source |
|---|---|---|
| *E. coli* Strains | | |
| JM109 | Δ(lac-proAB) [F'traD proAB lacI$^q$ ZΔM15] | BRL |
| Y1090 | r$_k$-m$_k$- lon supF [pMC9] | Amersham |
| BL21 (DE3) | lacUV5-T7 RNA polymerase | Studier et al. (infra) |
| Phages | | |
| λgt11 | cI857 S100 cloning vector | Amersham |
| λJBD7 | LacZ-HSP72 fusion; 2.3 kb EcoRI fragment in λgt11 | This study |
| λJBD17 | FucI-HSP72 chimeric; 2.4 kb EcoRI and 2.3 kb EcoRI fragments in λgt11 | This study |
| Plasmids | | |
| pWSK29 | Amp$^r$; low copy number cloning vector | Wang et al. (intra) |
| pWKS30 | same as PWSK29 but opposite multi cloning site | Wang et al. (infra) |
| pJBD171 | same as λJBD17 but in PWSK29 | This study |
| pJBD177 | 2.8 kb XhoI-EcoRI fragment in pWKS30 no recombinant HSP72 protein expressed | This study |
| pJBD179 | FucI-HSP72 fusion; 2.4 kb EcoRI and 0.8 kb EcoRI-EcoRV fragments in pWSK29 | This study |
| pT7-5 | Amp$^r$; T7 promoter φ10 | Tabor et al. (infra) |
| pT7-6 | same as pT7-5 but opposite multi cloning site | Tabor et al. (infra) |
| pJBDf51 | same as pJBD179 but in pT7-5 | This study |
| pJBDf62 | same as pJBD179 but in pT7-6 | This study |
| pDELTA1 | Amp$^r$; Tn 1000 | BRL |
| pJBDΔ1 | same as pJBD179 but in pDELTA1 | This study |
| pJBD291 | HSP72; 3.2 kb HindIII fragment in pWSK29 | This study |
| pJBDk51 | same as pJBD291 but in pT7-5 | This study |
| PJBDΔ4 | same as pJBD291 but in pDELTA1 | This study |

*E. coli* strains were grown in L broth or on L agar at 37° C. When necessary, ampicillin was added to the media at the concentration of 50 μg/ml. Plasmids were isolated by using the Magic/Wizard Mini-Preps kit (Promega, Fisher Scientific, Ottawa, Canada).

2. General Recombinant DNA Techniques

Restriction endonucleases, T4 DNA ligase, and DNA molecular weight standards were purchased from Boehringer Mannheim Canada, Laval, Quebec or Pharmacia Biotech, Uppsala, Sweden. DNA restriction endonuclease digestion and ligation were performed as described by J. Sambrook et al. [*Molecular cloning. A laboratory manual.* Cold Spring Harbor Laboratory Press, N.Y. (1989)]. Agarose gel electrophoresis of DNA fragments was performed following the procedure of J. Sambrook et al. (supra) using the TAE buffer (0.04M Tris-acetate; 0.002M EDTA) from Boehringer Mannheim. DNA fragments were purified from agarose gel by using the Prep-A-Gene DNA purification kit (Bio-Rad Laboratories Ltd., Mississauga, Ontario). Transformation was carried out by electroporation with the Gene Pulser (Bio-Rad) following the protocol provided by the manufacturer.

3. Construction and Screening of Genomic Library

A genomic S. pneumoniae DNA library was generated in the bacteriophage expression vector λgt11 (λgt11 cloning system, Amersham) according to the procedure provided by the manufacturer. Chromosomal DNA of S. pneumoniae type 6 strain 64 was prepared by following the procedure of J. C. Paton et al. [Infect. Immun., 54, pp. 50–55 (1986)]. The S. pneumoniae chromosomal DNA was partially digested with EcoRI, and the 4- to 7-kb fragments were fractionated and purified from agarose gel. The fragments were ligated into λgt11 arms, packaged, and the resulting phage mixtures used to infect E. coli Y1090. Immunoscreening of plaques expressing recombinant HSP72 antigens was performed using HSP72-specific monoclonal antibody F1-Pn3.1, supra. Plaque clones expressing peptides recognized by MAb F1-Pn3.1 were isolated and purified. Liquid lysates were prepared and DNA was purified from a Promega Lambda-Sorb phage adsorbent according to the manufacturer's directions followed by conventional DNA purification procedures.

4. Southern Blot Analysis

The nonradioactive DIG DNA Labelling and Detection kit, obtained from Boehringer Mannheim, was used to perform Southern blot analysis in this example. The DNA fragments selected for use as probes (infra) were purified by agarose gel electrophoresis and then labelled with digoxigenin (DIG)-11-dUTP. Pneumococcal chromosomal DNA was digested with HindIII and the digests were separated by electrophoresis on an 0.8% SDS-PAGE gel and transformed onto positive charged nylon membranes (Boehringer Mannheim) as described by J. Sambrook et al. (supra). The membrane was then blotted with the DIG-labelled DNA probes according to the protocol of the manufacturer.

5. DNA Sequencing and Sequence Analysis

The DNA fragments sequenced in this example were first cloned into plasmid pDELTA 1 (GIBCO BRL Life Technologies, Burlington, Ontario). A series of nested deletions were generated from both strands by in vivo deletion mediated by Tn 1000 transposon transposition (Deletion Factory System, GIBCO BRL) following the procedures provided by the supplier. These deletions were sized by agarose gel electrophoresis and appropriate deletion derivatives were selected for sequencing by the dideoxynucleotide chain terminating method of F. Sanger et al. [Proc. Natl. Acad. Sci. USA, 74, pp. 5463–5467 (1977)]. To sequence the gaps between deletion templates, oligonucleotides were synthesized by oligonucleotide synthesizer 392 (ABI, Applied Biosystems Inc., Foster City, Calif.). The sequencing reaction was carried out by PCR (DNA Thermal Cycler 480, Perkin Elmer) using the Taq DyeDeoxy Terminator Cycle Sequencing kit (ABI), and DNA electrophoresis was performed on automated DNA sequencer 373A (ABI).

6. Expression of Cloned Gene in E. coli T7 RNA pol/promoter system

High level expression of the cloned gene in this example was achieved by employing the bacteriophage T7 RNA polymerase/promoter system in E. coli. The DNA fragment specifying the recombinant protein was ligated into plasmids pT7-5 or pT7-6 [S. Tabor and C. C. Richardson, Proc. Natl. Acad. Sci. USA, 82, PP. 1074–1078 (1985)], in a proper orientation in which the gene to be expressed was placed under the control of phage T7 RNA polymerase specific promoter Φ10. The resulting plasmid was transformed into E. coli strain BL21 (DE3) [F. W. Studier, and B. A. Moffatt, J. Mol. Biol., 189, pp. 113–130 (1986)] which carries the T7 RNA polymerase structural gene on its chromosome under the control of the inducible lacUV5 promoter. Upon IPTG induction, the T7 RNA polymerase induced in the BL21 (DE3) transformants specifically transcribed the gene under the control of T7 promoter Φ10. The overexpressed recombinant proteins were visualized by either Western blotting or Coomassie Blue staining.

7. N-terminal Amino Acid Sequence Analysis of HSP72

Pneumococcal HSP72 was purified by immunoprecipitation using MAb F1-Pn3.1 (supra) and samples of cell wall extracts of S. pneumoniae strain 64 prepared as described by L. S. Daniels et al. [Microb. Pathogen., 1, pp. 519–531 (1986)] as antigen. The immune precipitates were resolved by SDS-PAGE and then transferred to polyvinylidene difluoride (PVDF) membrane by the method of P. Matsudaira [J. Biol. Chem., 262, pp. 10035–10038 (1987)]. PVDF membrane was stained with Coomassie Blue, the HSP72 band excised and then analyzed in an automated protein sequencer (ABI), according to standard procedures.

B. Construction of Plasmids Containing S. pneumoniae HSP72 Gene Fragments Corresponding to C-169

The λgt11 S. pneumoniae genomic DNA library was screened with the HSP72-specific MAb F1-Pn3.1. Seventeen (17) immunoreactive clones were isolated and purified from a total of 1500 phages tested. To confirm the specificity of the proteins expressed by the recombinant phages, Western blot analysis of the recombinant phage lysates was performed. Two groups of clones were identified among the 17 positive clones recognized by MAb F1-Pn3.1 and their representatives were designated as λJBD7 and λJBD17 for further characterization. As shown in FIG. 9, whole cell extracts from S. pneumoniae strain 64 (lane 1) and phage lysates from E. coli infected with λJBD17 (lanes 2 and 3) or λJBD7 (lanes 4 and 5) cultured in the presence (+) or absence (−) of IPTG were subjected to 10% polyacrylamide gel electrophoresis and were electrotransferred to nitrocellulose. The immunoblot was probed with HSP72-specific MAb F1-Pn3.1. Clone λJBD17 had two EcoRI-EcoRI insert fragments of 2.4 kb and 2.3 kb (FIG. 10), and expressed a chimeric recombinant protein having an apparent molecular mass of 74 kDa on SDS-PAGE gel (FIG. 9, lanes 2 and 3). Clone λJBD7 was found to contain a 2.3 kb EcoRI insert fragment and produced an apparent fusion protein consisting of LacZ and the 74 kDa chimeric protein expressed from clone λJBD17. The fusion protein had an apparent molecular mass of 160 kDa as estimated by SDS-PAGE (FIG. 9, lane 5). The expression of the chimeric recombinant protein encoded by phage λJBD17 was independent of IPTG induction (FIG. 9, lanes 2 and 3) while the expression of the recombinant fusion protein encoded by phage λJBD7 was dependent on induction of the lac promoter (FIG. 9, lanes 4 and 5).

In an attempt to subclone the HSP72 gene, the pneumococcal DNA insert from clone λJBD17 was extracted, purified and ligated into a low copy plasmid pWSK29 [R. F. Wang and S. R. Kushner, Gene, 100, pp. 195–199 (1991)] to generate plasmid pJBD171. The insert from pJBD171 was characterized by restriction mapping (FIG. 10B), and a series of subcloning and immunoblotting was carried out to define the boundaries of the gene coding for the antigen reactive with MAb F1-Pn3.1. The region responsible for expression of the 74 kDa chimeric protein was found to localize on the 3.2 kb EcoRI-EcoRV fragment, which consists of the intact 2.4 kb EcoRI-EcoRI fragment and the 0.8 kb EcoRI-EcoRV portion of the 2.3 kb EcoRI-EcoRI fragment. The plasmid carrying the 3.2 kb EcoRI-EcoRV insert was designated pJBD179.

C. Expression and DNA Sequence Analysis of a Chimeric Gene Coding for C-169

To further determine the transcriptional direction of the gene coding for the 74 kDa chimeric protein on the 3.2 kb EcoRI-EcoRV fragment, and to increase the yield of the 74 kDa chimeric protein for immunological study, we decided to express the 75 kDa chimeric protein in the E. coli T7 RNA and T7 promoter system. The 3.2 kb EcoRI-EcoRV fragment, derived from pJBD179, was ligated into plasmids pT7-5 and pT7-6 in which the multi-cloning sites were placed in opposite orientation with respect to the T7 RNA polymerase specific T7 promoter Φ10. The ligation mixture was used to transform E. coli JM109 and positive transformants reactive with MAb F1-Pn3.1 were identified by the colony lifting method described by J. Sambrook et al. [supra]. The resulting recombinant plasmids, derived from pT7-5 and pT7-6, were designated pJBDf51 and pJBDf62, respectively. The intact 3.2 kb EcoRI-EcoRV insert in these recombinant plasmids and their orientation was determined by restriction mapping. To achieve overexpression of the 75 kDa chimeric protein, pJBDf51 and pJBDf62 were transformed, separately, into E. coli BL21 (DE3). The transformants were induced with IPTG (1 mM) for 3 hours at 37° C. The cells were harvested, washed, resuspended in 1% SDS and boiled for 10 minutes. The lysates were then used for SDS-PAGE and immunoblot analysis. As expected, both transformants produced the 75 kDa chimeric protein readily detected by Western blotting with MAb F1-Pn3.1 (FIG. 11). However, under the IPTG induction condition, only transformants BL21 (DE3) (pJBDf51) overexpressed the 75 kDa chimeric protein (FIG. 11A and B, lane 2) indicating that the transcriptional direction of the gene on the 3.2 kb EcoRI-EcoRV fragment is from the EcoRI end towards the EcoRV end (FIG. 10A).

The 3.2 kb EcoRI-EcoRV fragment was cloned into plasmid pDELTA 1 to yield plasmid pJBDΔ1. A series of overlapping deletions were generated and used as DNA sequencing templates. The DNA sequence of the entire 3.2 kb EcoRI-EcoRV insert is SEQ ID NO:1. Two open reading frames ("ORFs") were found and their orientation is indicated in FIG. 10B ("ORF27" and "FucI-HSP72 (C-169)"). In front of these two ORFs, putative ribosome-binding sites were identified (SEQ ID NO:1, nucleotides 18–21 and 760–763). No obvious −10 and −35 promoter sequences were detected. ORF27 spans nucleotides 30–755 (SEQ ID NO:1) and encodes a protein of 242 amino acids with a calculated molecular weight of 27,066 daltons. The deduced amino acid sequence of this protein is SEQ ID NO:2. We designated this gene orf27, and compared it to other known sequences. No homologous gene or protein was found. The large ORF (nucleotides 771–2912, SEQ ID NO:1) specifies a protein of 714 amino acids with a predicted molecular mass of 79,238 daltons. The deduced amino acid sequence of this protein is SEQ ID NO:3. This ORF was compared with other known sequences to determine its relationship to other amino acid sequences. This analysis revealed a high degree of similarity of the encoded protein to the sequence of E. coli fucose isomerase (FucI) and to several HSP70 gene family members, also known as DnaK genes. Alignment of SEQ ID NO:3 and those of the E. coli FucI and HSP70 (Dnak) proteins indicated that the N-terminal portion corresponding to amino acids 1 to 545 (SEQ ID NO:3) of the 75 kDa chimeric protein is highly homologous to E. coli FucI, while the C-terminal portion corresponding to amino acids 546–714 (SEQ ID NO:3) is similar to HSP70 (DnaK) proteins. It is noteworthy that there is an EcoRI restriction site lying in the junction of these two portions of the gene coding for the 75 kDa protein (SEQ ID NO:1, between nucleotides 2404 and 2405). Other restriction sites exist between nucleotides 971 and 972 (Pst I), nucleotides 1916 and 1917 (Pst I), nucleotides 1978 and 1979 (Xho I), and nucleotides 3164 and 3165 (EcoRV). From these data we concluded that the 75 kDa protein was a chimeric protein encoded by two pieces of S. pneumoniae chromosomal DNA, a 2.4 kb EcoRI-EcoRI fragment derived from the FucI homologous gene and a 2.3 kb EcoRI-EcoRI fragment derived from the HSP72 gene.

D. Southern Blot Analysis

Southern blotting was performed in order to confirm that the 75 kDa protein is a chimeric protein and to attempt to clone the entire pneumococcal HSP72 gene. Chromosomal S. pneumoniae DNA was digested with HindIII to completion, separated on a 0.8% agarose gel, and transferred onto two positively charged nylon membranes (Boehringer Mannheim). The membranes were then blotted with either the 0.8 kb EcoRI-EcoRV probe, derived from the 2.3 kb EcoRI-EcoRI fragment, or the 1 kb PstI-PstI probe, obtained from the 2.4 kb EcoRI-EcoRI fragment. Both probes had been previously labelled with digoxigenin-dUTP. These two probes hybridized two individual HindIII fragments of different sizes (FIGS. 10B and 10C). The 0.8 kb EcoRI-EcoRV probe recognized the 3.2 kb HindIII fragment and the 1 kb PstI-PstI probe reacted with the 4 kb HindIII fragment. This result further indicated that the gene responsible for the expression of the 74 kDa chimeric protein was generated by fusion, in frame, of two pieces of EcoRI fragments, one originated from the fragment containing the 5' portion of the S. pneumoniae FucI homologue, the other derived from the segment carrying the C-169 fragment of the pneumococcal HSP72 gene. The fact that the 0.8 kb EcoRI-EcoRV probe hybridized a single 3.2 kb fragment suggested that there is only a single HSP72 gene copy in S. pneumoniae.

E. Production of Recombinant HSP72

A partial pneumococcal genomic library was generated by ligation of the pool of HindIII digests of chromosomal DNA, with sizes ranging from 2.8 to 3.7 kb, into plasmid pWSK29/HindIII. The ligation mixture was used to transform E. coli strain JM 109 and the transformants were screened by hybridization with the 0.8 kb EcoRI-EcoRV probe. One representative plasmid from four positive hybridizing clones was named pJBD291. Restriction analysis of the insert and Western blot of the cell lysate of transformants were employed to verify that the plasmid pJBD291 indeed carries the 3.2 kb HindIII fragment containing the HSP72 gene expressing the recombinant HSP72 protein (FIG. 10B). The HSP72 protein expressed by the transformants (pJBD291) migrated on the SDS-PAGE gel at the same position as the native HSP72 protein (FIG. 12). To sequence the entire HSP72 gene and to overexpress the full-length HSP72 protein, the 3.2 kb HindIII fragment was isolated from plasmid pJBD291, and subcloned into plasmids pDELTA 1 and pT7-5 to generate pJBDΔ4 and pJBDk51, respectively.

The entire 3.2 kb HindIII DNA fragment carried on the plasmid pJBDΔ4 and the 2.3 kb EcoRI-EcoRI DNA fragment contained on the plasmid pJBD177 were sequenced. Altogether, the nucleotide sequence comprised 4320 base pairs and revealed two ORFs (SEQ ID NO:4). The first ORF, starting at nucleotide 682 and ending at nucleotide 2502 (SEQ ID NO:4), was identified as the pneumococcal HSP72 gene, and the second ORF, spanning from nucleotide 3265 to nucleotide 4320 (SEQ ID NO:4), was located 764 base pairs downstream from the HSP72 structural gene and was identified as the 5' portion of the pneumococcal DnaJ gene. The putative ribosome binding site ("AGGA") was located 9 base pairs upstream from the start codon of the HSP72 structural gene, while the typical ribosome binding site ("AGGA") was found 66 base pairs upstream from the start codon of the DnaJ structural gene. No typical 5' regulatory region was identified in front of these two genes. Restriction sites are located between nucleotides 1 and 2 (HindIII), nucleotides 1318 and 1319 (EcoRI), nucleotides 1994 and 1995 (EcoRI), nucleotides 3343 and 3344 (HindIII), and nucleotides 4315 and 4316 (EcoRI). The gene organization of HSP72 (DnaK) and DnaJ in S. pneumoniae is similar to that of E. coli [Saito, H. and Uchida, Mol. Gen. Genet. 164, 1–8 (1978)] as well as several other Gram positive bacteria [Wetzstein, M. et al., J. Bacteriol. 174, 3300–3310 (1992)]. However, the intragenic region of S. pneumoniae is significantly larger and no ORF for the grpE gene was found upstream of the HSP72 (DnaK) structural gene.

The predicted HSP72 protein has 607 amino acids and a calculated molecular mass of 64,755 daltons, as compared to the 72 kDa molecular mass estimated by SDS-PAGE. The predicted HSP72 protein is acidic with an isoelectric point (pI) of 4.35. Automated Edman degradation of the purified native HSP72 protein extracted from S. pneumoniae strain 64 revealed SKIIGIDLGTTN-AVAVLE as the 19 amino acid N-terminal sequence of the protein. The amino-terminal methionine was not detected, presumably due to in situ processing which is known to occur in many proteins. No amino acid residue was identified on position 13. The 19 amino acid N-terminal sequence obtained from the native HSP72 protein is in full agreement with the 19 amino acid N-terminal sequence deduced from the nucleotide sequence of the recombinant S. pneumoniae HSP72 gene (SEQ ID NO:5) thus confirming the cloning. This N-terminal sequence showed complete identity with the DnaK protein from Lactococcus lactis and 68.4% identity with the DnaK protein from Escherichia Coli. Similarly, the alignment of the predicted amino acid sequence of HSP72 (SEQ ID NO:5) with those from other bacterial HSP70 (DnaK) proteins also revealed high homology (FIGS. 13A–13D). For example, HSP72 showed 54% identity with the E. coli DnaK protein. The highest identity value was obtained from comparison with the Gram positive bacterium Lactococcus lactis, showing 85% identity with HSP72. Like other HSP70 proteins of Gram positive bacteria, HSP72 misses a stretch of 24 amino acids near the amino terminus when compared with DnaK proteins from Gram negative bacteria (FIGS. 13A–13D).

Although HSP72 shares homology with HSP70 (DnaK) proteins from other organisms, it does possess some unique features. Sequence divergence of the HSP70 (DnaK) proteins is largely localized to two regions (residues 244 to 330 and 510 to 607, SEQ ID NO:5). More specifically, the peptide sequences GFDAERDAAQAALDD (residues 527 to 541, SEQ ID NO:5) and AEGAQATGNAGDDVV (residues 586 to 600, SEQ ID NO:5) are exclusive to HSP72. The fact that the C-terminal portion of HSP72 is highly variable suggests that this portion carries antigenic determinants specific to S. pneumoniae. Consistent with this hypothesis, monoclonal antibodies directed against the C-169 fragment of HSP72 (infra), were not reactive with E. coli and S. aureus, which are known to express DnaK proteins similar to HSP72.

The truncated DnaJ protein of S. pneumoniae (SEQ ID NO:6) has 352 amino acids, which show a high degree of similarity with the corresponding portions of the L. lactis DnaJ protein (72% identity) and the E. coli DnaJ protein (51% identity). The predicted truncated DnaJ protein contains high glycine content (15%). Four Gly-, Cys-rich repeats, each with the Cys-X-X-Cys-X-Gly-X-Gly motif characteristic of DnaJ proteins [P. A. Silver and J. C. Way, Cell, 74, pp. 5–6 (1993)], were identified between amino acids 148 and 212 of the S. pneumoniae DnaJ protein (SEQ ID NO:6). Three repeated GGFGG sequences (residues 75–79, 81–85, and 90–94) were found near the N-terminus.

F. Reactivity of MAbs Against Recombinant Antigens

The four HSP72 specific MAbs (F1-Pn3.1, F2-Pn3.2, F2-Pn3.3 and F2-Pn3.4, supra) were tested for their reactivity against proteins expressed by E. coli infected or transformed with recombinant phages and plasmids containing HSP72 sequences. The four individual MAbs reacted with the lacZ-HSP72 fusion protein expressed by the clone λJBD7, thus localizing the epitopes recognized by these MAbs to the C-terminal 169 residues. Surprisingly, the proteins encoded by the pneumoccocal inserts in λJBD17 and pJBDΔ1 were recognized by only 3 of 4 Mabs. These results suggest that although the C-169 fragments synthesized in E. coli infected with λJBD7 and λJBD17 have the same primary structure, they have distinct conformation. The lack of reactivity of MAb F2-Pn3.2 with some recombinant proteins raised the possibility that this particular MAb recognizes a more complex epitope. Although complex, F2-Pn3.2 epitopes are still recognizable on Western immunoblots. The complete HSP72$_{rec}$ protein expressed by E. coli containing the recombinant plasmid pJBDΔ4 was reactive with all four MAbs.

Example 4—Antigenic Specificity and Reactivity of HSP72-Specific Monoclonal Antibodies The reactivity of MAbs F1-Pn3.1, F2-3.2, F2-Pn3.3 and F2-Pn3.4 to a collection of bacterial strains including 20 S. pneumoniae strains representing 16 capsular serotypes (types 1, 2, 3, 4, 5, 6, 8, 9, 10, 11, 12, 14, 15, 19, 20, and 22) and the 17 non-pneumococcal bacterial strains listed in Table 2, was tested using a dot enzyme immunoassay as described by D. Martin et al. [supra] and immunoblotting. For dot enzyme immunoassay, the bacteria were grown overnight on chocolate agar plates and then suspended in PBS, pH 7.4. A volume of 5 μl of a suspension containing approximately $10^9$ CFU/ml was applied to a nitrocellulose paper, blocked with PBS containing 3% bovine serum albumin, and then incubated sequentially with MAbs and peroxydase-labeled secondary antibody. Whole cell extracts were prepared for Western blot analysis by boiling bacterial suspensions in sample buffer for 5 minutes.

TABLE 2

LIST OF NON-PNEUMOCOCCAL ISOLATES TESTED BY DOT ENZYME IMMUNOASSAY

| Strain Designation | Genus species | group or type |
|---|---|---|
| C-2 | Streptococcus pyogenes | group A |
| C-3 | Streptococcus agalactiae | group B |
| C-7 | Enterococcus faecalis | group D |
| C-9 | Streptococcus bovis | group D |
| C-14 | Streptococcus mutans | |
| C-15 | Streptococcus salivarius | |
| C-19 | Streptococcus sanguis | I |
| C-20 | Streptococcus sanguis | I |
| C-21 | Streptococcus sanguis | I |

TABLE 2-continued

LIST OF NON-PNEUMOCOCCAL ISOLATES TESTED BY DOT ENZYME IMMUNOASSAY

| Strain Designation | Genus species | group or type |
|---|---|---|
| C-22 | Streptococcus sanguis | II |
| C-23 | Streptococcus sanguis | II |
| C-24 | Streptococcus sanguis | II |
| C-25 | Streptococcus sanguis | II |
| C-27 | Gemella morbillorum | |
| C-30 | Staphylococcus aureus | |
| C-33 | Bacillus | |
| C-36 | Escherichia coli | |

When tested by dot enzyme immunoassay, each MAb reacted with each of the *S. pneumoniae* strains and none of the non-pneumococcal isolates. These results were unexpected since comparison studies revealed that HSP72 is very similar to other known bacterial HSP70 (DnaK) proteins, for example those from *E. coli* and *S. aureus*.

Immunoblots were then performed to further investigate the immunoreactivities of our MAbs. As shown in Table 3, each MAb exhibited some reactivity.

Although the percent identity of the *E. coli* amino acid sequence and the HSP72 amino acid sequence (SEQ ID NO:5) is 54%, the four HSP72-specific MAbs did not recognize the *E. coli* HSP70 (DnaK) protein. Similarly, the HSP72-specific MAbs did not react with the *C. trachomatis* HSP70 (DnaK) protein, which has 560 amino acid identity with the amino acid sequence of HSP72. High amino acid sequence homology is observed between HSP72 and the HSP70 (DnaK) proteins from gram positive bacterial species. However, again, none of the HSP72-specific MAbs reacted with *S. aureaus* or Bacillus gram positive species, which exhibit 74% and 76% amino acid sequence homology, respectively, with HSP72. From these data it is clear that although HSP70 (DnaK) proteins may be structurally related to HSP72, they are immunologically distinct. Among the non-pneumococcal isolates that reacted with at least one MAb, there is *S. pyogenes, Enterococcus faecalis, S. mutans* and *S. sanguis*, which all belong to the Streptococcus or Streptococcus-related Enterococcus genus. So far, neither the HSP70 protein, nor the gene structure has been identified in these Streptococcus or Enterococcus species. Altogether, these observations indicate that hypervariable amino acid sequences or residues within HSP70 (DnaK) proteins are involved in antigenicity. Interestingly, immunoblotting analysis revealed that there was no significant variation in the molecular mass of the HSP70 (DnaK) proteins among both *S. pneumoniae* isolates and immunoreactive non-pneumococcal isolates.

TABLE 3

REACTIVITY OF MABS WITH NON-PNEUMOCOCCAL ISOLATES IN WESTERN IMMUNOBLOTTING

| Designation | Bacterial Strain | | MAbs | | | |
|---|---|---|---|---|---|---|
| | genus/species | type | F1-PN3.1 | F2-Pn3.2 | F2-PN3.3 | F2-Pn3.4 |
| C-2 | Streptococcus pyogenes | group A | − | + | − | ±[a] |
| C3 | Streptococcus agalactiae | group B | − | − | − | − |
| C-7 | Enterococcus faecalis | group D | − | + | − | − |
| C-9 | Streptococcus bovis | group D | − | − | − | − |
| C-14 | Streptococcus mutans | | − | + | − | ± |
| C-15 | Streptococcus salivarius | | − | − | − | − |
| C-19 | Streptococcus sanguis | I | + | + | − | − |
| C-20 | Streptococcus sanguis | I | + | + | − | + |
| C-21 | Streptococcus sanguis | I | + | + | + | + |
| C-22 | Streptococcus sanguis | II | + | + | + | + |
| C-23 | Streptococcus sanguis | II | + | + | − | − |
| C-24 | Streptococcus sanguis | II | + | + | + | + |
| C-25 | Streptococcus sanguis | II | + | + | + | + |
| C-27 | Gemella morbillorum | | − | − | − | − |
| C-30 | Staphylococcus aureus | | − | − | − | − |
| C-33 | Bacillus | | − | − | − | − |
| C-36 | Escherichia coli | | − | − | − | − |
| C-RP | Chlamydia trachomatis[b] | L2 | − | − | − | − |

[a] ± indicates a weak signal compared to the reactivity observed with *S. pneumoniae* antigens.
[b] *C. trachomatis* purified elementary bodies were tested.

Example 5—Purification of HSP72 And Its Use As An Immunogen to Protect Against Lethal *S. Pneumoniae* Infection A. Procedures 1. Preparation of Purified Recombinant HSP72 Protein and Recombinant C-169

High level exclusive expression of the HSP72 gene was achieved by employing the bacteriophage T7 RNA polymerase/T7 promoter system in *E. coli*. The 3.2 kb HindIII fragment was cloned in both orientations in front of the T7 promoter Φ10 in the plasmid pT7-5. The resulting plasmid pJBDk51 was then transformed into *E. coli* strain BL21 (DE3). Overexpression of the recombinant HSP72 protein ($HSP72_{rec}$) was induced by culturing in broth supplemented with antibiotics for a 3-hour period after the addition of IPTG to a final concentration of 1 mM. *E. coli* expressing high levels of $HSP72_{rec}$ were concentrated by centrifugation and lysed by mild sonication in 50 mM Tris-Cl (pH 8.0), 1 mM EDTA and 100 mM NaCl lysis buffer containing 0.2 mg/ml lysozyme. The cell lysates were centrifuged at 12,000 g for 15 minutes and the supernatants were collected. $HSP72_{rec}$ was purified by immunoaffinity using monoclonal antibody F1-Pn3.1 immobilized on sepharose 4B beads (Pharmacia). The purity of eluates was assessed on SDS-PAGE.

The recombinant C-169 protein ($C-169_{rec}$) was expressed in the form of insoluble inclusion bodies in *E. coli* strain JM109 transformed with the plasmid pJBDΔ1. Protein inclusion bodies were recovered from pelleted bacterial cells disrupted by sonication as described before. The pellets were washed in lysis buffer containing 1 mg/ml of deoxycholate to remove contaminating materials, and the protein inclusion bodies were then solubilized in urea 6M. The protein solution was centrifuged at 100,000 g and the cleared supernatant collected and dialysed against phosphate-buffered saline. After purification, the protein content was determined by the Bio-Rad protein assay (Bio-Rad Laboratories, Mississauga, Ontario, Canada).

2. Active Immunoprotection Studies

Two groups of 10 female Balb/c mice (Charles River Laboratories) were immunized subcutaneously three times at two-week intervals with 0.1 ml of purified HSP72$_{rec}$ or C-169$_{rec}$ antigens absorbed to Alhydrogel adjuvant. Two antigen doses, approximately 1 and 5 µg, were tested. A third group of 10 control mice were immunized identically via the same route with Alhydrogel adjuvant alone. Five to seven days following the third injection, all mice were bled and then challenged with approximately $10^6$ CFU of the type 3 S. pneumoniae strain WU2. Samples of the S. pneumoniae challenge inoculum were plated on chocolate agar plates to determine the CFU and to verify the challenge dose. Deaths were recorded at 6-hour intervals for the first 3–4 days post-infection and then at 24-hour intervals for a period of 14 days. On days 14 or 15, the surviving mice were sacrificed and blood samples tested for the presence of S. pneumoniae organisms.

3. Passive Immunoprotection Studies

One NZW rabbit (Charles River Laboratories) was immunized subcutaneously at multiple sites with approximately 50 µg of the purified C-169$_{rec}$ protein adsorbed to Alhydrogel adjuvant. The rabbit was boosted three times at two-week intervals with the same antigen and blood samples collected 7 and 14 days following the last immunization. The serum samples were pooled and antibodies were purified by precipitation using 40% saturated ammonium sulfate.

Severe-combined immunodeficient SCID mice were injected intraperitoneally with 0.25 ml of the purified rabbit antibodies 1 hour before intravenous challenge with 5000 or 880 CFU of the type 3 S. pneumoniae strain WU2. Control SCID mice received sterile buffer or antibodies purified from nonimmune rabbit sera. Samples of the S. pneumoniae challenge inoculum were plated on chocolate agar plates to determine the CFU and to verify the challenge dose. The SCID mice were chosen because of their high susceptibility to S. pneumoniae infection. Blood samples (20 µl each) obtained 24 hours post-challenge were plated on chocolate agar and tested for the presence of S. pneumoniae organisms. The level of detection was 50 CFU/ml. Deaths were recorded at 24-hour intervals for a period of 5 days.

B. Results

The availability of cloned S. pneumoniae DNA inserts encoding the complete or partial (C-169) HSP72 protein and the expression of recombinant proteins in E. coli allowed the obtention of purified proteins useful for the investigation of the vaccinogenic potential of HSP72 protein. Both HSP72$_{rec}$ and C-169$_{rec}$ proteins were obtained in a relatively pure state with no contaminants detected on Coomassie Blue-stained SDS polyacrylamide gels (FIGS. 14 and 15, respectively).

To evaluate the vaccinogenic potential of HSP72, we first examined the ability of HSP72$_{rec}$ to elicit a protective immune response. Groups of 10 mice were immunized with full-length HSP72$_{rec}$ (1 µg or 5 µg dose) and challenged with 4.2 million CFU of S. pneumoniae type 3 strain WU2. Eighty percent (80%) of the mice dosed with 1 µg HSP72$_{rec}$ survived the challenge, as did 50% of the mice dosed with 5 µg HSP72. None of the naive mice immunized with Alhydrogel adjuvant alone without antigen survived the challenge (FIG. 16). No S. pneumoniae organisms were detected in any of the blood samples collected on days 14 or 15 from mice surviving infection. The observation that HSP72 rec elicited protection against type 3 strain WU2 pneumococci indicated that HSP72 derived from DNA extracted from a type 6 strain contains epitopes capable of eliciting protection against a heterologous strain having a different capsular type.

We further examined the immune response to the HSP72 protein by using recombinant protein fragments expressed from E. coli transformed with a chimeric fucI-HSP72 gene. Mice immunized with purified C-169$_{rec}$ were protected from fatal pneumococcal challenge, thus demonstrating that some, if not all, epitopes eliciting protection are present in the C-terminal region of the HSP72 molecule comprising the last 169 residues. Groups of 10 mice were immunized with C-169$_{rec}$ (1 µg or 5 µg doses) and challenged with 6 million CFU of S. pneumoniae type 3 strain WU2. Sixty percent (60%) of the mice dosed with 1 µg C-169$_{rec}$ survived the challenge, as did 70% of the mice dosed with 5 µg C-169$_{rec}$ (FIG. 17). In contrast, all of the naive mice were dead by 2 days post-challenge. Therefore, the C-terminal portion of S. pneumoniae HSP72, which includes the region of maximum divergence among DnaK proteins, is a target for the protective immune response.

As illustrated in Table 4 below, two independent experiments demonstrated that SCID mice passively transferred with rabbit anti-C-169$_{rec}$ antibodies were protected from fatal infection with S. pneumoniae WU2. In contrast, none of the 15 control mice survived. The control mice received antibodies from nonimmune rabbit sera or received sterile buffer alone. In addition, all mice from the control groups had positive S. pneumoniae hemoculture 24 hours post-challenge, while S. pneumoniae organisms were detected in only 2 out of a total of 10 immunized SCID mice.

TABLE 4

PASSIVE IMMUNIZATION STUDIES SHOWING PROTECTION OF SCID MICE FROM EXPERIMENTAL S. PNEUMONIAE INFECTION BY ANTI-C-169$_{rec}$ RABBIT ANTIBODIES

| Experiment | Injection | No. of Mice Surviving Challenge after 5 days | No. of Mice Testing Positive for the Presence of S. pneumoniae |
|---|---|---|---|
| 1 | sterile buffer | 0/5 | 5/5 |
|  | anti-C-169$_{rec}$ | 4/5 | 2/5 |
|  | control antibodies | 0/5 | 5/5 |
| 2 | sterile buffer | 0/5 | 5/5 |
|  | anti-C-169$_{rec}$ | 5/5 | 0/5 |

In experiments 1 and 2 (Table 4), mice were challenged with 5000 and 880 CFU of type 3 S. pneumoniae strain WU2, respectively. Results in Table 4 are expressed as the number of mice surviving challenge, or testing positive for the presence of S. pneumoniae, compared to the total number of mice in each group.

Demonstration of the anti-HSP72 specificity of the antibody elicited by immunization with recombinant HSP72 or C-169 proteins came from Western Blot analyses using S. pneumoniae cell lysates as antigens. A single band corresponding to HSP72 was detected by all rabbit and mouse antisera tested. These serologic results suggested that the protection following the immunization with recombinant proteins was due to the production of antibodies reactive with *S. pneumoniae* HSP72.

Example 6—Use of HSP72 as a Human Vaccine

To formulate a vaccine for human use, appropriate HSP72 antigens may be selected from the polypeptides described herein. For example, one of skill in the art could design a vaccine around the HSP72 polypeptide or fragments thereof containing an immunogenic epitope. The use of molecular biology techniques is particularly well-suited for the preparation of substantially pure recombinant antigens.

The vaccine composition may take a variety of forms. These include, for example solid, semi-solid and liquid dosage forms, such as powders, liquid solutions or suspensions, and liposomes. Based on our belief that the HSP72 antigens of this invention may elicit a protective immune response when administered to a human, the compositions of this invention will be similar to those used for immunizing humans with other proteins and polypeptides, e.g. tetanus and diphtheria. Therefore, the compositions of this invention will preferably comprise a pharmaceutcially acceptable adjuvant such as incomplete Freund's adjuvant, aluminum hydroxide, a muramyl peptide, a water-in oil emulsion, a liposome, an ISCOM or CTB, or a non-toxic B subunit from cholera toxin. Most preferably, the compositions will include a water-in-oil emulsion or aluminum hydroxide as adjuvant.

The composition would be administered to the patient in any of a number of pharmaceutically acceptable forms including intramuscular, intradermal, subcutaneous or topic. Preferably, the vaccine will be administered intramuscularly.

Generally, the dosage will consist of an initial injection, most probably with adjuvant, of about 0.01 to 10 mg, and preferably 0.1 to 1.0 mg HSP72 antigen per patient, followed most probably by one or more booster injections. Preferably, boosters will be administered at about 1 and 6 months after the initial injection.

An important consideration relating to pneumococcal vaccine development is the question of mucosal immunity. The ideal mucosal vaccine will be safely taken orally or intranasally as one or a few doses and would elicit protective antibodies on the appropriate surfaces along with systemic immunity. The mucosal vaccine composition may include adjuvants, inert particulate carriers or recombinant live vectors.

The anti-HSP72 antibodies of this invention are useful for passive immunotherapy and immunoprophylaxis of humans infected with *S. pneumoniae* or related bacteria. The dosage forms and regimens for such passive immunization would be similar to those of other passive immunotherapies.

An antibody according to this invention is exemplified by a hybridoma producing MAb F1-Pn3.1 deposited in the American Type Culture Collection in Rockville, Md., USA on [date], and identified as [insert name]. This deposit was assigned accession number [fill in when assigned].

While we have described herein a number of embodiments of this invention, it is apparent that our basic embodiments may be altered to provide other embodiments that utilize the compositions and processes of this invention. Therefore, it will be appreciated that the scope of this invention includes all alternative embodiments and variations that are defined in the foregoing specification and by the claim appended hereto; and the invention is not to be limited by the specific embodiments which have been presented herein by way of example.

---

We claim:

1. An isolated and purified *Streptococcus pneumoniae* heat shock protein having a molecular weight of about 72 kDa as measured by SDS-PAGE.

2. An isolated and purified protein according to claim 1, comprising amino acid sequence SEQ ID NO:5.

3. An isolated and purified protein according to claim 2, consisting of amino acid sequence SEQ ID NO:5.

4. An isolated and purified immunogenic polypeptide comprising an amino acid sequence chosen from the group consisting of:

SEQ ID NO: 5;

residues 527 to 541 of SEQ ID NO:5 or an immunogenic fragment thereof;

residues 510 to 607 of SEQ ID NO:5 or an immunogenic fragment thereof;

residues 439 to 607 of SEQ ID NO:5 or an immunogenic fragment thereof;

residues 586 to 600 of SEQ ID NO:5 or an immunogenic fragment thereof; and residues 244 to 330 of SEQ ID NO:5 or an immunogenic fragment thereof;

wherein said polypeptide generates a monoclonal antibody not reactive with *E. coli* or *S. aureus*.

* * * * *

SEQUENCE LISTING

```
(1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 3167 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae (ix) FEATURE:
        (A) NAME/KEY: CDS
        (B) LOCATION: 30..755

(ix) FEATURE:
        (A) NAME/KEY: CDS
        (B) LOCATION: 771..2912
        (D) OTHER INFORMATION: /product= "FucI/HSP72 (C-169)"

(xi) SEQUENCE DESCRIPTION: SEQ ID NO:1:
```

```
GAACTTCATT TTTAGAAAGG AGTGAGTTT ATG TCT CAA GAT GAA AAA TTA ATT          53
                                Met Ser Gln Asp Glu Lys Leu Ile
                                 1               5

CGT GAA CAG ATT TGT GAT GTT TGT CAT AAG ATG TGG CAA CTT GGT TGG         101
Arg Glu Gln Ile Cys Asp Val Cys His Lys Met Trp Gln Leu Gly Trp
         10              15                  20

GTT GCT GCT AAC GAT GGG AAT GTA TCT GTT CGA TTA GAT GAG GAT ACC         149
Val Ala Ala Asn Asp Gly Asn Val Ser Val Arg Leu Asp Glu Asp Thr
 25              30                  35                  40

ATT CTT GCA ACA CCT ACT GGT ATC AGC AAA AGT TTT ATT ACA CCA GAA         197
Ile Leu Ala Thr Pro Thr Gly Ile Ser Lys Ser Phe Ile Thr Pro Glu
                 45                  50                  55

AAG CTG GTG AAG TTA AAT CTT AAA GGA GAG ATT TTA GAA GCA GAA GGT         245
Lys Leu Val Lys Leu Asn Leu Lys Gly Glu Ile Leu Glu Ala Glu Gly
             60                  65                  70

GAT TAC TGT CCT TCT AGT GAA ATT AAA ATG CAC ATT CGG TGC TAC GAA         293
Asp Tyr Cys Pro Ser Ser Glu Ile Lys Met His Ile Arg Cys Tyr Glu
         75                  80                  85

GAA CGT GAG GAT GTT CGT TCA GTT GTT CAC GCG CAT CCA CCG ATT GCA         341
Glu Arg Glu Asp Val Arg Ser Val Val His Ala His Pro Pro Ile Ala
     90                  95                 100

ACA GGA TTT GCT CTT GCA CAC ATT CCT TTA GAT ACT TAT TCA CTA ATT         389
Thr Gly Phe Ala Leu Ala His Ile Pro Leu Asp Thr Tyr Ser Leu Ile
105             110                 115                 120

GAG AGC GCG ATT GTG GTT GGG GCA ATT CCT ATT ACC CCA TTT GGA GTA         437
Glu Ser Ala Ile Val Val Gly Ala Ile Pro Ile Thr Pro Phe Gly Val
                125                 130                 135

CCG TCT ACA ATG GAA GTG CCA GAA GCA ATT ACA CCT TAT CTG CCC GAT         485
Pro Ser Thr Met Glu Val Pro Glu Ala Ile Thr Pro Tyr Leu Pro Asp
            140                 145                 150

CAT GAT GTC ATG CTA TTA GAA AAT CAT GGA GCT CTG ACT GTC GGA AGC         533
His Asp Val Met Leu Leu Glu Asn His Gly Ala Leu Thr Val Gly Ser
        155                 160                 165

GAT GTC ATT ACA GCA TAC TAC CGT ATG GAA ACT TTA GAA TTA GTC GCA         581
Asp Val Ile Thr Ala Tyr Tyr Arg Met Glu Thr Leu Glu Leu Val Ala
    170                 175                 180

AAG ACA ACC TTC CAC GGA AGA ATG TTA CTT TCT ACA AAG GGC ATT GAG         629
Lys Thr Thr Phe His Gly Arg Met Leu Leu Ser Thr Lys Gly Ile Glu
185                 190                 195                 200

GAG CAA GAA ATT GCT CGT CCG ACT TTA GAA CGT CTA TTC TCA ATG CGA         677
Glu Gln Glu Ile Ala Arg Pro Thr Leu Glu Arg Leu Phe Ser Met Arg
                205                 210                 215

GAA AAT TAT AAG GTT ACA GGT CGT CAC CCA GGC TAC CGT AAA TAT AAT         725
Glu Asn Tyr Lys Val Thr Gly Arg His Pro Gly Tyr Arg Lys Tyr Asn
            220                 225                 230

GGC GAT GGT AGT ATA AAA GAA ACA AAA AAA TAAGAGGAAA GTATT ATG ATC        776
Gly Asp Gly Ser Ile Lys Glu Thr Lys Lys                  Met Ile
        235                 240                           1

CAA CAT CCA CGT ATT GGG ATT CGT CCG ACT ATT GAT GGT CGT CGT CAA         824
Gln His Pro Arg Ile Gly Ile Arg Pro Thr Ile Asp Gly Arg Arg Gln
          5                  10                  15

GGT GTA CGC GAA TCA CTT GAA GTA CAA ACA ATG AAC ATG GCT AAA AGT         872
Gly Val Arg Glu Ser Leu Glu Val Gln Thr Met Asn Met Ala Lys Ser
     20                  25                  30

GTG GCA GAT TTG ATT TCA AGC ACA TTG AAA TAT CCA GAT GGG GAA CCT         920
Val Ala Asp Leu Ile Ser Ser Thr Leu Lys Tyr Pro Asp Gly Glu Pro
 35                  40                  45                  50

GTG GAA TGT GTG ATT TCT CCA TCT ACC ATT GGT CGT GTT CCA GAG GCT         968
Val Glu Cys Val Ile Ser Pro Ser Thr Ile Gly Arg Val Pro Glu Ala
             55                  60                  65
```

```
GCA GCT TCC CAT GAG TTG TTT AAA AAA TCA AAT GTT TGC GCA ACA ATT      1016
Ala Ala Ser His Glu Leu Phe Lys Lys Ser Asn Val Cys Ala Thr Ile
             70                  75                  80

ACA GTT ACA CCA TGC TGG TGT TAT GGT AGT GAA ACT ATG GAT ATG TCT      1064
Thr Val Thr Pro Cys Trp Cys Tyr Gly Ser Glu Thr Met Asp Met Ser
             85                  90                  95

CCA GAT ATT CCT CAT GCT ATT TGG GGA TTT AAT GGG ACA GAA CGC CCA      1112
Pro Asp Ile Pro His Ala Ile Trp Gly Phe Asn Gly Thr Glu Arg Pro
100                 105                 110

GGA GCT GTC TAT CTT GCA GCT GTA CTA GCT TCA CAT ACT CAA AAA GGG      1160
Gly Ala Val Tyr Leu Ala Ala Val Leu Ala Ser His Thr Gln Lys Gly
115                 120                 125                 130

ATT CCA GCC TTT GGG ATT TAT GGT AGA GAT GTT CAG GAA GCT AAT GAT      1208
Ile Pro Ala Phe Gly Ile Tyr Gly Arg Asp Val Gln Glu Ala Asn Asp
                135                 140                 145

ACA GCT ATT CCA GAA GAT GTC AAA GAA AAA CTT TTA CGT TAT GCG CGG      1256
Thr Ala Ile Pro Glu Asp Val Lys Glu Lys Leu Leu Arg Tyr Ala Arg
                150                 155                 160

GCA GTT CTT GCA ACT GGC TTG ATG AGA GAC ACT GCT TAC CTA TCA ATG      1304
Ala Val Leu Ala Thr Gly Leu Met Arg Asp Thr Ala Tyr Leu Ser Met
             165                 170                 175

GGT AGT GTT TCG ATG GGG ATT GGT GGT TCT ATT GTA AAT CCA GAT TTC      1352
Gly Ser Val Ser Met Gly Ile Gly Gly Ser Ile Val Asn Pro Asp Phe
180                 185                 190

TTC CAA GAA TAC TTA GGA ATG CGA AAT GAA TCG GTA GAT ATG ACG GAG      1400
Phe Gln Glu Tyr Leu Gly Met Arg Asn Glu Ser Val Asp Met Thr Glu
195                 200                 205                 210

TTC ACG CGC CGT ATG GAC CGT GGT ATT TAC GAC CCT GAA GAG TTC GAA      1448
Phe Thr Arg Arg Met Asp Arg Gly Ile Tyr Asp Pro Glu Glu Phe Glu
                215                 220                 225

CGT GCG CTC AAA TGG GTG AAA GAA AAC GTA AAA GAA GGA TTC GAC CAT      1496
Arg Ala Leu Lys Trp Val Lys Glu Asn Val Lys Glu Gly Phe Asp His
                230                 235                 240

AAC CGT GAA GAC CTT GTT TTA AGC CGT GAA GAA AAA GAT AGA CAA TGG      1544
Asn Arg Glu Asp Leu Val Leu Ser Arg Glu Glu Lys Asp Arg Gln Trp
             245                 250                 255

GAA TTT GTT ATT AAG ATG TTC ATG ATT GGA CGT GAC TTA ATG GTT GGT      1592
Glu Phe Val Ile Lys Met Phe Met Ile Gly Arg Asp Leu Met Val Gly
260                 265                 270

AAC CCA AGA CTT GCT GAA CTT GGT TTT GAG GAA GAA GCA GTT GGT CAC      1640
Asn Pro Arg Leu Ala Glu Leu Gly Phe Glu Glu Glu Ala Val Gly His
275                 280                 285                 290

CAT GCT TTA GTA GCT GGT TTC CAA GGT CAA CGT CAG TGG ACA GAC CAT      1688
His Ala Leu Val Ala Gly Phe Gln Gly Gln Arg Gln Trp Thr Asp His
                295                 300                 305

TTT CCA AAT GGG GAC TTT ATG GAA ACT TTC CTC AAT ACT CAG TTT GAC      1736
Phe Pro Asn Gly Asp Phe Met Glu Thr Phe Leu Asn Thr Gln Phe Asp
                310                 315                 320

TGG AAT GGT ATT CGA AAA CCA TTT GTA TTT GCG ACA GAG AAT GAT TCA      1784
Trp Asn Gly Ile Arg Lys Pro Phe Val Phe Ala Thr Glu Asn Asp Ser
             325                 330                 335

CTA AAT GGT GTG TCT ATG CTC TTT AAT TAT CTA TTA ACA AAT ACT CCA      1832
Leu Asn Gly Val Ser Met Leu Phe Asn Tyr Leu Leu Thr Asn Thr Pro
340                 345                 350

CAA ATC TTT GCT GAT GTG CGT ACT TAT TGG AGT CCA GAG GCT GTT GAA      1880
Gln Ile Phe Ala Asp Val Arg Thr Tyr Trp Ser Pro Glu Ala Val Glu
355                 360                 365                 370

CGT GTA ACA GGA TAT ACT TTA GAG GGT CGT GCT GCA GCT GGA TTC TTA      1928
Arg Val Thr Gly Tyr Thr Leu Glu Gly Arg Ala Ala Ala Gly Phe Leu
                375                 380                 385
```

```
CAT CTA ATC AAC TCT GGA TCT TGT ACA TTG GAT GGT ACA GGT CAA GCT        1976
His Leu Ile Asn Ser Gly Ser Cys Thr Leu Asp Gly Thr Gly Gln Ala
            390                 395                 400

ACT CGA GAT GGC AAA CCT GTT ATG AAA CCA TTC TGG GAG TTG GAT GAA        2024
Thr Arg Asp Gly Lys Pro Val Met Lys Pro Phe Trp Glu Leu Asp Glu
                405                 410                 415

AGT GAA GTA CAG GCT ATG CTT GAA AAT ACA GAC TTC CCA CCA GCA AAC        2072
Ser Glu Val Gln Ala Met Leu Glu Asn Thr Asp Phe Pro Pro Ala Asn
    420                 425                 430

CGC GAA TAC TTC CGT GGA GGA GGA TTC TCA ACT CGT TTC TTG ACG AAG        2120
Arg Glu Tyr Phe Arg Gly Gly Gly Phe Ser Thr Arg Phe Leu Thr Lys
435                 440                 445                 450

GGG GAT ATG CCA GTA ACA ATG GTA CGT CTC AAT CTT TTA AAA GGG GTT        2168
Gly Asp Met Pro Val Thr Met Val Arg Leu Asn Leu Leu Lys Gly Val
                455                 460                 465

GGT CCA GTG CTA CAA ATT GCA GAA GGT TAC ACA CTT GAA CTT CCT GAA        2216
Gly Pro Val Leu Gln Ile Ala Glu Gly Tyr Thr Leu Glu Leu Pro Glu
        470                 475                 480

GAT GTT CAC CAT ACT TTA GAT AAT CGT ACA GAT CCA GGA TGG CCA ACT        2264
Asp Val His His Thr Leu Asp Asn Arg Thr Asp Pro Gly Trp Pro Thr
            485                 490                 495

ACT TGG TTT GCT CCA CGT TTG ACA GGA AAA GGT GCT TTC AAG TCT GTC        2312
Thr Trp Phe Ala Pro Arg Leu Thr Gly Lys Gly Ala Phe Lys Ser Val
                500                 505                 510

TAT GAC GTC ATG AAT AAT TGG GGA GCT AAT CAC GGA GCC ATA ACA TAT        2360
Tyr Asp Val Met Asn Asn Trp Gly Ala Asn His Gly Ala Ile Thr Tyr
515                 520                 525                 530

GGA CAC ATT GGA GCA GAC TTG ATT ACC TTG GCT TCT ATG TTG AGA ATT        2408
Gly His Ile Gly Ala Asp Leu Ile Thr Leu Ala Ser Met Leu Arg Ile
                535                 540                 545

CCT CAA ATC GAA GTA ACA TTT GAC ATC GAC AAG AAC GGT ATC GTG TCT        2456
Pro Gln Ile Glu Val Thr Phe Asp Ile Asp Lys Asn Gly Ile Val Ser
            550                 555                 560

GTT AAG GCC AAA GAC CTT GGA ACT CAA AAA GAA CAA ACT ATT GTC ATC        2504
Val Lys Ala Lys Asp Leu Gly Thr Gln Lys Glu Gln Thr Ile Val Ile
                565                 570                 575

CAA TCG AAC TCA GGT TTG ACT GAC GAA GAA ATC GAC CGC ATG ATG AAA        2552
Gln Ser Asn Ser Gly Leu Thr Asp Glu Glu Ile Asp Arg Met Met Lys
        580                 585                 590

GAT GCA GAA GCA AAC GCT GAA TCC GAT AAG AAA CGT AAA GAA GAA GTA        2600
Asp Ala Glu Ala Asn Ala Glu Ser Asp Lys Lys Arg Lys Glu Glu Val
595                 600                 605                 610

GAC CTT CGT AAT GAA GTG GAC CAA GCA ATC TTT GCG ACT GAA AAG ACA        2648
Asp Leu Arg Asn Glu Val Asp Gln Ala Ile Phe Ala Thr Glu Lys Thr
                615                 620                 625

ATC AAG GAA ACT GAA GGT AAA GGC TTC GAC GCA GAA CGT GAC GCT GCC        2696
Ile Lys Glu Thr Glu Gly Lys Gly Phe Asp Ala Glu Arg Asp Ala Ala
            630                 635                 640

CAA GCT GCC CTT GAT GAC CTT AAG AAA GCT CAA GAA GAC AAC AAC TTG        2744
Gln Ala Ala Leu Asp Asp Leu Lys Lys Ala Gln Glu Asp Asn Asn Leu
                645                 650                 655

GAC GAC ATG AAA GCA AAA CTT GAA GCA TTG AAC GAA AAA GCT CAA GGA        2792
Asp Asp Met Lys Ala Lys Leu Glu Ala Leu Asn Glu Lys Ala Gln Gly
        660                 665                 670

CTT GCT GTT AAA CTC TAC GAA CAA GCC GCA GCA GCG CAA CAA GCT CAA        2840
Leu Ala Val Lys Leu Tyr Glu Gln Ala Ala Ala Ala Gln Gln Ala Gln
675                 680                 685                 690

GAA GGA GCA GAA GGC GCA CAA GCA ACA GGA AAC GCA GGC GAT GAC GTC        2888
Glu Gly Ala Glu Gly Ala Gln Ala Thr Gly Asn Ala Gly Asp Asp Val
                695                 700                 705
```

```
GTA GAC GGA GAG TTT ACG GAA AAG TAAGATGAGT GTATTGGATG AAGAGTATCT    2942
Val Asp Gly Glu Phe Thr Glu Lys
                710

AAAAAATACA CGAAAAGTTT ATAATGATTT TTGTAATCAA GCTGATAACT ATAGAACATC    3002

AAAAGATTTT ATTGATAATA TTCCAATAGA ATATTTAGCT AGATATAGAG AAATTATATT    3062

AGCTGAGCAT GATAGTTGTG TCAAAAATGA TGAAGCGGTA AGGAATTTTG TTACCTCAGT    3122

ATTGTTGTCT GCATTTGTAT CGGCGATGGT ATCAGCTATG ATATC                    3167

(2) INFORMATION FOR SEQ ID NO:2:

(i) SEQUENCE CHARACTERISTICS:
        (A) LENGTH: 242 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Gln Asp Glu Lys Leu Ile Arg Glu Gln Ile Cys Asp Val Cys
1               5                   10                  15

His Lys Met Trp Gln Leu Gly Trp Val Ala Ala Asn Asp Gly Asn Val
            20                  25                  30

Ser Val Arg Leu Asp Glu Asp Thr Ile Leu Ala Thr Pro Thr Gly Ile
        35                  40                  45

Ser Lys Ser Phe Ile Thr Pro Glu Lys Leu Val Lys Leu Asn Leu Lys
    50                  55                  60

Gly Glu Ile Leu Glu Ala Glu Gly Asp Tyr Cys Pro Ser Ser Glu Ile
65                  70                  75                  80

Lys Met His Ile Arg Cys Tyr Glu Glu Arg Glu Asp Val Arg Ser Val
                85                  90                  95

Val His Ala His Pro Pro Ile Ala Thr Gly Phe Ala Leu Ala His Ile
            100                 105                 110

Pro Leu Asp Thr Tyr Ser Leu Ile Glu Ser Ala Ile Val Val Gly Ala
        115                 120                 125

Ile Pro Ile Thr Pro Phe Gly Val Pro Ser Thr Met Glu Val Pro Glu
    130                 135                 140

Ala Ile Thr Pro Tyr Leu Pro Asp His Asp Val Met Leu Leu Glu Asn
145                 150                 155                 160

His Gly Ala Leu Thr Val Gly Ser Asp Val Ile Thr Ala Tyr Tyr Arg
                165                 170                 175

Met Glu Thr Leu Glu Leu Val Ala Lys Thr Thr Phe His Gly Arg Met
            180                 185                 190

Leu Leu Ser Thr Lys Gly Ile Glu Glu Gln Glu Ile Ala Arg Pro Thr
        195                 200                 205

Leu Glu Arg Leu Phe Ser Met Arg Glu Asn Tyr Lys Val Thr Gly Arg
    210                 215                 220

His Pro Gly Tyr Arg Lys Tyr Asn Gly Asp Gly Ser Ile Lys Glu Thr
225                 230                 235                 240

Lys Lys (2) INFORMATION FOR SEQ ID NO:3:

(i) SEQUENCE CHARACTERISTICS:
        (A) LENGTH: 714 amino acids
        (B) TYPE: amino acid
        (D) TOPOLOGY: linear
```

(ii) MOLECULE TYPE: protein (xi) SEQUENCE DESCRIPTION: SEQ ID NO:3:

```
Met Ile Gln His Pro Arg Ile Gly Ile Arg Pro Thr Ile Asp Gly Arg
 1               5                  10                  15

Arg Gln Gly Val Arg Glu Ser Leu Glu Val Gln Thr Met Asn Met Ala
                20                  25                  30

Lys Ser Val Ala Asp Leu Ile Ser Ser Thr Leu Lys Tyr Pro Asp Gly
            35                  40                  45

Glu Pro Val Glu Cys Val Ile Ser Pro Ser Thr Ile Gly Arg Val Pro
        50                  55                  60

Glu Ala Ala Ser His Glu Leu Phe Lys Lys Ser Asn Val Cys Ala
65                  70                  75                  80

Thr Ile Thr Val Thr Pro Cys Trp Cys Tyr Gly Ser Glu Thr Met Asp
                85                  90                  95

Met Ser Pro Asp Ile Pro His Ala Ile Trp Gly Phe Asn Gly Thr Glu
                100                 105                 110

Arg Pro Gly Ala Val Tyr Leu Ala Ala Val Leu Ala Ser His Thr Gln
            115                 120                 125

Lys Gly Ile Pro Ala Phe Gly Ile Tyr Gly Arg Asp Val Gln Glu Ala
130                 135                 140

Asn Asp Thr Ala Ile Pro Glu Asp Val Lys Lys Leu Leu Arg Tyr
145                 150                 155                 160

Ala Arg Ala Val Leu Ala Thr Gly Leu Met Arg Asp Thr Ala Tyr Leu
                165                 170                 175

Ser Met Gly Ser Val Ser Met Gly Ile Gly Gly Ser Ile Val Asn Pro
                180                 185                 190

Asp Phe Phe Gln Glu Tyr Leu Gly Met Arg Asn Glu Ser Val Asp Met
            195                 200                 205

Thr Glu Phe Thr Arg Arg Met Asp Arg Gly Ile Tyr Asp Pro Glu Glu
        210                 215                 220

Phe Glu Arg Ala Leu Lys Trp Val Lys Glu Asn Val Lys Glu Gly Phe
225                 230                 235                 240

Asp His Asn Arg Glu Asp Leu Val Leu Ser Arg Glu Glu Lys Asp Arg
                245                 250                 255

Gln Trp Glu Phe Val Ile Lys Met Phe Met Ile Gly Arg Asp Leu Met
                260                 265                 270

Val Gly Asn Pro Arg Leu Ala Glu Leu Gly Phe Glu Glu Glu Ala Val
            275                 280                 285

Gly His His Ala Leu Val Ala Gly Phe Gln Gly Gln Arg Gln Trp Thr
        290                 295                 300

Asp His Phe Pro Asn Gly Asp Phe Met Glu Thr Phe Leu Asn Thr Gln
305                 310                 315                 320

Phe Asp Trp Asn Gly Ile Arg Lys Pro Phe Val Phe Ala Thr Glu Asn
                325                 330                 335

Asp Ser Leu Asn Gly Val Ser Met Leu Phe Asn Tyr Leu Leu Thr Asn
                340                 345                 350

Thr Pro Gln Ile Phe Ala Asp Val Arg Thr Tyr Trp Ser Pro Glu Ala
            355                 360                 365

Val Glu Arg Val Thr Gly Tyr Thr Leu Glu Gly Arg Ala Ala Ala Gly
        370                 375                 380

Phe Leu His Leu Ile Asn Ser Gly Ser Cys Thr Leu Asp Gly Thr Gly
385                 390                 395                 400
```

```
Gln Ala Thr Arg Asp Gly Lys Pro Val Met Lys Pro Phe Trp Glu Leu
            405                 410                 415
Asp Glu Ser Glu Val Gln Ala Met Leu Glu Asn Thr Asp Phe Pro Pro
            420                 425                 430
Ala Asn Arg Glu Tyr Phe Arg Gly Gly Phe Ser Thr Arg Phe Leu
            435                 440                 445
Thr Lys Gly Asp Met Pro Val Thr Met Val Arg Leu Asn Leu Leu Lys
        450                 455                 460
Gly Val Gly Pro Val Leu Gln Ile Ala Glu Gly Tyr Thr Leu Glu Leu
465                     470                 475                 480
Pro Glu Asp Val His His Thr Leu Asp Asn Arg Thr Asp Pro Gly Trp
                    485                 490                 495
Pro Thr Thr Trp Phe Ala Pro Arg Leu Thr Gly Lys Gly Ala Phe Lys
            500                 505                 510
Ser Val Tyr Asp Val Met Asn Asn Trp Gly Ala Asn His Gly Ala Ile
            515                 520                 525
Thr Tyr Gly His Ile Gly Ala Asp Leu Ile Thr Leu Ala Ser Met Leu
        530                 535                 540
Arg Ile Pro Gln Ile Glu Val Thr Phe Asp Ile Asp Lys Asn Gly Ile
545                     550                 555                 560
Val Ser Val Lys Ala Lys Asp Leu Gly Thr Gln Lys Glu Gln Thr Ile
            565                 570                 575
Val Ile Gln Ser Asn Ser Gly Leu Thr Asp Glu Glu Ile Asp Arg Met
            580                 585                 590
Met Lys Asp Ala Glu Ala Asn Ala Glu Ser Asp Lys Lys Arg Lys Glu
        595                 600                 605
Glu Val Asp Leu Arg Asn Glu Val Asp Gln Ala Ile Phe Ala Thr Glu
            610                 615                 620
Lys Thr Ile Lys Glu Thr Glu Gly Lys Gly Phe Asp Ala Glu Arg Asp
625                     630                 635                 640
Ala Ala Gln Ala Ala Leu Asp Asp Leu Lys Lys Ala Gln Glu Asp Asn
                    645                 650                 655
Asn Leu Asp Asp Met Lys Ala Lys Leu Glu Ala Leu Asn Glu Lys Ala
            660                 665                 670
Gln Gly Leu Ala Val Lys Leu Tyr Glu Gln Ala Ala Ala Gln Gln
            675                 680                 685
Ala Gln Glu Gly Ala Glu Gly Ala Gln Ala Thr Gly Asn Ala Gly Asp
            690                 695                 700
Asp Val Val Asp Gly Glu Phe Thr Glu Lys
705                     710
```

(2) INFORMATION FOR SEQ ID NO:4:

(i) SEQUENCE CHARACTERISTICS:
        (A) LENGTH: 4320 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Streptococcus pneumoniae (ix) FEATURE:
        (A) NAME/KEY: CDS
        (B) LOCATION: 3265..4320
        (D) OTHER INFORMATION: /product= "NH2-terminal portion of
            DNA J"

(ix) FEATURE:
        (A) NAME/KEY: CDS
        (B) LOCATION: 682..2502
        (D) OTHER INFORMATION: /product= "Heat-Shock Protein 72"

(ix) FEATURE:
        (A) NAME/KEY: mat_peptide
        (B) LOCATION: 682..2502

(xi) SEQUENCE DESCRIPTION: SEQ ID NO:4:

```
AAGCTTGATT CACGCTTTGA AGAAGAAGG AATTGAAGAA ATCGCAGCAG ATGGCGAATT      60

TGACCATAAC TACCATATGG CCATCCAAAC TCTCCCAGCA GACGATGAAC ACCCAGTAGA    120

TACCATCGCC CAAGTCTTTC AAAAAGGCTA CAAACTCCAT GACCGCATCC TACGCCCAGC    180

AATGGTAGTG GTGTATAACT AAGATACAAA GCCCGTAAAA AGCTCGCAGT AAAAATAGGA    240

GATTGACGAA GTGTTCGATG AACACAAGAA ATCTATCTT TTTTACTCAG AGCTTAGGGC     300

GTGTTCGATT CGGCAATTCT GACGGTAGCT AAAGCAACTC GTCAGAAAAC GGCAGTCGCT    360

ATGGCGTTTG TCTAGCTTCC TTACTAACTC GTCGTCGAAA TAAAATCGAT TTCGACTCTT    420

CGTGTCGCAA TTTACATAAT AGAAACTTG TCCGAAACGA CAATAAACTA TGAAGAAAGA     480

TAAAATATGT TTGGCTTTGT AATAGTGAGC GAAGCGAACC AAAGACGATA CTCTTCGCTG    540

TGGCGCTATT TGCGCAAATT TTGAGACCTT AGGCTCAAAG TTTAGTCAAA GAGATTGACA    600

AAGTCAAGCT CTGACGGCGT CGCCACTTAA GAAGAGTATC AAAAGAAAA ATAGAAAATT     660

AACTAACAAG GAGAAAAACA C ATG TCT AAA ATT ATC GGT ATT GAC TTA GGT      711
                         Met Ser Lys Ile Ile Gly Ile Asp Leu Gly
                           1               5                  10

ACA ACA AAC TCA GCA GTT GCA GTT CTT GAA GGA ACT GAA AGC AAA ATC      759
Thr Thr Asn Ser Ala Val Ala Val Leu Glu Gly Thr Glu Ser Lys Ile
                15                  20                  25

ATC GCA AAC CCA GAA GGA AAC CGC ACA ACT CCA TCT GTA GTC TCA TTC      807
Ile Ala Asn Pro Glu Gly Asn Arg Thr Thr Pro Ser Val Val Ser Phe
        30                  35                  40

AAA AAC GGA GAA ATC ATC GTT GGT GAT GCT GCA AAA CGT CAA GCA GTT      855
Lys Asn Gly Glu Ile Ile Val Gly Asp Ala Ala Lys Arg Gln Ala Val
    45                  50                  55

ACA AAC CCA GAT ACA GTT ATC TCT ATC AAA TCT AAG ATG GGA ACT TCT      903
Thr Asn Pro Asp Thr Val Ile Ser Ile Lys Ser Lys Met Gly Thr Ser
60                  65                  70

GAA AAA GTT TCT GCA AAT GGA AAA GAA TAC ACT CCA CAA GAA ATC TCA      951
Glu Lys Val Ser Ala Asn Gly Lys Glu Tyr Thr Pro Gln Glu Ile Ser
75                  80                  85                  90

GCT ATG ATC CTT CAA TAC TTG AAA GGC TAC GCT GAA GAC TAC CTT GGT      999
Ala Met Ile Leu Gln Tyr Leu Lys Gly Tyr Ala Glu Asp Tyr Leu Gly
                95                 100                 105

GAG AAA GTA ACC AAA GCT GTT ATC ACA GTT CCG GCT TAC TTC AAC GAC     1047
Glu Lys Val Thr Lys Ala Val Ile Thr Val Pro Ala Tyr Phe Asn Asp
            110                 115                 120

GCT CAA CGT CAA GCA ACA AAA GAC GCT GGT AAA ATT GCT GGT CTT GAA     1095
Ala Gln Arg Gln Ala Thr Lys Asp Ala Gly Lys Ile Ala Gly Leu Glu
        125                 130                 135

GTA GAA CGT ATT GTT AAC GAA CCA ACT GCA GCA GCT CTT GCT TAT GGT     1143
Val Glu Arg Ile Val Asn Glu Pro Thr Ala Ala Ala Leu Ala Tyr Gly
    140                 145                 150
```

```
TTG GAC AAG ACT GAC AAA GAA GAA AAA ATC TTG GTA TTT GAC CTT GGT      1191
Leu Asp Lys Thr Asp Lys Glu Glu Lys Ile Leu Val Phe Asp Leu Gly
155                 160                 165                 170

GGT GGT ACA TTC GAC GTC TCT ATC CTT GAA TTG GGT GAC GGT GTC TTC      1239
Gly Gly Thr Phe Asp Val Ser Ile Leu Glu Leu Gly Asp Gly Val Phe
                175                 180                 185

GAC GTA TTG TCA ACT GCA GGG GAC AAC AAA CTT GGT GGT GAC GAC TTT      1287
Asp Val Leu Ser Thr Ala Gly Asp Asn Lys Leu Gly Gly Asp Asp Phe
            190                 195                 200

GAC CAA AAA ATC ATT GAC CAC TTG GTA GCA GAA TTC AAG AAA GAA AAC      1335
Asp Gln Lys Ile Ile Asp His Leu Val Ala Glu Phe Lys Lys Glu Asn
        205                 210                 215

GGT ATC GAC TTG TCT ACT GAC AAG ATG GCA ATG CAA CGT TTG AAA GAT      1383
Gly Ile Asp Leu Ser Thr Asp Lys Met Ala Met Gln Arg Leu Lys Asp
220                 225                 230

GCG GCT GAA AAA GCG AAG AAA GAC CTT TCT GGT GTA ACT TCA ACA CAA      1431
Ala Ala Glu Lys Ala Lys Lys Asp Leu Ser Gly Val Thr Ser Thr Gln
235                 240                 245                 250

ATC AGC TTG CCA TTT ATC ACT GCA GGT GAG GCT GGA CCT CTT CAC TTG      1479
Ile Ser Leu Pro Phe Ile Thr Ala Gly Glu Ala Gly Pro Leu His Leu
                255                 260                 265

GAA ATG ACT TTA ACT CGT GCG AAA TTT GAT GAT TTG ACT CGT GAC CTT      1527
Glu Met Thr Leu Thr Arg Ala Lys Phe Asp Asp Leu Thr Arg Asp Leu
            270                 275                 280

GTT GAA CGT ACA AAA GTT CCA GTT CGT CAA GCC CTT TCA GAT GCA GGT      1575
Val Glu Arg Thr Lys Val Pro Val Arg Gln Ala Leu Ser Asp Ala Gly
        285                 290                 295

TTG AGC TTG TCA GAA ATC GAC GAA GTT ATC CTT GTT GGT GGT TCA ACT      1623
Leu Ser Leu Ser Glu Ile Asp Glu Val Ile Leu Val Gly Gly Ser Thr
300                 305                 310

CGT ATC CCT GCC GTT GTT GAA GCT GTT AAA GCT GAA ACT GGT AAA GAA      1671
Arg Ile Pro Ala Val Val Glu Ala Val Lys Ala Glu Thr Gly Lys Glu
315                 320                 325                 330

CCA AAC AAA TCA GTA AAC CCT GAT GAA GTA GTT GCT ATG GGT GCG GCT      1719
Pro Asn Lys Ser Val Asn Pro Asp Glu Val Val Ala Met Gly Ala Ala
                335                 340                 345

ATC CAA GGT GGT GTG ATT ACT GGT GAT GTC AAG GAT GTT GTC CTT CTT      1767
Ile Gln Gly Gly Val Ile Thr Gly Asp Val Lys Asp Val Val Leu Leu
            350                 355                 360

GAT GTA ACG CCA TTG TCA CTT GGT ATC GAA ACA ATG GGT GGA GTA TTT      1815
Asp Val Thr Pro Leu Ser Leu Gly Ile Glu Thr Met Gly Gly Val Phe
        365                 370                 375

ACA AAA CTT ATC GAT CGC AAC ACT ACA ATC CCA ACA TCT AAA TCA CAA      1863
Thr Lys Leu Ile Asp Arg Asn Thr Thr Ile Pro Thr Ser Lys Ser Gln
380                 385                 390

GTC TTC TCA ACA GCA GCA GAC AAC CAA CCA GCC GTT GAT ATC CAC GTT      1911
Val Phe Ser Thr Ala Ala Asp Asn Gln Pro Ala Val Asp Ile His Val
395                 400                 405                 410

CTT CAA GGT GAA CGC CCA ATG GCA GCA GAT AAC AAG ACT CTT GGA CGC      1959
Leu Gln Gly Glu Arg Pro Met Ala Ala Asp Asn Lys Thr Leu Gly Arg
                415                 420                 425

TTC CAA TTG ACT GAT ATC CCA GCT GCA CCT CGT GGA ATT CCT CAA ATC      2007
Phe Gln Leu Thr Asp Ile Pro Ala Ala Pro Arg Gly Ile Pro Gln Ile
            430                 435                 440

GAA GTA ACA TTT GAC ATC GAC AAG AAC GGT ATC GTG TCT GTT AAG GCC      2055
Glu Val Thr Phe Asp Ile Asp Lys Asn Gly Ile Val Ser Val Lys Ala
        445                 450                 455

AAA GAC CTT GGA ACT CAA AAA GAA CAA ACT ATT GTC ATC CAA TCG AAC      2103
Lys Asp Leu Gly Thr Gln Lys Glu Gln Thr Ile Val Ile Gln Ser Asn
460                 465                 470
```

```
TCA GGT TTG ACT GAC GAA GAA ATC GAC CGC ATG ATG AAA GAT GCA GAA        2151
Ser Gly Leu Thr Asp Glu Glu Ile Asp Arg Met Met Lys Asp Ala Glu
475                 480                 485                 490

GCA AAC GCT GAA TCC GAT AAG AAA CGT AAA GAA GAA GTA GAC CTT CGT        2199
Ala Asn Ala Glu Ser Asp Lys Lys Arg Lys Glu Glu Val Asp Leu Arg
                495                 500                 505

AAT GAA GTG GAC CAA GCA ATC TTT GCG ACT GAA AAG ACA ATC AAG GAA        2247
Asn Glu Val Asp Gln Ala Ile Phe Ala Thr Glu Lys Thr Ile Lys Glu
            510                 515                 520

ACT GAA GGT AAA GGC TTC GAC GCA GAA CGT GAC GCT GCC CAA GCT GCC        2295
Thr Glu Gly Lys Gly Phe Asp Ala Glu Arg Asp Ala Ala Gln Ala Ala
        525                 530                 535

CTT GAT GAC CTT AAG AAA GCT CAA GAA GAC AAC AAC TTG GAC GAC ATG        2343
Leu Asp Asp Leu Lys Lys Ala Gln Glu Asp Asn Asn Leu Asp Asp Met
    540                 545                 550

AAA GCA AAA CTT GAA GCA TTG AAC GAA AAA GCT CAA GGA CTT GCT GTT        2391
Lys Ala Lys Leu Glu Ala Leu Asn Glu Lys Ala Gln Gly Leu Ala Val
555                 560                 565                 570

AAA CTC TAC GAA CAA GCC GCA GCA GCG CAA CAA GCT CAA GAA GGA GCA        2439
Lys Leu Tyr Glu Gln Ala Ala Ala Ala Gln Gln Ala Gln Glu Gly Ala
                575                 580                 585

GAA GGC GCA CAA GCA ACA GGA AAC GCA GGC GAT GAC GTC GTA GAC GGA        2487
Glu Gly Ala Gln Ala Thr Gly Asn Ala Gly Asp Asp Val Val Asp Gly
            590                 595                 600

GAG TTT ACG GAA AAG TAAGATGAGT GTATTGGATG AAGAGTATCT AAAAAATACA        2542
Glu Phe Thr Glu Lys
        605

CGAAAAGTTT ATAATGATTT TTGTAATCAA GCTGATAACT ATAGAACATC AAAAGATTTT      2602

ATTGATAATA TTCCAATAGA ATATTTAGCT AGATATAGAG AAATTATATT AGCTGAGCAT      2662

GATAGTTGTG TCAAAAATGA TGAAGCGGTA AGGAATTTTG TTACCTCAGT ATTGTTGTCT      2722

GCATTTGTAT CGGCGATGGT ATCAGCTATG ATATCATTAG AAATACAAAC ATATAAATTT      2782

GTAATACCGT TCATAATTGG TATGATTTGG ACAGTAGTTG TATTTCTTAT GATCAATTGG      2842

AATTATATAG GCAAATACTA AGAAGAGACA AAAATATATA AATATTTCTG TACTTATAGG      2902

ATATTTAAAA TCCAAATAAA GTTAATTTAC TTATTTGCAG AGGTTGCAAC CCAGCCTCTG      2962

TTTTTCGATA AAAAGGGACG GAATCTCATT TGTTTGGGTT TTGTCTCATC AATAGAAAGG      3022

AACAAAGAGT GTTCGTAACT GAACACGGGT TTCAGAATTT CTTACTAAAT ATAAAAGAAA      3082

GGAATTGAAC CCGACCTAAA TGGTGGTTCG ATTCAGAACA TCAATAGAAA GGAATAAGGG      3142

TGTTCGTAAC TGAACACGGG CTACGGACTG TGCCAAAAAG ATAGTTTTTT CTAGGACGTA      3202

AGCGTCCGTC GTCAAAACTC CTAGATGGCT GTGTCCGTTT GACGCCCTTT GTATCTTGAA      3262

TT ATG AAC AAT ACT GAA TTT TAT GAT CGT CTG GGG GTA TCC AAA AAC    3309
         Met Asn Asn Thr Glu Phe Tyr Asp Arg Leu Gly Val Ser Lys Asn
         1               5                  10                  15

GCT TCG GCA GAC GAA ATC AAA AAG GCT TAT CGT AAG CTT TCC AAA AAA        3357
Ala Ser Ala Asp Glu Ile Lys Lys Ala Tyr Arg Lys Leu Ser Lys Lys
                20                  25                  30

TAT CAC CCA GAT ATC AAC AAG GAG CCT GGT GCT GAG GAC AAG TAC AAG        3405
Tyr His Pro Asp Ile Asn Lys Glu Pro Gly Ala Glu Asp Lys Tyr Lys
            35                  40                  45

GAA GTT CAA GAA GCC TAT GAG ACT TTG AGT GAC GAC CAA AAA CGT GCT        3453
Glu Val Gln Glu Ala Tyr Glu Thr Leu Ser Asp Asp Gln Lys Arg Ala
        50                  55                  60

GCC TAT GAC CAG TAT GGT GCT GCA GGC GCC AAT GGT GGT TTT GGT GGA        3501
Ala Tyr Asp Gln Tyr Gly Ala Ala Gly Ala Asn Gly Gly Phe Gly Gly
    65                  70                  75
```

| | | |
|---|---|---|
| GCT GGT GGT TTC GGC GGT TTC AAT GGG GCA GGT GGC TTC GGT GGT TTT<br>Ala Gly Gly Phe Gly Gly Phe Asn Gly Ala Gly Gly Phe Gly Gly Phe<br>80                        85                            90                          95 | | 3549 |
| GAG GAT ATT TTC TCA AGT TTC TTC GGC GGA GGC GGT TCT TCG CGC AAT<br>Glu Asp Ile Phe Ser Ser Phe Phe Gly Gly Gly Gly Ser Ser Arg Asn<br>100                      105                        110 | | 3597 |
| CCA AAC GCT CCT CGC CAA GGA GAT GAT CTC CAG TAT CGT GTC AAT TTG<br>Pro Asn Ala Pro Arg Gln Gly Asp Asp Leu Gln Tyr Arg Val Asn Leu<br>115                      120                      125 | | 3645 |
| ACC TTT GAA GAA GCT ATC TTC GGA ACT GAG AAG GAA GTT AAG TAT CAT<br>Thr Phe Glu Glu Ala Ile Phe Gly Thr Glu Lys Glu Val Lys Tyr His<br>130                      135                      140 | | 3693 |
| CGT GAA GCT GGC TGT CGT ACA TGT AAT GGA TCT GGT GCT AAG CCA GGG<br>Arg Glu Ala Gly Cys Arg Thr Cys Asn Gly Ser Gly Ala Lys Pro Gly<br>145                      150                      155 | | 3741 |
| ACA AGT CCA GTC ACT TGT GGA CGC TGT CAT GGC GCT GGT GTC ATT AAC<br>Thr Ser Pro Val Thr Cys Gly Arg Cys His Gly Ala Gly Val Ile Asn<br>160                      165                      170                      175 | | 3789 |
| GTC GAT ACG CAG ACT CCT CTT GGT ATG ATG CGT CGC CAA GTA ACC TGT<br>Val Asp Thr Gln Thr Pro Leu Gly Met Met Arg Arg Gln Val Thr Cys<br>                      180                      185                      190 | | 3837 |
| GAT GTC TGT CAC GGT CGA GGA AAA GAA ATC AAA TAT CCA TGT ACA ACC<br>Asp Val Cys His Gly Arg Gly Lys Glu Ile Lys Tyr Pro Cys Thr Thr<br>                      195                      200                      205 | | 3885 |
| TGT CAT GGA ACA GGT CAT GAG AAA CAA GCT CAT AGC GTA CAT GTG AAA<br>Cys His Gly Thr Gly His Glu Lys Gln Ala His Ser Val His Val Lys<br>        210                      215                      220 | | 3933 |
| ATC CCT GCT GGT GTG GAA ACA GGT CAA CAA ATT CGC CTC GCT GGT CAA<br>Ile Pro Ala Gly Val Glu Thr Gly Gln Gln Ile Arg Leu Ala Gly Gln<br>225                      230                      235 | | 3981 |
| GGT GAA GCA GGC TTT AAC GGT GGA CCT TAT GGT GAC TTG TAT GTA GTA<br>Gly Glu Ala Gly Phe Asn Gly Gly Pro Tyr Gly Asp Leu Tyr Val Val<br>240                      245                      250                      255 | | 4029 |
| GTT TCT GTG GAA GCT AGT GAC AAG TTT GAA CGT GAA GGA ACG ACT ATC<br>Val Ser Val Glu Ala Ser Asp Lys Phe Glu Arg Glu Gly Thr Thr Ile<br>                      260                      265                      270 | | 4077 |
| TTC TAC AAT CTC AAC CTC AAC TTT GTC CAA GCG GCT CTT GGT GAT ACA<br>Phe Tyr Asn Leu Asn Leu Asn Phe Val Gln Ala Ala Leu Gly Asp Thr<br>        275                      280                      285 | | 4125 |
| GTA GAT ATT CCA ACT GTT CAC GGT GAT GTT GAA TTG GTT ATT CCA GAG<br>Val Asp Ile Pro Thr Val His Gly Asp Val Glu Leu Val Ile Pro Glu<br>290                      295                      300 | | 4173 |
| GGA ACT CAG ACT GGT AAG AAA TTC CGC CTA CGT AGT AAG GGG GCA CCG<br>Gly Thr Gln Thr Gly Lys Lys Phe Arg Leu Arg Ser Lys Gly Ala Pro<br>305                      310                      315 | | 4221 |
| AGC CTT CGT GGC GGT GCA GTT GGT GAC CAA TAC GTT ACT GTT AAT GTC<br>Ser Leu Arg Gly Gly Ala Val Gly Asp Gln Tyr Val Thr Val Asn Val<br>320                      325                      330                      335 | | 4269 |
| GTA ACA CCG ACA GGC TTG AAC GAC CGC CAA AAA GTA GCC TTG AAA GAA<br>Val Thr Pro Thr Gly Leu Asn Asp Arg Gln Lys Val Ala Leu Lys Glu<br>        340                      345                      350 | | 4317 |
| TTC<br>Phe | | 4320 |

(2) INFORMATION FOR SEQ ID NO:5:

(i) SEQUENCE CHARACTERISTICS:
        (A) LENGTH: 607 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ser Lys Ile Ile Gly Ile Asp Leu Gly Thr Thr Asn Ser Ala Val
 1               5                  10                  15

Ala Val Leu Glu Gly Thr Glu Ser Lys Ile Ile Ala Asn Pro Glu Gly
                20                  25                  30

Asn Arg Thr Thr Pro Ser Val Val Ser Phe Lys Asn Gly Glu Ile Ile
            35                  40                  45

Val Gly Asp Ala Ala Lys Arg Gln Ala Val Thr Asn Pro Asp Thr Val
 50                  55                  60

Ile Ser Ile Lys Ser Lys Met Gly Thr Ser Glu Lys Val Ser Ala Asn
 65                  70                  75                  80

Gly Lys Glu Tyr Thr Pro Gln Glu Ile Ser Ala Met Ile Leu Gln Tyr
                85                  90                  95

Leu Lys Gly Tyr Ala Glu Asp Tyr Leu Gly Glu Lys Val Thr Lys Ala
                100                 105                 110

Val Ile Thr Val Pro Ala Tyr Phe Asn Asp Ala Gln Arg Gln Ala Thr
            115                 120                 125

Lys Asp Ala Gly Lys Ile Ala Gly Leu Glu Val Glu Arg Ile Val Asn
130                 135                 140

Glu Pro Thr Ala Ala Leu Ala Tyr Gly Leu Asp Lys Thr Asp Lys
145                 150                 155                 160

Glu Glu Lys Ile Leu Val Phe Asp Leu Gly Gly Thr Phe Asp Val
                165                 170                 175

Ser Ile Leu Glu Leu Gly Asp Gly Val Phe Asp Val Leu Ser Thr Ala
                180                 185                 190

Gly Asp Asn Lys Leu Gly Gly Asp Asp Phe Asp Gln Lys Ile Ile Asp
                195                 200                 205

His Leu Val Ala Glu Phe Lys Lys Glu Asn Gly Ile Asp Leu Ser Thr
        210                 215                 220

Asp Lys Met Ala Met Gln Arg Leu Lys Asp Ala Ala Glu Lys Ala Lys
225                 230                 235                 240

Lys Asp Leu Ser Gly Val Thr Ser Thr Gln Ile Ser Leu Pro Phe Ile
                245                 250                 255

Thr Ala Gly Glu Ala Gly Pro Leu His Leu Glu Met Thr Leu Thr Arg
                260                 265                 270

Ala Lys Phe Asp Asp Leu Thr Arg Asp Leu Val Glu Arg Thr Lys Val
                275                 280                 285

Pro Val Arg Gln Ala Leu Ser Asp Ala Gly Leu Ser Leu Ser Glu Ile
290                 295                 300

Asp Glu Val Ile Leu Val Gly Gly Ser Thr Arg Ile Pro Ala Val Val
305                 310                 315                 320

Glu Ala Val Lys Ala Glu Thr Gly Lys Glu Pro Asn Lys Ser Val Asn
                325                 330                 335

Pro Asp Glu Val Val Ala Met Gly Ala Ala Ile Gln Gly Val Ile
                340                 345                 350

Thr Gly Asp Val Lys Asp Val Leu Leu Asp Val Thr Pro Leu Ser
                355                 360                 365

Leu Gly Ile Glu Thr Met Gly Gly Val Phe Thr Lys Leu Ile Asp Arg
                370                 375                 380

Asn Thr Thr Ile Pro Thr Ser Lys Ser Gln Val Phe Ser Thr Ala Ala
385                 390                 395                 400

Asp Asn Gln Pro Ala Val Asp Ile His Val Leu Gln Gly Glu Arg Pro
                405                 410                 415
```

Met Ala Ala Asp Asn Lys Thr Leu Gly Arg Phe Gln Leu Thr Asp Ile
        420                 425                 430

Pro Ala Ala Pro Arg Gly Ile Pro Gln Ile Glu Val Thr Phe Asp Ile
        435                 440                 445

Asp Lys Asn Gly Ile Val Ser Val Lys Ala Lys Asp Leu Gly Thr Gln
        450                 455                 460

Lys Glu Gln Thr Ile Val Ile Gln Ser Asn Ser Gly Leu Thr Asp Glu
465                 470                 475                 480

Glu Ile Asp Arg Met Met Lys Asp Ala Glu Ala Asn Ala Glu Ser Asp
                485                 490                 495

Lys Lys Arg Lys Glu Glu Val Asp Leu Arg Asn Glu Val Asp Gln Ala
        500                 505                 510

Ile Phe Ala Thr Glu Lys Thr Ile Lys Glu Thr Glu Gly Lys Gly Phe
        515                 520                 525

Asp Ala Glu Arg Asp Ala Ala Gln Ala Ala Leu Asp Asp Leu Lys Lys
        530                 535                 540

Ala Gln Glu Asp Asn Asn Leu Asp Asp Met Lys Ala Lys Leu Glu Ala
545                 550                 555                 560

Leu Asn Glu Lys Ala Gln Gly Leu Ala Val Lys Leu Tyr Glu Gln Ala
                565                 570                 575

Ala Ala Ala Gln Gln Ala Gln Glu Gly Ala Glu Gly Ala Gln Ala Thr
        580                 585                 590

Gly Asn Ala Gly Asp Asp Val Val Asp Gly Glu Phe Thr Glu Lys
        595                 600                 605

(2) INFORMATION FOR SEQ ID NO:6:

(i) SEQUENCE CHARACTERISTICS:
        (A) LENGTH: 352 amino acids
        (B) TYPE: amino acid
        (D) TOPOLOGY: linear (ii) MOLECULE TYPE: protein (xi) SEQUENCE DESCRIPTION: SEQ ID NO:6:

Met Asn Asn Thr Glu Phe Tyr Asp Arg Leu Gly Val Ser Lys Asn Ala
1                   5                   10                  15

Ser Ala Asp Glu Ile Lys Lys Ala Tyr Arg Lys Leu Ser Lys Lys Tyr
            20                  25                  30

His Pro Asp Ile Asn Lys Glu Pro Gly Ala Glu Asp Lys Tyr Lys Glu
        35                  40                  45

Val Gln Glu Ala Tyr Glu Thr Leu Ser Asp Gln Lys Arg Ala Ala
    50                  55                  60

Tyr Asp Gln Tyr Gly Ala Ala Gly Ala Asn Gly Phe Gly Gly Ala
65                  70                  75                  80

Gly Gly Phe Gly Gly Phe Asn Gly Ala Gly Gly Phe Gly Gly Phe Glu
                85                  90                  95

Asp Ile Phe Ser Ser Phe Phe Gly Gly Gly Ser Ser Arg Asn Pro
        100                 105                 110

Asn Ala Pro Arg Gln Gly Asp Asp Leu Gln Tyr Arg Val Asn Leu Thr
        115                 120                 125

Phe Glu Glu Ala Ile Phe Gly Thr Glu Lys Glu Val Lys Tyr His Arg
        130                 135                 140

Glu Ala Gly Cys Arg Thr Cys Asn Gly Ser Gly Ala Lys Pro Gly Thr
145                 150                 155                 160

-continued

```
Ser Pro Val Thr Cys Gly Arg Cys His Gly Ala Gly Val Ile Asn Val
            165                 170                 175

Asp Thr Gln Thr Pro Leu Gly Met Met Arg Arg Gln Val Thr Cys Asp
            180                 185                 190

Val Cys His Gly Arg Gly Lys Glu Ile Lys Tyr Pro Cys Thr Thr Cys
        195                 200                 205

His Gly Thr Gly His Glu Lys Gln Ala His Ser Val His Val Lys Ile
    210                 215                 220

Pro Ala Gly Val Glu Thr Gly Gln Gln Ile Arg Leu Ala Gly Gln Gly
225                 230                 235                 240

Glu Ala Gly Phe Asn Gly Gly Pro Tyr Gly Asp Leu Tyr Val Val Val
                245                 250                 255

Ser Val Glu Ala Ser Asp Lys Phe Glu Arg Glu Gly Thr Thr Ile Phe
            260                 265                 270

Tyr Asn Leu Asn Leu Asn Phe Val Gln Ala Ala Leu Gly Asp Thr Val
        275                 280                 285

Asp Ile Pro Thr Val His Gly Asp Val Glu Leu Val Ile Pro Glu Gly
        290                 295                 300

Thr Gln Thr Gly Lys Lys Phe Arg Leu Arg Ser Lys Gly Ala Pro Ser
305                 310                 315                 320

Leu Arg Gly Gly Ala Val Gly Asp Gln Tyr Val Thr Val Asn Val Val
                325                 330                 335

Thr Pro Thr Gly Leu Asn Asp Arg Gln Lys Val Ala Leu Lys Glu Phe
                340                 345                 350
```